United States Patent [19]

Nevalainen et al.

[11] Patent Number: 5,834,286
[45] Date of Patent: Nov. 10, 1998

[54] RECOMBINANT CELLS THAT EXPRESS PHYTATE DEGRADING ENZYMES IN DESIRED RATIOS

[75] Inventors: Helena K. M. Nevalainen, North Epping, Australia; Marja T. Paloheimo, Helsinki, Finland; Richard B. Fagerström, Espoo, Finland; Arja S. K. Miettinen-Oinonen, Masala, Finland; Marja K. Turunen, Helsinki, Finland; John A. Rambosek; Christopher S. Piddington, both of Seattle, Wash.; Christine S. Houston, Bothell, Wash.; Michael A. Cantrell, Moscow, Id.

[73] Assignee: Röhm Enzyme Finland Oy, Rajamäki, Finland

[21] Appl. No.: 374,652

[22] PCT Filed: Jul. 27, 1993

[86] PCT No.: PCT/US93/07058

§ 371 Date: May 24, 1995

§ 102(e) Date: May 24, 1995

[87] PCT Pub. No.: WO94/03072

PCT Pub. Date: Feb. 17, 1994

Related U.S. Application Data

[63] Continuation-in-part of Ser. No. 925,401, Jul. 31, 1992, abandoned.

[51] Int. Cl.⁶ .............. C12N 1/15; C12N 1/21; C12N 9/16; C12S 3/00
[52] U.S. Cl. .............. 435/196; 435/252.3; 435/252.31; 435/252.33; 435/254.3; 435/254.5; 435/254.6; 435/254.9; 435/254.11; 435/325; 426/635
[58] Field of Search .............. 536/232; 435/325, 435/254.11, 254.3, 252.3, 196, 320.1, 252.31, 252.33, 254.5, 254.6, 254.9; 426/635

[56] References Cited

U.S. PATENT DOCUMENTS

| | | |
|---|---|---|
| 3,297,548 | 1/1967 | Ware et al. . |
| 3,966,971 | 6/1976 | Morehouse et al. .............. 435/272 |
| 4,914,029 | 4/1990 | Caransa et al. . |
| 5,217,959 | 6/1993 | Sabin ............................. 514/23 |
| 5,298,405 | 3/1994 | Nevalainen et al. ............ 435/209 |
| 5,436,156 | 7/1995 | Van Gorcom et al. ........ 435/252.3 |
| 5,443,979 | 8/1995 | Vanderbeke et al. ............ 435/195 |
| 5,554,399 | 9/1996 | Vanderbeke et al. ............ 426/49 |
| 5,593,963 | 1/1997 | Van Ooijen et al ............. 514/12 |

FOREIGN PATENT DOCUMENTS

| | | |
|---|---|---|
| 0 215 594 A2 | 3/1987 | European Pat. Off. . |
| 0 244 234 A2 | 11/1987 | European Pat. Off. . |
| 0 287 152 A1 | 10/1988 | European Pat. Off. . |
| 0380343 | 8/1990 | European Pat. Off. . |
| 420538 | 4/1991 | European Pat. Off. . |
| 0 449 375 A2 | 10/1991 | European Pat. Off. . |
| 0 619 369 A1 | 10/1994 | European Pat. Off. . |
| WO91/05053 | 4/1991 | WIPO . |
| WO 92/01797 | 2/1992 | WIPO . |
| WO 94/03072 | 2/1994 | WIPO . |

OTHER PUBLICATIONS

MacRae et al., 71:339–348, 1988.

(List continued on next page.)

*Primary Examiner*—Eric Grimes
*Attorney, Agent, or Firm*—Sterne, Kessler, Goldstein & Fox P.L.L.C.

[57] ABSTRACT

The present invention provides a recombinant combination strain which is capable of over-expressing at least two different genes under two separate promoters in filamentous fungi. The genes encode phytase and pH 2.5 acid phosphatase. Mixtures containing desired ratios of the two enzymes are prepared by recombinant DNA techniques. The enzyme mixtures show a cooperative effect in the degradation of phytic acid and its salts. The preferred ratios of the two enzymes are from about 3:1 to about 16:1.

38 Claims, 31 Drawing Sheets

OTHER PUBLICATIONS

Bailey, M.J. and K.M.H. Nevalainen, "Induction, isolation and testing of stable *Trichoderma reesei* mutants with improved production of solubilizing cellulase," *Enzyme Microb. Technol.* 3:153–157 (1981).

Ehrlich, K.C. et al., "Identification and cloning of a second phytase gene (phyB) from *Aspergillus niger (ficuum)*," *Biochem. Biophys. Res. Comm.* 195(1):53–57 (Aug. 1993).

Fujiwara, S. et al., "Hydrolysis of phytate in soybean by phytase from Rhizopus sp. EF-78," *Chem. Abstr.* 106:266, Abstract No. 115629m (1987).

Gibson, D.M., "Production of Extracellular Phytase from *Aspergillus ficuum* on Starch Media," *Biotechnol. Letts.* 9(5):305–310 (1987).

Gibson, D.M. and A.B.J. Ullah, "Phytases and Their Action on Phytic Acid," *Inositol Metabolism in Plants*, Mooré, D.J. et al., eds., Wiley–Liss, New York, publ., pp. 77–92 (1990).

Houston, C.S. et al., "The Cloning and Overexpression of Phytase and pH 2.5 Acid Phosphatase in *Aspergillus niger*: Applications to a Commercial Product," presented at Society for Industrial Microbiology annual meeting, San Diego, CA, Aug. 9–14, 1992.

Innis, M.A. et al., "Expression, Glycosylation, and Secretion of an Aspergillus Glucoamylase by *Saccharomyces cerevisiae*," *Science* 288:21–26 (Apr. 1985).

"Microbial Phytase to be Used in Food Processing," *European Biotechnology Newsletter* 75:05 (Sep. 1989).

Nayini, N.R. and P. Markakis, "The Phytase of Yeast," *Lebensm.–Wiss. u. –Technol.* 17: 24–26 (1984).

Ohtsuka, E. et al., "An Alternative Approach to Deoxyoligonucleotides as Hybridization Probes by Insertion of Deoxyinosine at Ambiguous Codon Positions," *J. Biol. Chem.* 260(5):2605–2608 (Mar. 1985).

Penttilä, M. et al., "A versatile transformation system for the cellulolytic filamentous fungus *Trichoderma reesei*," *Gene* 61: 155–164 (1987).

Powar, V.K. and V. Jagannathan, "Purification and Properties of Phytate–Specific Phosphatase from *Bacillus subtilis*," *J. Bacteriol.* 151(3):1102–1108 (Sep. 1982).

Saloheimo, M. and M.–L. Niku–Paavola, "Heterologous Production of a Ligninolytic Enzyme: Expression of the *Phlebia radiata* Laccase Gene in *Trichoderma reesei*," *Bio/Technol.* 9:987–990 (Oct. 1991).

Ullah, A.H.J. and B.J. Cummins, "*Aspergillus ficuum* Extracellular pH 6.0 Optimum Acid Phosphatase: Purification, N–Terminal Amino Acid Sequence, and Biochemical Characterization," *Prep. Biochem.* 18(1):37–65 (1988).

Ullah, A.H.J. and H.C. Dischinger, Jr., "*Aspergillus ficuum* Extracellular Phytase: Peptide Mapping and Purification by Reverse Phase Chromatography," *Ann. New York Acad. Sci.* 613:878–882 (Dec. 1990).

Ullah, A.H.J. and C. Dischinger, "Identification of active–site residues in *Aspergillus ficuum* extracellular pH 2.5 optimum acid phosphatase," *Biochem. Biophys. Res. Comm.* 192:754–759 (1993).

van Hartingsveldt, W. et al., "Cloning, characterization and overexpression of the phytase–encoding gene (phyA) of *Aspergillus niger*," *Gene* 127:87–94 (May 1993).

Yamada, K. et al., "Phytase from *Aspergillus terreus*: Part I. Production, Purification and Some General Properties of the Enzyme," *Agr. Biol. Chem.* 32(10): 1275–1282 (1968).

Yamamoto, S. et al., "Chemical and Physicochemical Properties of Phytase from *Aspergillus terreus*," *Agr. Biol. Chem.* 36(12):2097–2103 (1972).

Dialog File 16, "Strategic Partners Report," *Genetic Technology News* (Oct. 1991).

Dialog File 583, "Collaborative research gains bio–technology break through," *International Milling Flour & Feed (IMFF)*, Infomat No. 04630360, p. 6 (Oct. 1991).

Arima, K., et al., "The Nucleotide Sequence of the Yeast PH05 Gene: A Putative Precursor of Repressible Acid Phosphatase Contains a Signal Peptide," *Nucleic Acids Res.* 11:1657–1672 (1983).

Bajwa, W. et al., "Structural Analysis of the Two Tandemly Repeated Acid Phosphatase Genes in Yeast," *Nucleic Acids Res.* 12:7721–7739 (1984).

Elliott, S. et al., "Isolation and Characterization of the Structural Gene for Secreted Acid Phosphatase from *Schizosaccharomyces pombe*," *J. Biol. Chem.* 261:2936–2941 (1986).

Touati, E. et al., "The Structure of the Promotor and Amino Terminal Region of pH2.5 Acid Phosphatase Structural Gene (appA) of E. coli: A Negative Control of Transcription Mediated by cyclic AMP," *Biochimie* 69:215–221 (1987).

Himeno, M. et al., "Isolation and Sequencing of a cDNA Clone Encoding Acid Phosphatase in Rat Liver Lysosomes," *Biochem. Biophys. Res. Comm.* 162:1044–1053 (1989).

Shieh, T.R. et al., "Regulation of the Formation of Acid Phosphatase by Inorganic Phosphate in *Aspergillus ficuum*," *J. Bacteriol.* 100:1161–1165 (1969).

Shieh, T.R. et al., "Survey of Microorganisms for the Production of Extracellular Phytase," *Appl. Microbiol.* 16:1348–1351 (1968).

Ullah, H.J. et al., "Cyclohexanedione Modification of Arginine at the Active Site of *Aspergillus ficuum* Phytase," *Biochem. Biophys. Res. Comm.* 178(1):45–53 (1991).

Ullah, H.J., "*Aspergillus ficuum* Phytase: Partial Primary Structure, Substrate Selectivity, and Kinetic Characterization," *Preparative Biochemistry* 18(4):459–471 (1988).

Ullah, H.J. et al., "Purification, N–terminal Amino Acid Sequence and Characterization of pH2.5 Optimum Acid Phosphatase (E.C. 3.1.3.2) from *Aspergillus ficuum*," *Preparative Biochem.* 17(4):397–422 (1987).

Christen, A.A. et al., "Cloning of the Phytase Gene From Germinating Soybeans," *J. Cell Biochem. Suppl.* O.(12 Part C):190 (1988).

Hayakawa, T. et al., "Purification and Characterization of Acid Phosphatases With or Without Phytase Activity From Rice Bean," *Agric. Biol. Chem.* 53(6):1475–1483 (1989).

Ullah, A.H. et al., "Extracellular Phytase (E.C. 3.1.3.8) From *Aspergillus ficuum* NRRL 3135: Purification and Characterization," *Prep. Biochem.* 17(1):63–91 (1987).

Ullah, A.H.J. et al., "Immobilization of *Aspergillus ficuum* Phytase: Product Characterization of the Bioreactor," *Prep. Biochem.* 18(4):483–489 (1988).

Youssef, K.A. et al., "Purification and General Properties of Extracellular Phytase *Aspergillus ficuum*," *Zentralbl. Mikrobiol.* 142:397–402 ()1987).

Gibson, D.M. et al., "Purification and Characterization of Phytase From Cotyledons of Germinating Soybean Seeds," *Arch. Biochem. Biophys.* 260(2):503–513 (1988).

Ghareib, M. et al., "Isolation and Characterization of Intracellular Phytase From *Macrophomia phaseolina*," *Zentralbl. Mikrobiol.* 143:397–403 (1988).

Ullah, A.H.J. et al., "*Aspergillus ficuum* Extracellular Phytase: Immobilization on Glutaraldehyde–actived Silicate," *Ann. N.Y. Acad. Sci.* 542:102–105 (1988).

Ullah, A.H.J., "Production, Rapid Purification and Catalytic Characterization of Extracellular Phytase From *Aspergillus ficuum*," *Prep. Biochem.* 18(4):443–458 (1988).

Mullaney, E.J. et al., "Positive Identification of a Lamba gt11 Clone Containing a Region of Fungal Phytase Gene by Immunoprobe and Sequence Verification," *Appl. Microbiol. Biotechnol.* 35:611–614 (1991).

Samson, R.A., In Aspergillus: *Biology and Industrial Applications*, (Bennett, J.W. et al., Eds), Butterworth–Heinemann, Stoneham, MA, pp. 355–390 (1992).

Zyla, K., "Acid Phosphatases Purified From Industrial Waste Mycelium of *Aspergillus niger* Used to Produce Citric Acid," *ACTA Biotechnol.* 10(4):319–327 (1990).

Rambosek, J. et al., "Recombinant DNA in Filamentous Fungi: Progress and Prospects," *CRC Critical Reviews in Biotechnology* 6(4):357–393 (1987).

Nelson T.S. et al., "Effect of Supplemental Phytase on the Utilization of Phytate Phosphorus by Chicks," *J. Nutrition* 101:1289–1294 (1971).

FIG. 9A

```
                                                                                                              >BamH1
                                                                                                              <
1301 CATGGACATG TGCTCCTTCG ACACCATCTC CACCAGCACC GTCGACACCA AGTGTCCCC  CTTCTGTGAC ATGACGAATG GATCCACTAC
      M  D  M   C  S  F    D  T  I  S   T  S  T     V  D  T    K  L  S  P     F  C  D      M  T  N  G  S  T  T
1401 GACTACCTCC AGTCCCTGAA AAATACTAC GGCCATGGCG CTCGGCCCG ACCAGGGCG TGGCTACGC ATCGCCGTC
      D  Y  L   Q  S  L  K   K  Y  Y   G  H  G    A  G  N  P    T  Q  G    V  G  Y  A   N  E  L   I  A  R
1501 TCACCCACTC GCCTGTCCAC GATGACACCA GCTCCAACCA CACCTTGGAC TGAAACCCAG CTACCTTCCC GCTCAACTCT ACTCTCTACG CGGACTTTTC
      L  T  H  S    P  V  H   D  D  T   S  S  N  H    T  L  D    S  N  P    A  T  F  P  L  N  S    T  L  Y     A  D  F  S
1601 CCACGATAAC GGCATCATCT CTATCCTCTT TGCTTTGGGT GCTACAACG GCACTAAGCC GCTGTCTACC ACGACCGTGG AGAATATCAC CCAGACAGAT
      H  D  N    G  I  I    S  I  L  F    A  L  G    L  Y  N    G  T  K  P    L  S  T    T  T  V    E  N  I  T    Q  T  D
1701 GGGTTCTCGT CTGCTTGGAC GGTTCCGTTT GCTTCCGGTC TGCCAGGCAG TGGATGATGCAG AGCAGGAGCC GCTGGTCCGT GTCTTGGTTA
      G  F  S    S  A  W  T    V  P  F     A  S  R     P  I  D  A    L  G  R    C  T  R      D  S  F  V     R  G  L     S  F  A     R  S  G  G
1801 ATGATCGCGT TGTCCCGCTG CATGGGTGTC CAATTGATGC CTACCTTGAA CTTAGCTCTG GGTAGATATT TGGTCCCTT ATGGCACTCG ACGTACAGCA TAATACAACT
      N  D  R  V     V  P  L     H  G  C     P  I  D  A     L  G  R     C  T  R      D  S  F  V     R  G  L     S  F  A     R  S  G  G
1901 TGATTGGGCG GAGTGTTCTG CTTAGCTCTG ATTACTTCAT GTATGTATTT ACGAAGATGT
      D  W  A     E  C  S      A  *
                                                                                                                       >Sph1
                                                                                                                       <
2001 ACATATCGAA ATATCGATGA TGACTACTCC GGTAGATATT TGGTCCCCTT CTATCCTTCG ATGGCACTCG ACGTACAGCA TAATACAACT
2101 TCAGCATTAA CAAACGAACA AATAATATTA TACACTCCTC CCCAATGCAA TAACAACGC TCATATAGAT ACAATACAAT ACATCCATCC
2201 CTACCCTCAA GTCCACCCAT CCCATAATCA AATCCCTACT CCTTCCCAGA ACCCACCCCC GAAGGAGTAA TAGTAGTAGT AGAAGAAGCA
2301 GACGGACCTCT CCACCAACCT CTTCGGCCTC TTATCCCCAT AGCTATACA CACACGAACA CACCAAATAG TCAGCATGC
```

FIG.9B

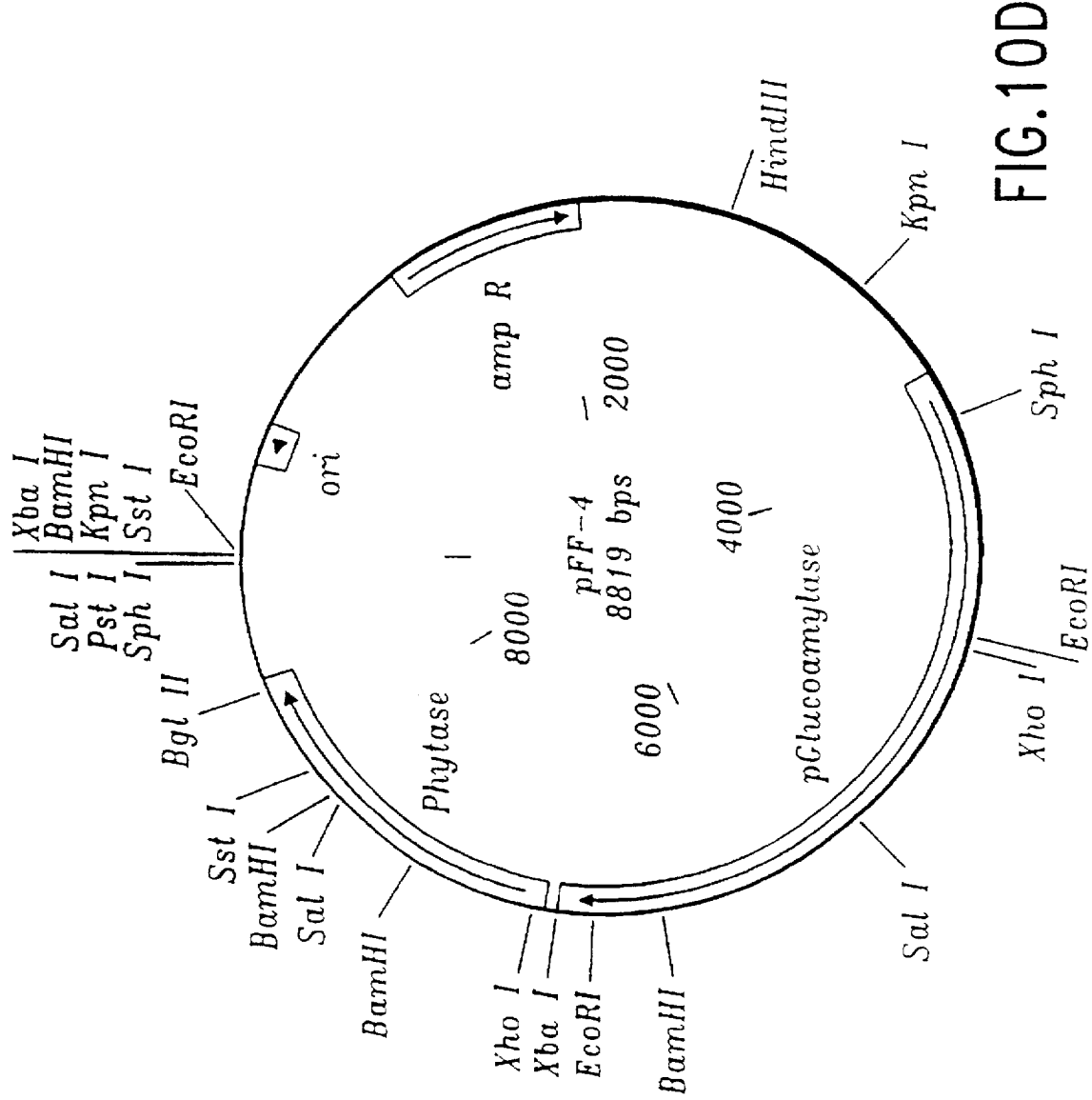

FIG. 11A

```
>Sph1
    v
  1 GCATGCTGGA CCGCAATCTC CGATCGCCGG GTATAAAAGG TCCTCCAAAC CCCTCTCGGT CGATATGTAC CCCGCTCGTC ATCTCCAATC CTCTCGAGAG
101 CACCTTCTCC AGCTTTTGTC AATTGTACCT TCGCCAATGCC CAACCCAGGA GAAGCAGTTC TCGCACCTCT CTCCCTCACC TGGCCTGTGC TCTGGCCACG GGCGCATCCG CTTTCTCTA
                                                                       M  P   R  T  S   L  L  T   L  A  C  A   L  A  T   G  A  S   A  F  S  Y>
201 CGGGGCTGCC ATTCCTCAGT CAACCCAGGA GAAGCAGTTC TCTCAGGAGT TCGGCGATGG CTACAGCATC CTCAAGCACT ACGGTGGTAA CGGACCCTAC
     G  A  A   I  P  Q   S  T  Q  E   K  Q  F   S  Q  E   F  R  D  G   Y  S  I   L  K  H   Y  G  G  N   G  P  Y>
301 TCCGAGCGTG TGTCCTACGG TATCGCTCGC GATCCCCCGA CCAGCTGCGA GGTCGATCAG GTCATCATGG TCAAGCGTCA CGGAGAGCGC TACCCGTCCC
     S  E  R   V  S  Y  G   I  A  R   D  P  P   P  T  S  C  E   V  D  Q   V  I  M   V  K  R  H   G  E  R   Y  P  S>
401 CTTCAGCCGG CAAGGACATC GAAGAGGCCC TGGCCAAGGT CTACAGCATC AACACTACTG AATACAAAGG CGACCTGGCC TTCCTGAACG ACTGGACCTA
     P  S  A  G   K  D  I   E  E  A   L  A  K  V   Y  S  I   N  T  T   E  Y  K  G   D  L  A   F  L  N   D  W  T  Y>
501 CTACGTCCCT AATGAGTGCT ACTACAACGC CGAGACCACC AGCGGCCCCT ACGCCGGGTTT GCTGGACGCG TACAACCATG GCAACGATTA CAAGGCTCGC
     Y  V  P   N  E  C   Y  Y  N  A   E  T  T   S  G  P   Y  A  G  L   L  D  A   Y  N  H   G  N  D  Y   K  A  R>
601 TACGGCCACC TCTGGAACGG TGAGACGGTC GTGCCCTTCT TTTGTAGTGG CTACGGACGT GTCATCGAGA CGGCCCGCAA GTTCGGTGAG GGTTTGTTTG
     Y  G  H   L  W  N  G   E  T  V   V  P  F   F  S  S  G   Y  G  R   V  I  E   T  A  R  K   F  G  E   G  F  F>
701 GCTACAACTA CTCCACCAAC GCTGCCCTCA ACATCATCTC CGAGTCCGAG GTCATGGGCG CGGACAGCCT CACGCCCACC TGTGACACCG ACAACGACCA
     G  Y  N  Y   S  T  N   A  A  L   N  I  I  S   E  S  E   V  M  G   A  D  S  L   T  P  T   C  D  T   D  N  D  Q>
801 GACCACCTGC GACAACCTGA CTTACCAGCT GCCCCAGTTC AAGGTCGCTG CTGCCCGCCT AAACTCCCAG AACCCCGGCA TGAACCTCAC CGCATCTGAT
     T  T  C   D  N  L   T  Y  Q  L   P  Q  F   K  V  A   A  A  R  L   N  S  Q   N  P  G   M  N  L  T   A  S  D>
901 GTCTACAAACC TGATGGGTAT GTGATTACGG TACAATGATT GGCTCAAACC TCCAGCTGAC AGCATCCTAG TTATGGCCTC CTTTGAGCTC AATGCTCGTC
     V  Y  N   L  M>                                                                 V  M  A  S   F  E  L  N   A  R>
```

```
1001 CCTTCTCCAA CTGGATCAAC GCCTTTACCC AGGACGAATG GGTCAGCTTC GGTTACGTTG AGGATTTGAA CTACTACTAC TGCGCTGGGT GAGTTTACCA
      P  F  S  N    W  I  N    A  F  T    Q  D  E  W    V  S  F    G  Y  V  V    E  D  L  N    Y  Y  Y    C  A  G>

1101 TTTGATCCAT TATTGTCTTG GATCAGCTAA CGATCGATAG TCCCGGTGAC AAGAACATGG CTGCTGTGGG CTGCCGTCTAC GCCAAGCCA GTCTCACCCT
                                              >  P  G  D    K  N  M    A  A  V  G    A  V  Y    A  N  A    S  L  T  L>

1201 CCTGAACCAG GGACCCAAGG AAGCCGGCTC CTTGTTCTTC AACTTGTACG TTCTCGGCAG AATCAGAGTC TCACAAAAAG AAACTCTTCA CTAACATATA
      L  N  Q    G  P  K    E  A  G  S    L  F  F    N  F>

1301 GTAGTGCCCA CGACACCAAC ATCACCCCCA TCCTCGCCGC CCTAGGGGTC CTCATCCCCA ACGAGGACCT TCCTCTTGAC CGGGTCGCCT TCGGCAACCC
      A  H    D  T  N    I  T  P  I    L  A  A    L  G  V    L  I  P    N  E  D  L    P  L  D    R  V  A    F  G  N  P>

1401 CTACTCGATC GGCAACATCG TGCCCATGGG TGGCCATCTG ACTCTCAGCTG GGGCTACTCC CCTCCGGGACC GCCCCTCTGG ACGAGGGTAC CTACGTGCGT
      Y  S  I    G  N  I    V  P  M  G    G  H  L    T  I  E    R  L  S  C    Q  A  T    A  L  S    D  E  G  T    Y  V  R>

1501 CTGGTGCTGA ACGAGGCTGT ACTCCCCTTC AACGACTGCA ACGTGTCCTA CCCGCAGTAT CTGAGCTTCT GGTGGAACTA CAACACCACG ACGGAGCTC AACAAGAATC
      L  V  L    N  E  A  V    L  P  F    N  D  C    N  V    S  A  S  Y    P  Q  Y    L  S  F    W  W  N  Y    N  T  T    T  E  L    N  Y  R  S>

1601 TGCCAGACTA CACGACCACC TGCAATGTCT CTGCGTCCTA CCCGCAGTAT CTGAGCTTCT GGTGGAACTA CAACACCACG ACGGAGCTC AACAAGAATC
      L  P  D  Y    T  T  T    C  N  V    S  A  S  Y    P  Q  Y    L  S  F    W  W  N  Y    N  T  T    T  E  L    N  Y  R  S>

1701 TAGCCCTATT GCCTGCCAGG AGGGTGATGC TATGGACTAG GTAGGTCCCG GGATACTTTA ATGATACATG TGTAAATAAT GATAATAGCA TTGGAATGTG GTTTTGTTGT TTGTGTGCAT
      S  P  I    A  C  Q    E  G  D  A    M  D  *>

1801 TAGCCCTATT GCCTGCCAGG AGGGTGATGC TATGGACTAG GTAGGTCCCG GATACTTTA ATGATACATG TGTAAATAAT GATAATAGCA TTGGAATGTG GTTTTGTGT TTGTGTGCAT

1901 AGGCGCTTTG GGGGTGTATT TTTAGGCGTT AGACTTATT ICAATTCGTG TATAATGCGG TCAGTAAATG AATCATCAAT TATTCAAATG CAATGCTGTA

2001 TACGTGAAAC TATTGGGTTA AGAGCGCAGCT ACTAGCTGAC TGCTTGGTTA CTTTCTGTGT ACACCGCATG C
                                                                                    >Sph1
                                                                                       ^
```

FIG.11B

RECOMBINANT CELLS THAT EXPRESS PHYTATE DEGRADING ENZYMES IN DESIRED RATIOS

This application is the U.S. national stage application of International application Ser. No. PCT/US93/07058, filed Jul. 27, 1993, published as WO94/03072 Feb. 17, 1994, which was a continuation-in-part of U.S. application Ser. No. 07/925,401, filed Jul. 31, 1992, now abandoned, and claims the benefit of the filing dates thereof under 35 U.S.C. § 120.

FIELD OF THE INVENTION

This invention is related to strains of filamentous fungi capable of over-expressing at least two phytate degrading enzymes in desired ratios. Also disclosed are DNA sequences, promoters, DNA constructs and vectors useful for the preparation of such strains.

BACKGROUND OF THE INVENTION

Minerals are essential elements for the growth of all organisms. For livestock production of monogastric animals (e.g., pigs, poultry) and fish, feed is commonly supplemented with minerals. Plant seeds are a rich source of minerals since they contain ions that are complexed with the phosphate groups of phytic acid. Ruminants do not require inorganic phosphate and minerals because microorganisms in the rumen produce enzymes that catalyze conversion of phytate (myo-inositol-hexaphosphate) to inositol and inorganic phosphate. In the process minerals that have been complexed with phytate are released.

Phytate occurs as a source of stored phosphorus in virtually all plant feeds (for a review see: Phytic Acid, Chemistry and Applications, E. Graf (Ed.), Pilatus Press: Minneapolis, Minn., U.S.A., 1986). Phytic acid forms a normal part of the seed in cereals and legumes. It functions to bind dietary minerals that are essential to the new plant as it emerges from the seed. When the phosphate groups of phytic acid are removed by the seed enzyme phytase, the ability to bind metal ions is lost and the minerals become available to the plant. In livestock feed grains, the trace minerals bound by phytic acid are only partially available for absorption by monogastric animals, which lack phytase activity. Although some hydrolysis of phytate occurs in the colon, most phytate passes through the gastrointestinal tract of monogastric animals and is excreted in the manure contributing to fecal phosphate pollution problems in areas of intense livestock production. Inorganic phosphorus released in the colon has no nutritional value to livestock because inorganic phosphorus is absorbed only in the small intestine. Thus, a significant amount of the nutritionally important dietary minerals are potentially not available to monogastric animals.

Conversion of phytate to inositol and inorganic phosphorus can be catalyzed by microbial enzymes referred to broadly as phytases. Phytases such as the phytase #EC 3.1.3.8 are capable of catalyzing hydrolysis of myo-Inositol hexaphosphate to D-myo-inositol 1,2,4,5,6-pentaphosphate and orthophosphate. Certain fungal phytases reportedly hydrolyze inositol pentaphosphate to tetra-, tri-, and lower phosphates; e.g., A. ficuum phytases reportedly produce mixtures of myoinositol di- and mono-phosphate (Ullah, 1988). Phytase producing microorganisms comprise bacteria such as Bacillus subtilis (V. K. Powar and V. J. Jagannathan, J. Bacteriol. 151:1102–1108, 1982) and Pseudomonas (D. J. Cosgrove, Austral. J. Biol. Sci. 23:1207–1220, 1970); yeasts such as Saccharomyces cerevisiae (N. R. Nayini and P. Markakis, Lebensmittel Wissenschaft und Technologie 17:24–26, 1984); and fungi such as Aspergillus terreus (K. Yamada, Y. Minoda and S. Yamamoto, Agric. Biol. Chem. 32:1275–1282, 1968). The possible use of microbes capable of producing phytase as a feed additive for monogastric animals has been reported previously (Shieh and Ware, U.S. Pat. No. 3,297,548; Nelson, T. S. et al., J. Nutrition 101:1289–1294, 1971). To date, however, commercial application of this concept has not proved feasible, because of the high cost for production of microbial phytases.

Microbial phytases may also reportedly be useful for producing animal feed from certain industrial processes, e.g., wheat and corn waste products. The wet milling process of corn produces glutens sold as animal feeds. Addition of phytase may reportedly improve the nutritional value of the feed product. Fungal phytase enzymes and process conditions (t~50° C. and pH~5.5) have been reported previously in European Patent Application 0 321 004. In processing soybean meal the presence of phytate reportedly renders the meal and wastes unsuitable for feeds used in rearing fish, poultry and other non-ruminants as well as calves fed on milk. Phytase is reportedly useful for improving the nutrient and commercial value of this high protein soy material (see Finase Enzymes By Alko, a product information brochure published by Alko Ltd., Rajamaki, Finland). A combination of phytase and a pH2.5 optimum acid phosphatase from A. niger has been used by Alko, Ltd. as an animal feed supplement in their phytic acid degradative product Finase F and Finase S. A cost-effective source of phytase would greatly enhance the value of soybean meal as an animal feed (Shieh et al., 1969).

Phytase and less specific acid phosphatases are produced by the fungus Aspergillus ficuum as extracellular enzymes (Shieh et al., 1969). Ullah reportedly purified a phytase from wild-type A. ficuum that had an apparent molecular weight of 61.7 kDa (on SDS-PAGE; as corrected for glycosylation); pH optima at pH2.5 and pH5.5; a Km of about 40 μM; and, a specific activity of about 50 U/mg (Ullah, A., Preparative Biochem. 18:443–458, 1988); PCT patent application WO 91/05053 also reportedly discloses isolation and molecular cloning of a phytase from Aspergillus ficuum with pH optima at pH2.5 and pH5.5, a Km of about 250 μM, and specific activity of about 100 U/mg protein.

Acid phosphatases are enzymes that catalytically hydrolyze a wide variety of phosphate esters and usually exhibit pH optima below 6.0 (Hollander, 1971); e.g., #EC 3.1.3.2 catalyzes hydrolysis of orthophosphoric monoesters to orthophosphate products. An acid phosphatase has reportedly been purified from A. ficuum. The deglycosylated form of the acid phosphatase has an apparent molecular weight of 32.6 kDa (Ullah et al., 1987).

Objects of the invention provide recombinant phosphatases isolated from filamentous fungi that improve the efficiency of release of phosphorus from phytate and the salts of phytic acid. Other objects of the invention provide efficient and inexpensive sources of two or more recombinant enzymes that are suitable for commercial use in feeds and industrial processes with minimal processing.

SUMMARY OF THE INVENTION

Two enzymes were substantially purified from Aspergillus niger var. awamori strain ALKO243: namely, a phytase and a pH2.5 acid phosphatase. The amino acid sequence for isolated internal peptides was determined for each enzyme and the deduced nucleotide sequences were used to construct probes that were used to molecularly clone the two genes. The genomic nucleotide sequence was determined for each gene and the coding region sequence was also determined (where necessary) by cloning the cDNA. Comparison of the deduced amino acid sequences of the phytase and pH2.5 acid phosphatase with other known phosphatases identified a potential enzyme active site sequence. Transformation vectors were constructed using promoters native to filamentous fungi and several different heterologous promoter sequences were compared in their ability to drive expression of the respective genes. Recombinant host cells were selected that over-produced phytase and pH2.5 acid phosphatase at levels that were about 2-fold to about 4000-fold higher, and 10-fold to 126-fold higher (respectively), than the levels of these enzymes secreted by the ALKO243 (ATCC#38854) strain of *Aspergillus*. Dual-gene-transformed host cells were also selected that expressed elevated levels of the two recombinant enzymes, i.e., both phytase and pH2.5 acid phosphatase. Selected strains of dual-gene-transformed cells were identified that synthesized and secreted phytase along with pH2.5 acid phosphatase within desired tailor-made ranges of the respective enzyme activities, e.g., within a range of 3:1 to 16:1 pH2.5 acid phosphatase activity to phytase activity. The transformed recombinant host cells disclosed herein solve the problems in the prior art and provide cost-effective sources of commercial phosphatase enzymes suitable for use in commercial processes that liberate minerals from phytates in plant materials either in vitro, i.e., in feed treatment processes, or in vivo, i.e., by administering one or more of the enzymes to animals.

The phytase purified from *A. niger* var. awamori strain ALKO243 (ATCC#38854; also known as IFO4033) exhibited an apparent molecular weight of 80–86,000 daltons (SDS-PAGE), and 45,000–48,000 daltons (SDS-PAGE), following treatment with endoglycosidase F/N-glycosidase F. The purified phytase appears to be monomeric under non-denaturing conditions with an isoelectric point of approximately 5.3. This phytase enzyme exhibits activity in the absence of metal ions, i.e., metal ion independent; the enzyme has a pH optima of about 5.0; and, a temperature optimum in the range of 55°–60° C.

The purified pH2.5 acid phosphatase from *A. niger* var. awamori strain ALKO243 had an apparent molecular weight of about 66,000 daltons (SDS-PAGE) and 46,000–49,000 daltons (SDS-PAGE) after removal of carbohydrates with endoglycosidase F/N-glycosidase F. This purified pH2.5 acid phosphatase appears to be tetrameric under nondenaturing conditions with an isoelectric point of approximately 4 to 4.25; an apparent Km of 0.7 mM for sodium phytate at pH 2.5 and 4 mM for paranitrophenylphosphate; a pH optima of about pH2.5; and, temperature optimum of about 55° C.

Translated nucleotide sequences for phytase and pH2.5 acid phosphatase yielded polypeptides of 470 amino acids and 479 amino acids, respectively. The calculated molecular weights for the predicted phytase and pH2.5 acid phosphatase polypeptides were approximately 51,400 daltons and approximately 52,700 daltons, respectively.

The desired ratio of recombinant pH2.5 acid phosphatase phytase and phytase produced by a dual-gene-transformed recombinant host cells achieves a balanced enzyme mixture in which cooperative enzyme activity rapidly and effectively catalyzes the near complete hydrolysis of phytate to inositol and free phosphate with release of minerals from the phytic acid complex.

BRIEF DESCRIPTION OF THE DRAWINGS

The foregoing aspects and many of the attendant advantages of this invention will become more readily appreciated as the same becomes better understood by reference to the following detailed description, when taken in conjunction with the accompanying drawings, wherein:

FIG. 9A and FIG. 9B shows the genomic nucleotide sequence (SEQ. ID. NO. 1) for the phytase gene in *Aspergillus niger* var. awamori strain ALKO243 (ATCC#38854); the deduced amino acid sequence (SEQ. ID. NO. 2) for the phytase polypeptide, as described in Example 2, below; and, the 5' regulatory promoter region of the gene;

FIG. 10A, FIG. 10B, FIG. 10C and FIG. 10D show the organization of phytase expression vector constructs pFF1, pFF2, pFF3 and pFF4 (as described in Example 4, below);

FIG. 11A and FIG. 11B shows the nucleotide sequence for the pH2.5 acid phosphatase gene (SEQ. ID. NO. 3) and the deduced amino acid sequence (SEQ. ID. NO. 4) of the enzyme;

FIG. 16 shows chromosomal phytase gene copy number and MRNA levels in phytase gene transformed *A. niger* var. awamori strain ALKO2268 as determined by Southern blot analysis and Northern analysis, respectively (as described in Example 4, below). The significant increase in phytase activity seen in FIG. 15 in transformed cells is attributable to integration of one or more copies of the cloned recombinant phytase gene construct into chromosomal DNA (see Example 4, below);

FIG. 17 and FIG. 18 show chromosomal phytase and pH2.5 acid phosphatase gene copy numbers and mRNA levels in dual-gene-transformed *A. niger* var. awamori strain ALKO243 as determined by Southern blot analysis and by Northern analysis, respectively (as described in Example 5);

DETAILED DESCRIPTION OF THE PREFERRED EMBODIMENT

Figure 1:
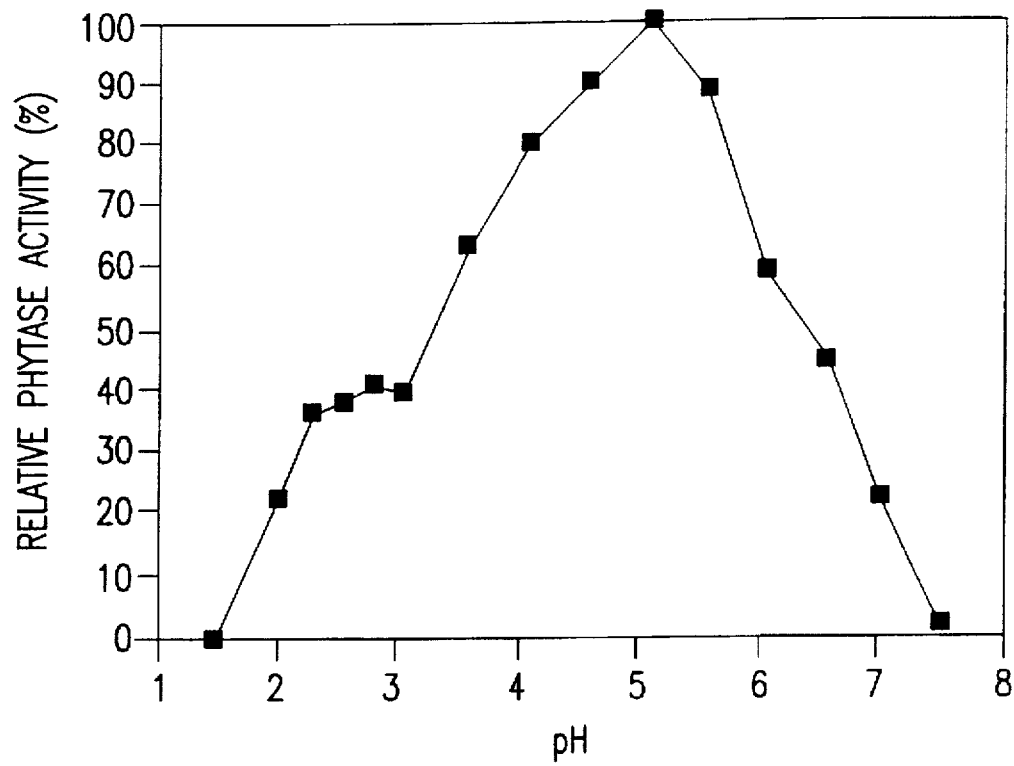
FIG. 1 shows the pH optima of a metal ion independent phytase enzyme purified from *Aspergillus niger* var. awamori strain ALKO243 (ATCC#38854) with a pH optima of about pH5; and, >20% maximal enzyme activity in the range of pH2 to pH7 (as described in Example 1, below)

As used herein the following terms are intended to mean as follows:

The term "phosphatase" is intended to mean an enzyme capable of releasing phosphate from a phosphate-containing substrate, e.g., phytate. Representative examples of phosphatases include fungal phytases and acid- and neutral-phosphatases such as pH2.5 acid phosphatase and pH6 neutral phosphatase.

The term "nucleic acid" is used herein to refer to natural or synthetic DNA and RNA, polynucleotides (i.e., greater than three nucleotides), and oligonucleotides (i.e., greater than nine nucleotides).

The term "capable of hybridizing under stringent conditions" is used herein to mean annealing to a subject nucleotide sequence, or its complementary strand, under standard conditions, e.g., high temperature and/or low salt content which tends to disfavor annealing of unrelated sequences. A suitable protocol (involving 0.1×SSC and annealing at 68° C. for 2 hours) is described in Maniatis, T. et al., *Molecular Cloning: A Laboratory Manual*, Cold Springs Harbor Laboratory, Cold Springs Harbor, N.Y., pp. 387–389, 1982.

The term "nucleotide sequence" is used herein to refer to a sequence of nucleotides or nucleosides and may include non-contiguous sequences; e.g., in genomic sequences exon coding region sequences may be interrupted by intron sequences and the like.

The term "contiguous nucleotide sequence" is used herein to refer to a sequence of nucleotides linked in a serial array, one following the other.

The term "coding region" refers to the nucleotide sequence within a nucleic acid that when transcribed and translated will give rise to a subject amino acid sequence, e.g., exon regions in genomic DNA that when transcribed into mRNA will direct translation of the subject amino acid sequence. The term "encoded" is used to mean an amino acid sequence coded for in the triplet code of nucleotides by the coding region nucleotide sequence.

The term "transformation vector" is used herein interchangeably with "vector construct" to refer to a recombinant construct (e.g., a plasmid DNA) containing a subject phytase, and/or pH2.5 acid phosphatase nucleotide sequence incorporated therein, and includes as one subclass "expression vectors". Representative examples of transformation vectors include plasmid vectors of *E. coli* (e.g., pBR322, pUC18, pUC19 and the like as well as vectors useful for transforming filamentous strains of fungi (e.g., pLO-3, pFF-6, pPHO-1 and the like). The subject phytase or pH2.5 acid phosphatase nucleotide sequence may contain the regulatory sequence elements from the 5' region of the respective gene (i.e., termed herein "native regulatory elements"); or, a heterologous promoter (i.e., from a strain, variety, species or genus other than *A. niger* var. awamori strain ALKO243 or from a different gene, e.g., GA or GAPDH promoter nucleotide sequences) may be added to drive expression of the subject nucleotide sequence. The subject transformation vector may also contain suitable restriction sites for receiving additional nucleotide sequences useful for promoting chromosomal integration of the vector DNA. The subject transformation vectors are capable of introducing phosphatase nucleotide sequences into a host cell so that they may integrate effectively into the host cell DNA, and so that the product of the coding region of the nucleotide sequence is expressed by the transformed host cell.

"Promoter" is used to mean a nucleotide sequence capable of promoting expression of a downstream nucleotide sequence such as transcription and translational regulatory signal sequences and the like. Representative examples of promoters are provided below in Examples 3–5, e.g., GA, GAPHD, and native phytase or pH2.5 acid phosphatase promoter.

"Selectable marker" is used to mean a nucleotide sequence capable of encoding a polypeptide that when expressed by transformed cell confers upon the cell the ability to be identified or selected from among the other cells in a population of cells. Illustrative examples include antigenic markers, phenotypic markers (e.g., cell size, shape, budding patterns and the like), and drug resistance markers such as phleomycin resistance.

As used herein the term "transformed recombinant host cell" refers to a cell having chromosomal DNA with an integrated transformation vector nucleotide sequence therein. Representative examples of transformed recombinant host cells of the invention include bacterial and fungal cells capable of synthesizing and/or secreting a recombinant phytase and/or one or more recombinant phosphatases, i.e., a phytase encoded by a nucleotide sequence capable of hybridizing under stringent conditions with SEQ. ID. NO. 1; and, the recombinant pH2.5 acid phosphatase, i.e., a phosphatase encoded by a nucleotide sequence capable of hybridizing with SEQ. ID. NO. 3.

The term "phytase nucleotide sequence" as used herein refers to the nucleotide sequence located within SEQ. ID. NO. 1.

The term "pH2.5 acid phosphatase nucleotide sequence" as used herein refers to a nucleotide sequence capable of hybridizing under stringent conditions with a nucleotide sequence in SEQ. ID. NO. 3.

The term "phosphatase" as used herein encompasses all enzymes capable of cleaving a phosphate ester bond in a substrate, and includes phytases, and acid and neutral phosphatases.

The term "phytase" is intended to mean an enzyme capable of hydrolyzing a phosphate ester bond in a phytate substrate, e.g., inositolhexaphosphate, inositolpentaphosphate, inositoltetraphosphate, and inositoltriphosphate and salts thereof The term "purified phytase" is intended to mean a purified enzyme of the invention isolated and substantially purified from A. niger var. awamori strain ALKO243. The subject enzymes are monomeric under nondenaturing conditions with isoelectric points of about 5.3; apparent molecular weights on SDS-PAGE of about 80,000 daltons to 86,000 daltons, apparent molecular weights after removal of carbohydrate (e.g., with endoglycosidase F/N-glycosidase F) of about 45,000–48,000 daltons (SDS-PAGE). The subject purified phytase enzymes have the following catalytic properties: namely, the enzymes are metal ion-independent enzymes capable of hydrolyzing a phosphate ester bond in a sodium phytate substrate. The subject enzymes have a pH optima of about pH5 at 37° C.; exhibit greater than 20% of maximal enzyme activity in the range of pH2 to pH7; and, have a temperature optima at 55° C. to 60° C. with >20% maximal enzyme activity in the range of 25° C. to 65° C. One unit of phytase activity (PU) is the amount of enzyme protein required to liberate 1 nmol of inorganic phosphate from sodium phytate in one minute at 37° C. under the assay conditions described in Example 1, below.

Figure 9A:
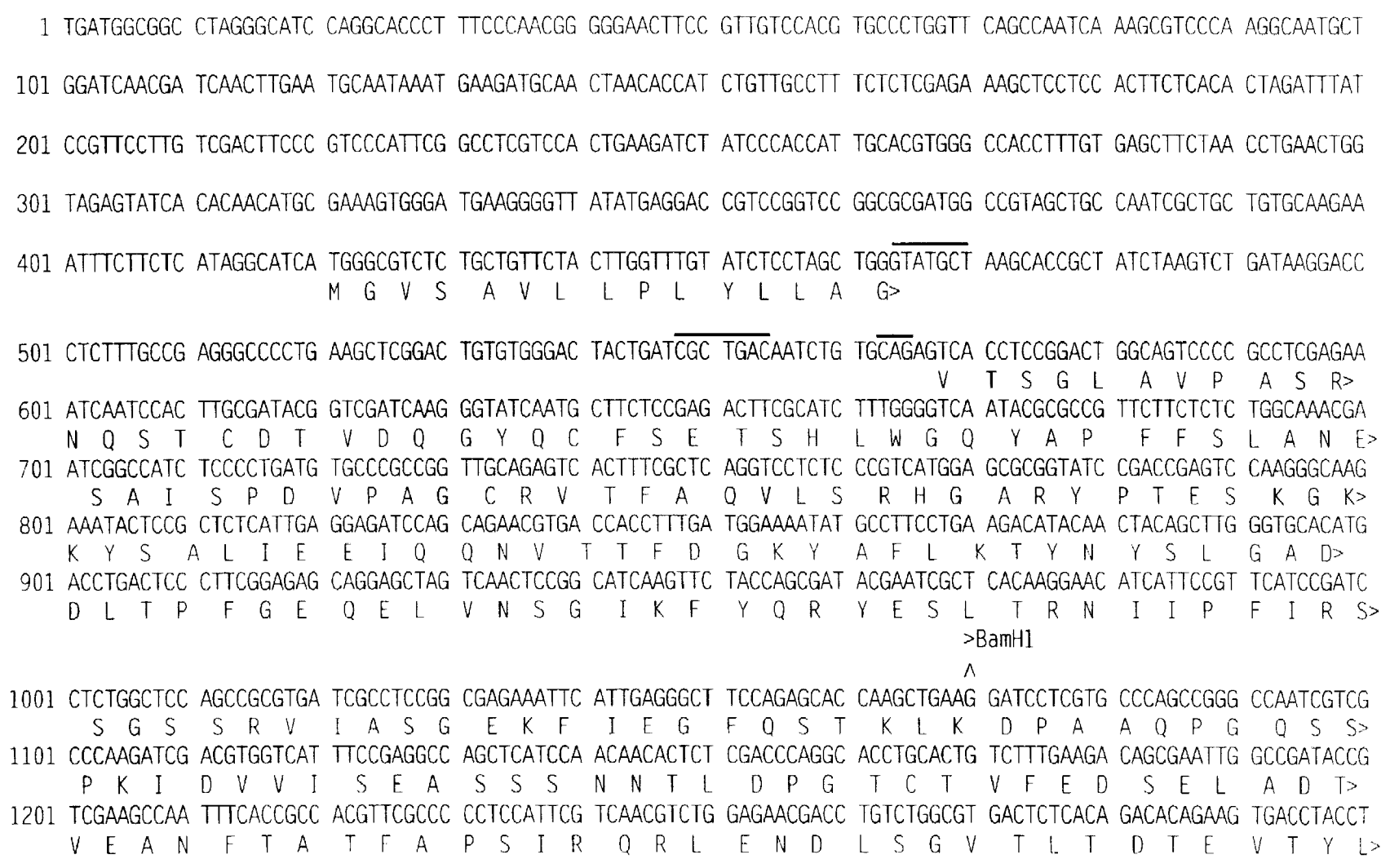

The term "recombinant phytase" is intended to mean a phytase enzyme encoded by the nucleotide coding sequence of FIGS. 9A and 9B; SEQ. ID. NO. 1 and produced by a recombinant host cell transformed with the subject transformation vector containing the subject phytase nucleotide sequence. The molecular weight predicted from transcription of the coding region of subject phytase nucleotide sequence is a polypeptide translation product (i.e., prior to glycosylation) of about 51,000 daltons to about 52,000 daltons.

The term "metal ion independent" is intended to mean that the activity of the enzyme can be measured in the absence of $Mn^{2+}$, $Mg^{2+}$ and $Ca^{2+}$. However, this is not intended to mean that the activity of the enzyme may not be increased in the presence $Mn^{2+}$, $Mg^{2+}$ or $Ca^{2+}$.

The term "acid phosphatase" is used to mean an enzyme having a pH optimum for mediating hydrolysis of a phosphate ester bond in a substrate at a pH less than pH5.0, preferably less than pH3.0.

The term "pH2.5 acid phosphatase" is used to refer to a phosphatase having a pH optimum for mediating hydrolysis of a phosphate ester in a substrate at pH2.0–2.5, e.g., a sodium phytate substrate.

The term "purified pH2.5 acid phosphatase" is intended to mean a purified enzyme of the invention isolated and substantially purified from A. niger var. awamori strain ALKO243. When purified from the subject strain of filamentous fungi the enzyme has the following properties: namely, the enzyme isolated under nondenaturing conditions is a glycoprotein tetrameric complex of four identical monomers with an apparent isoelectric point of about 4.0 to about 4.25. Each of the monomers has an apparent molecular weight of about 66,000 daltons under denaturing conditions in SDS-PAGE, and the monomers have an apparent molecular weight of 46,000–49,000 daltons (SDS-PAGE) after substantial removal of carbohydrate. The subject purified pH2.5 acid phosphatase enzymes have the following catalytic properties: namely, the enzymes can catalyze hydrolysis of a phosphate ester bond in a sodium phytate substrate with an apparent Km of about 0.7 mM (i.e., at 37° C. and pH2.5, as described in Example 1, below). The subject enzymes have a pH optima of about pH2 to about pH2.5 (i.e., at 37° C.); have greater than 20% of maximal enzyme activity in the range of pH1.5 to pH3.5; and, have a temperature optima at 55° C. with >20% maximal enzyme activity in the range of 25° C. to 60° C. One unit of pH2.5 acid phosphatase activity (HFU) is the amount of enzyme protein required to liberate 1 nmol of inorganic phosphate from p-nitrophenyl phosphate in one minute at 37° C. under the conditions described in Example 1, below.

The term "recombinant pH2.5 acid phosphatase" is intended to mean a pH2.5 acid phosphatase enzyme encoded by the coding region of a nucleotide sequence capable of hybridizing under stringent conditions with a nucleotide sequence in FIGS. 11A and 11B; (SEQ. ID. NO. 3 ) and produced by a recombinant host cell transformed with the subject transformation vector containing the subject pH2.5 acid phosphatase nucleotide sequence. In a representative example, the subject pH2.5 acid phosphatase nucleotide sequence is the coding region of SEQ. ID. NO. 3 that encodes a polypeptide with an apparent molecular weight (i.e., prior to glycosylation) of about 52,000 daltons to about 53,000 daltons.

The term "secreted" is used herein to refer to the extracellular form of a protein, e.g., a "secreted" protein that is synthesized in a cell and transported into the extracellular culture medium where its presence or enzyme activity may be assayed.

The term "phytase enzyme activity" is used herein to refer to the catalytic activity of a phytase, e.g., in mediating hydrolysis of a sodium phytate substrate to release phosphate, as may be conveniently measured in an assay for phosphate such as that described in the Examples, below.

The term "pH2.5 acid phosphatase enzyme activity" is used herein to refer to the phosphatase activity of a pH2.5 acid phosphatase, e.g., in mediating hydrolysis of a phosphate ester bond in a paranitrophenylphosphate substrate (in an assay such as that described in the Examples, below).

The term "over-producing" is used interchangeably with the term "over-expressing" to indicate that the subject transformed recombinant host cell is capable of synthesizing and secreting levels of the subject enzyme that are at least about 2-fold higher than the amount of enzyme synthesized under identical conditions by cells of A. niger var. awamori strain ALKO243 (ATCC#38854). As illustrated in Example 4, (Tables 8 and 9, below), over-production in strain ALKO2268 results in secretion in skake flask cultures conducted according to Example 1 of about 45-fold more phytase enzyme activity per ml of the culture media than that secreted under equivalent conditions by ALKO243. Illustrative transformants with the subject nucleic acids of the invention (i.e., also shown in Example 4) produce about 6-fold greater activity than ALKO2268 (i.e., see Table 7; up to about 300-fold greater activity than ALKO243). Other transformants in Example 4 (i.e., Tables 8 and 9) produced phytase activities per ml up to about 2,100-fold greater than ALKO243. Over-production in respect to pH2.5 acid phosphatase is similarly illustrated by transformants in Example 4, below, that produced up to about 130-fold (i.e., Table 11) greater activity per ml than ALKO243. By comparison, strain ALKO2268 produces approximately 41–46% of the pH2.5 acid phosphatase enzyme activity produced by ALKO243.

The term "ratio of pH2.5 acid phosphatase to phytase" refers to the ratio of a pH2.5 acid phosphatase enzyme activity to a phytase activity, in this case, a ratio that may becalculated by dividing the enzyme activity of pH2.5 acid phosphatase per ml of sample (e.g., the number of HFU/ml) by the phytase enzyme activity per ml of sample (e.g., the number of PU/ml). Representative assays for determining phytase and pH2.5 acid phosphatase activity are provided in the Examples, below. For comparative purposes, the results presented in the Examples below show the amount of phytase and pH2.5 acid phosphatase activity, respectively, produced and secreted into the culture broth by *A. niger* var. awamori strain ALKO243 (ATCC#38854) over 5 days of fermentation culture under the conditions described in Tables 7 and 8, below (Example 3). Cells of ALKO243 cultured under these conditions produce about 80–450 PU of phytase and about 5,000–6,000 HFU of pH2.5 acid phosphatase; and, for reference purposes, the over-producer phytase strain *A. niger* var. awamori strain ALKO2268 produces about 3,000–9,000 PU and 2,000–3000 HFU. With these exemplary strains the ratio of pH2.5 acid phosphatase to phytase (i.e., HFU/PU) is about 0.6 in shake flask fermentation culture media obtained from ALKO2268 after 5 days, and is 64.7 with ALKO243, (e.g., see Tables 11 and 14–16, below). As illustrated in Example 5, below, ratios of pH2.5 acid phosphatase activity (HFU) to phytase activity (PU) ranged from about 4 to about 16 with transformants shown in Table 14, and about 3 to 6 with the transformants whose enzymes activities are shown in Tables 15 (PU) and Table 16 (HFU). The subject "ratio of pH2.5 acid phosphatase to phytase" achieves a balanced enzyme mixture in which cooperative enzyme activity rapidly and effectively catalyzes the near complete hydrolysis of phytate to inositol and free phosphate with release of minerals from the phytic acid complex at a pH (e.g., that in the stomach of a monogastric animal) and temperature desired in a commercial product. The term "cooperative enzyme activity" is used to mean that the subject ratios confer upon the mixture of enzymes the properties of: a) more rapid catalysis of phytate to inositol and free phosphate; b) more efficient conversion of phytate to inositol and free phosphate; and, c) more complete conversion of phytate (i.e., IP6, see the Examples below) to inositol and phosphate (i.e., greater than 80% conversion as illustrated in Example 1, Table 1, below).

One "phytase normalized unit" or "PNU" is defined as the amount of phytase activity produced by the *A. niger* ALKO243, which in this case is equivalent to 85 PU/ml. One "acid phosphatase normalized unit" or "APNU" is defined as the amount of acid phosphatase activity produced by the *A. niger* ALKO243 strain, which in this case is equivalent to 5500 HFU/ml.

Embodiments of the invention provide phytase nucleotide sequences capable of hybridizing under stringent conditions with a nucleotide sequence of SEQ. ID. NO 1. The invention also provides pH2.5 acid phosphate nucleotide sequences capable of hybridizing under strigent conditions with a nucleotide sequence of SEQ. ID. NOS. 6 or 9. The subject nucleotide sequences are useful for constructing oligonucleotide probes, transformation vectors, transformed recombinant host cells, encoding recombinant phytase and pH2.5 acid phosphatase proteins, and the like, as described below.

In other embodiments the invention provides transformed recombinant host cells, e.g., *E. coli, Bacillus, Aspergillus, Trichoderma, Penicillium, Cephalosporium, Rhizopus*, and the like, that have copies of the subject phytase and/or pH2.5 acid phosphatase nucleotide sequences of the invention. In a preferred embodiment the transformed recombinant host cells are selected from among species of filamentous fungi, e.g., *Aspergillus, Trichoderma,* and *Rhizopus*; and, in another preferred embodiment the subject host cells are selected from among varieties and strains of *Aspergillus niger*. In a most preferred embodiment the subject host cells are selected from among recombinant host cells having phytase nucleotide sequences, e.g., transformed cells of the phytase over-producing strains GAI-6, GAL-142, GAN-1, GAG-12, GAO-248, GAI-12, GAK4–46, GAI-2, GAK4–52, GAM-111, GAK4–47, GAM-225, GAD-103, GAD-23, GAD-103, GAD-23, GAD-130, GAM-199, GAE-3, GAE-32, GAM-111, and GAL-65 (as described in Example 4, below). In another preferredembodiment the subject host cells are selected from among recombinant host cells transformed with vectors having pH2.5 acid phosphatase nucleotide sequences, e.g., transformed cells of strains GAO-69, GAW-131, GBL-128, GBL-97, GAO-61, GAW-89, GAW-130, GAW-121, GBL-87, GBL-119, GAO-84, GAW-54, GBL-129, GAW-141, GBL-103, GAW-112, GBL-92, GAW-114, and GAT-143 (as described in Example 2, 4, 5, or 6 below). Other preferred host cells include cells selected from the transformed strains GAX-11, GAX-12, GBE-14, GBH-134, GBH-15, GBJ-9, GBJ-10, GBJ-13, GBJ-16, GBJ-26, GBJ-27, GBJ-28, GBJ-31, GBJ-35, GBJ-38, GBJ-40, GBJ-76, and GBJ-82 (as described below in Example 2, 4, 5, or 6). Those skilled in the art will recognize that the nucleotide sequences, transformation vectors and transformed recombinant host cells provided herein are useful for identifying additional strains having substantially the same properties as the afore-identified strains.

Skilled artisans will recognize that the nucleotide sequences and deduced amino acid sequences of the invention may be useful in constructing nucleotide and antibody probes for identifying and isolating natural variants, and mutants of transformants, e.g., mutants resulting from treatment with chemicals, UV, gamma-irradiation and the like). Mutants may have increased expression of the subject phytase, pH2.5 acid phosphatase, or both a phytase and a pH2.5 acid phosphatase. Representative screening assay for identifying the latter mutants include Northern and Southern blotting, and Western blotting with antibodies directed to peptides (natural and synthetic) within the deduced amino acid sequences of the subject phytases and pH2.5 acid phosphatases.

Those skilled in the art will of course recognize that mixtures of transformed recombinant host cells may be used to achieve production of a phytase and one or more phosphatases; e.g., transformed recombinant host cells from a strain producing phytase may be mixed with transformed recombinant host cells from a strain producing pH2.5 acid phosphatase. In this manner, the mixed cell cultures may be constructed so that the cells release a desired ratio of phytase enzyme activity to pH2.5 acid phosphatase enzyme activity.

The subject transformed recombinant host cells of the invention may also be used for preparing substantially pure recombinant phytase preparations. In a preferred embodiment phytase nucleotide sequences in the transformed recombinant host cell encode a polypeptide having a phytase amino acid sequence RHGXRXP SEQ. ID. NO. 5, wherein R is arginine, H is histidine, G is glycine, X is any amino acid, and P is proline.

Embodiments of the invention also provide "mixtures" of recombinant phytase and pH2.5 acid phosphatase in varying states of purity and formulated in a desired ratio of substantially pure pH2.5 acid phosphatase to phytase enzyme activity. Formulating such a balanced mixture of enzymes in the desired ratios confers upon the mixture the property of cooperative enzyme activity (described above) that can be tailor-made to encompass the range of properties desired in a selected commercial application (e.g., uses such as those described below). Starting material for the recombinant phytase and recombinant pH2.5 acid phosphate include fermentation broths, production culture media, and the like from transformed recombinant host cells or from selected strains that over-produce the subject phytase and/or pH2.5 acid phosphatase. Down-stream processing of the subject enzymes into a product may involve removal of cells and cellular debris (e.g., by centrifugation, filtration and the like), followed by concentration (e.g., by ultrafiltration, ion exchange or affinity chromatography and the like), or the starting material may be suitable for use in commercial processes after a simple purification (e.g., lyophilization). The subject mixtures may be prepared by combining equal (or different) amounts of the subject enzyme preparations (e.g., from different cell cultures), in order to achieve the desired ratio of the respective enzyme activities, or the subject mixtures may be existent in the same culture (e.g., the product of a dual-gene-transformed recombinant host cell, as described below). In a preferred embodiment the subject mixture contains a ratio of a phosphatase enzyme activity (e.g., pH2.5 acid phosphatase) to a phytase enzyme activity that is about 3:1 to about 16:1.

Embodiments of the invention provide transformed recombinant host cells that are constructed with one or more transformation vectors having a phytase nucleotide sequence and one or more phosphatases, i.e., a pH2.5 acid phosphatase nucleotide sequence, wherein expression of each enzyme under the control of an independent promoter sequence. The subject transformed host cells are selected for expression of the two (or more) protein products within a desired range of enzyme activities.

The phosphatases produced by the transformed recombinant host cells and processes that are embodiments of the invention provide the following advantages over other enzyme preparations used previously in the art: namely, the subject phosphatases of the invention have higher enzyme activity per unit volume of sample, greater yield of enzyme protein per unit volume of sample, greater cost-efficiency, less concentration and/or purification required for use in a commercial product or process, greater efficacy in converting phytate to free inositol and inorganic phosphate, and fewer digestive side-effects when used in animal feeds.

The subject phosphatases produced by the transformed recombinant host cells of the invention are useful in commercial processes for releasing minerals from complexes with phytate in plant materials such as seeds and waste matter of milling, e.g., soybean meal, so that low value materials are converted efficiently and effectively to a high quality feed for non-ruminant animals. Examples of commercial processes in which the subject enzymes may be useful include corn wet milling, plant protein isolation (especially soy protein isolation), cereal treatment for use in baking, and the like.

In a preferred embodiment the subject phosphatases of the invention are added directly to animal feeds so that phosphates are ingested by the animal and released in vivo in the digestive tract, e.g., of a non-ruminant animal. In this case the subject phosphatases are selected to have pH optima for their respective enzyme activities that coincide with the digestive pH encountered in a non-ruminant animal (i.e., the range of pH1 to pH6).

Suitable methods for preparing the subject enzymes for use in products include spray drying, stabilization in liquid formulations, granulation, and encapsulation, which are known to those skilled in the art.

The subject phosphatase enzymes of the invention, and subject mixtures of enzymes, are capable of degrading phytate to free phosphate more efficiently and rapidly than any one of the constituent enzymes alone. Embodiments of the invention provide a mixture of a phytase and a pH2.5 acid phosphatase that is capable of degrading inositolphosphates of phytates and phytic acids, inositolhexaphosphate, IP6; inositolpentaphosphate, IP5; inositol-tetraphosphate, IP4; inositoltriphosphate, IP3, inositol diphosphate, IP2; inositol monophosphate, IP1; to free inositol and inorganic phosphate. The subject mixture provides cooperative enzyme activities by constructing an enzymatic cascade for more rapid, complete, and efficient conversion of a phytate substrate to inorganic phosphate and inositol. For example, a phytase having phytate (IP6) as a preferred substrate may catalyze efficient hydrolysis of IP6 to IP5, IP4, IP3, and IP2 but not to free inositol and inorganic phosphate. In turn, a pH2.5 acid phosphatase may prefer simple phosphate substrates (e.g., IP5, IP4, IP3, IP2 and IP1) and may catalyze efficient hydrolysis of these substrates to free inositol and inorganic phosphates. It is believed that by formulating the subject phosphatase of the invention within desired optimum ranges of phytase to pH2.5 acid phosphatase activity the subject mixtures of the invention provide balanced enzyme mixtures having cooperative enzyme activity. The subject mixtures of the invention formulated in this manner may provide more rapid, efficient and complete release of greater amounts of free inositol and inorganic phosphate from phytate and phytic acid than produced in the same time (and under the same conditions of pH and temperature) by either of the constituent phosphatase enzymes.

EXAMPLE 1

Purification And Amino Acid Sequencing Of Phosphatases Phytase And Acid-Phosphatase Peptides

[General materials and methods are described in the section entitled "Materials and Methods", which follows at the end of this and each subsequent Example.]

Purification of phytase and pH2.5 acid phosphatase:

Phytase and pH2.5 acid phosphatase enzymes were purified at 4°–8° C. (unless otherwise stated) from the cell-free culture medium filtrate/concentrate of A. niger var. awamori strain ALKO243 (ATCC#38854). The culture filtrate/concentrate (990 ml) was adjusted (on ice) to 70% saturation in ammonium sulfate, and the precipitate was removed by centrifugation at 10,000×g for 15 min. The supernatant (1070 ml) was next separated by hydrophobic chromatography on Octyl-Sepharose CL-4B (Pharmacia). The column (5 cm×17 cm) was equilibrated in a 20 mM bis-Tris/HCl buffer, pH6.2, containing 0.436 g $(NH_4)_2SO_4$ per ml; supernant was applied; and, non-adsorbed proteins were removed by washing with 500 ml of the equilibration buffer solution. Adsorbed proteins were eluted from the column using a 500 ml linear gradient from 70% to 0.0% of ammonium sulfate in 20 mM bis-Tris/HCl buffer, pH6.2. Ten ml fractions were collected and analyzed for phytase and pH2.5 acid phosphatase enzyme activity. Most phytase activity eluted early in the gradient. Fractions containing the respective different enzyme activities were pooled separately; concentrated by ultrafiltration on Amicon PM10 membrane filters. Phytase containing fractions were desalted by passage over PD10 (Pharmacia) gel filtration columns equilibrated in 50 mM bis-Tris/HCl, pH6.2 buffer. Phytase purification is described first, followed by acid phosphatase purification.

Phytase was purified first by anion exchange chromatography on DEAE-Sepharose (Pharmacia). Briefly, a 24.5 ml aliquot was applied to a 5 cm×7 cm column equilibrated in 50 mM bis-Tris/HCl, pH6.2. Non-adsorbed proteins were removed by washing with the equilibration buffer (100 ml), and adsorbed proteins were eluted using a linear 200 ml gradient from 0.0M to 0.5M NaCl, in equilibration buffer. The fractions were assayed for phytase activity and fractions with activity were pooled and concentrated to 600 μl using a Centricon-30 miniconcentrator. Portions of 100 μl were applied at about 23° C. to a Superose 12 HR 10/30 HPLC column (Pharmacia) and proteins were eluted with 50 mM bis-Tris/HCl, pH6.2 at a flow rate of 0.3 ml/min. The active fractions were identified, pooled, and concentrated and transferred into 50 mM sodium formate buffer, pH3.8 using a Centricon-30 microconcentrator. The enzyme solution in formate buffer was purified further using cation exchange chromatography. Samples of enzyme were applied in 2 ml aliquots to a Mono S HR 5/5 FPLC column (Pharmacia) equilibrated in 50 mM sodium formate (pH3.8) at about 23° C. The column was washed with the equilibration buffer (10 ml) and the bound protein was eluted at 60 ml/hr. using a 20 ml linear gradient from 0 mM to 430 mM NaCl in the formate equilibration buffer. Phytase was purified by this method with a yield of 18.4% that had a specific activity of approximately 275,900 (PU/mg) with a calculated purification of 130-fold (Table A).

TABLE A

Summary of purification of phytase

| Step | Total Activity (PU) | Total Protein (mg) | Specific Activity (PU/ml) | Yield (%) | Purification (fold) |
|---|---|---|---|---|---|
| Culture filtrate | 4,486,680 | 2,119 | 2,117 | 100 | 1 |
| Ammonium sulphate supernatant | 3,771,750 | 1,263 | 2,986 | 84.1 | 1.4 |
| Octyl Sepharose | 1,765,881 | 32.3 | 54,671 | 39.4 | 26 |
| DEAE-Sepharose | 1,453,470 | 8.4 | 173,032 | 32.4 | 82 |
| Superose 12 | 1,010,888 | 5.7 | 177,349 | 22.5 | 84 |
| Mono S | 827,566 | 3.0 | 275,885 | 18.4 | 130 |

Acid phosphatase containing fractions from the pooled Octyl-Sepharose fraction, above, were first concentrated by ultrafiltration on Amicon PMI 10 filter, and then subjected to molecular-sieve chromatography on a 2.6 cm×94 cm Sephacryl S-200 (Pharmacia) column equilibrated in 50 mM bis-Tris/HCl (pH6.2). Proteins were eluted at 20 ml/hr and fractions with activity were pooled and separated further by anion exchange chromatography on a 5 cm×7 cm DEAE-Sepharose (Pharmacia) column equilibrated in 50 mM bis-Tris/HCl, pH6.2. The column was washed with 100 ml of equilibration buffer and adsorbed proteins were eluted using a 200 ml linear gradient from 0.0M to 0.5M NaCl in equilibration buffer. Pooled active fractions were then concentrated; transferred to 20 mM bis-Tris/HCl, pH6.0 by ultrafiltration on an Amicon PM10 membrane; and, subjected to a second step of anion exchange chromatography, this time using a Mono Q HR 5/5 HPLC column (Pharmacia) equilibrated in 20 mM bis-Tris/HCl, pH6.0 at about 23° C. The sample was applied in 3.5 ml aliquots; the column was washed with 10 ml of the equilibration buffer; and, the proteins were eluted at 60 ml/hr using a 20 ml linear gradient from 0.0 mM to 350 mM NaCl in the equilibration buffer. Fractions containing enzyme activity were pooled, concentrated to a total volume of 400 μl, and transferred into 20 mM bis-Tris/HCl, pH6.2 containing 150 mM NaCl using a Centricon-30 microconcentrator. Additional purification was accomplished, first by molecular-sieve chromatography on a Superose 12 HR 10/30 HPLC column (Pharmacia) equilibrated in the bis-Tris/HCl sample buffer. Aliquots of 100 μl were applied to this column and proteins were eluted at 23° C. at a rate of 18 ml/hr. Fractions contain enzyme activity were pooled, transferred into 20 mM histidine/HCl, pH5.8 buffer using a PD10 gel filtration column, and subjected to a second step of purification by anion exchange chromatography on a Mono Q HR 5/5 HPLC column. Aliquots of 1 ml were applied to the column, the column was washed with 5 ml of the histidine/HCl sample buffer at about 23° C. Proteins were eluted at a rate of 60 ml/hr using a linear 20 ml gradient from 0 mM to 350 mM NaCl in equilibration buffer. The pH2.5 acid phosphatase was purified by this method at 13% yield with a 126-fold purification, Table B.

TABLE B

Summary of purification of pH 2.5 Phosphatase

| Step | Total Activity (HFU) | Total Protein (mg) | Specific Activity (HFU/mg) | Yield (%) | Purification (fold) |
|---|---|---|---|---|---|
| Culture filtrate | 116,523,000 | 2,119 | 54,990 | 100 | 1 |
| Ammonium sulphate supernatant | 88,275,000 | 1,263 | 69,893 | 75.8 | 1.3 |
| Octyl Sepharose | 68,296,470 | 583 | 117,147 | 58.6 | 2.1 |
| Sephacryl | 52,237,600 | 97.9 | 533,581 | 44.8 | 9.7 |
| DEAE-Sepharose | 46,127,692 | 54.6 | 844,830 | 39.6 | 15.4 |
| Mono Q | 19,326,753 | 3.28 | 5,892,303 | 16.6 | 107 |
| Superose | 16,876,978 | nd | nd | 14.5 | nd |
| Mono Q | 15,197,050 | 2.2 | 6,907,750 | 13.0 | 126 | nd = not determined

Phytase: Phytase as purified by the methods recited (above) exhibited an apparent molecular weight on SDS-PAGE of approximately 80,000–86,000 daltons. The protein assubstantially purified (i.e., on SDS-PAGE) gave a positive reaction with periodic acid Schiff staining for carbohydrate (i.e., the purified phytase enzyme is a glycoprotein). After treating the purified phytase with a mixture of endoglycosidase F/N-glycosidase F the apparent molecular weight of the enzyme (on SDS-PAGE) was shifted to about 45,000–48,000 daltons, suggesting that about 44% of the molecular mass may be attributable to carbohydrate. (The type of carbohydrate linkage and the nature of the moiety was not determined.) The molecular weight of the undenatured purified phytase enzyme was shown to be approximately 90,000 daltons by molecular-sieve gel filtration (i.e., based on its Stokes radius), and an apparent molecular weight of 100,000 daltons was observed by native gradient gel PAA electrophoresis. The latter results suggest that the undenatured purified phytase enzyme exists as a monomer. The isoelectric point of the subject phytase is 5.3 by isoelectric focusing.

pH2.5 acid phosphatase: pH2.5 acid phosphatase, purified by the methods recited above, exhibited an apparent subunit molecular weight on SDS-PAGE of 66,000 daltons. The substantially purified enzyme (i.e., on SDS-PAGE) gave a positive reaction with periodic acid Schiff staining indicating that pH2.5 acid phosphatase is also a glycoprotein. After removing carbohydrate with endoglycosidase F/N-glycosidase F the protein exhibited an apparent molecular weight of 46,000–49,000 daltons by SDS-PAGE. (The glycosidic linkage and nature of the carbohydrate moiety was not characterized.) pH2.5 acid phosphatase exhibits an apparent molecular weight of 280,000 daltons by native gradient PAA gel electrophoresis, suggesting that the purified undenatured enzyme exists as a tetramer of four 66,000-dalton subunits. The isoelectric point of acid phosphatase by isoelectric focusing is approximately 4 to 4.25.

Figure 2:
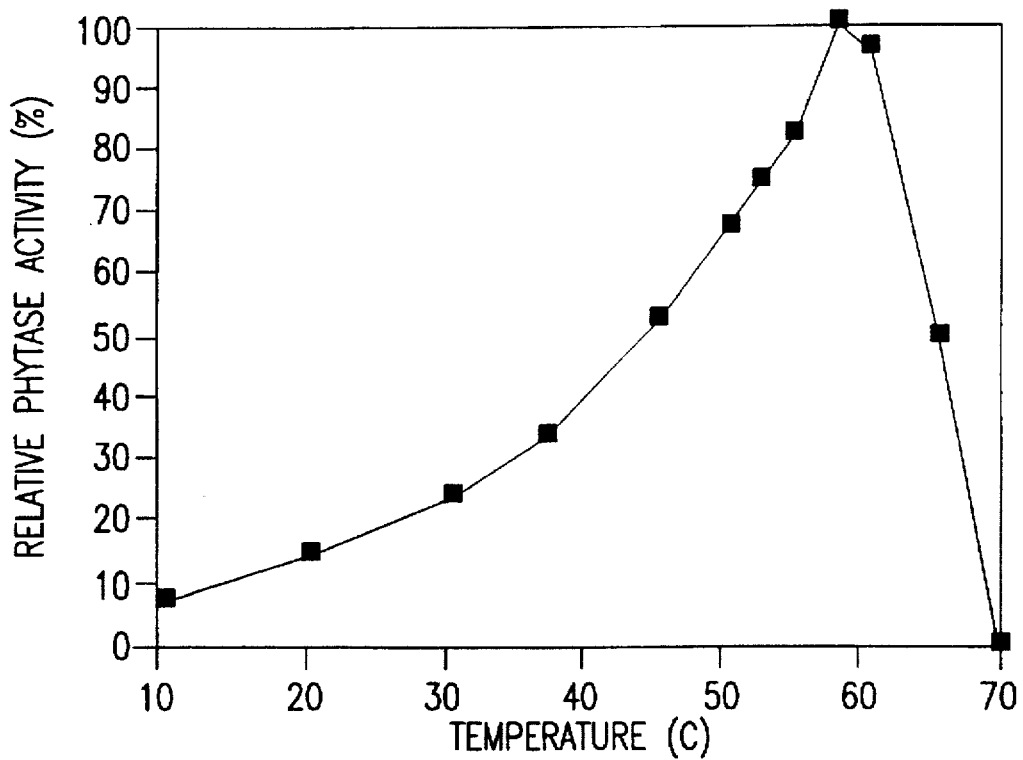
FIG. 2 shows the temperature optima at 55°–60° C., with >20% of maximal enzyme activity in the range of 25° C. to 65° C., for the purified phytase enzyme of FIG. 1, above.
Figure 3:
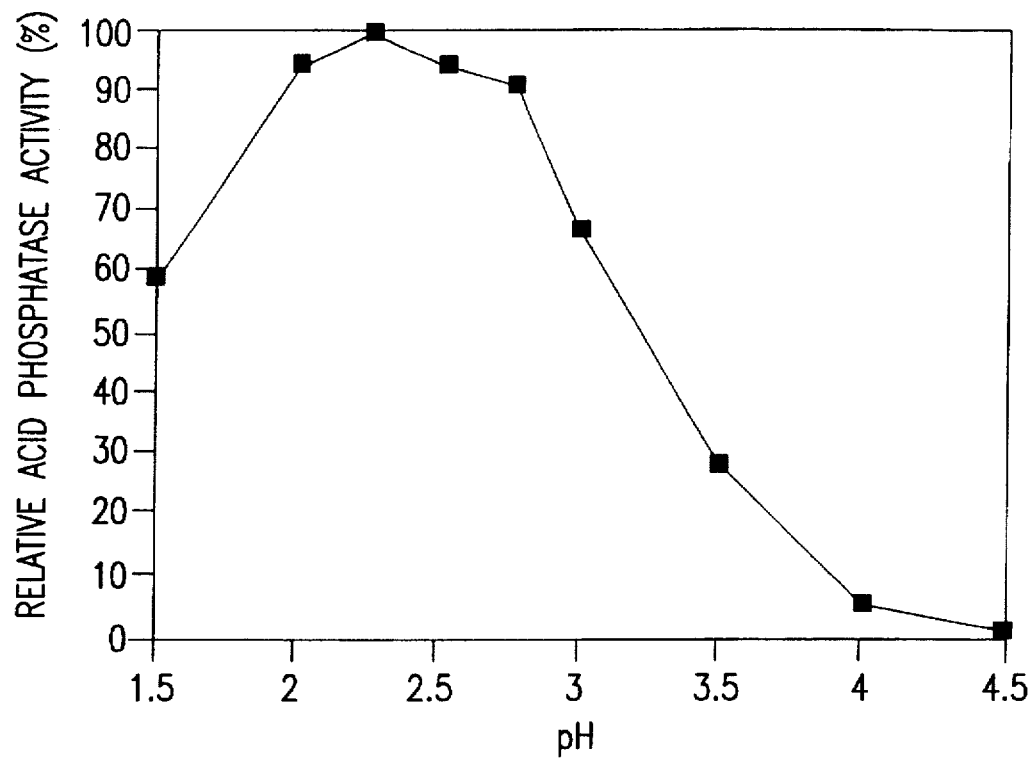
FIG. 3 shows the pH optima at 37° C. of pH2.5 acid phosphatase purified from *Aspergillus niger* var. awamori strain ALKO243 that has an apparent Km of 0.7 mM for sodium phytate at pH2.5, a pH optima of pH2.0–2.5, and >20% activity in the range of pH1.5 to pH3.5 (as described below in Example 1)
Figure 4:
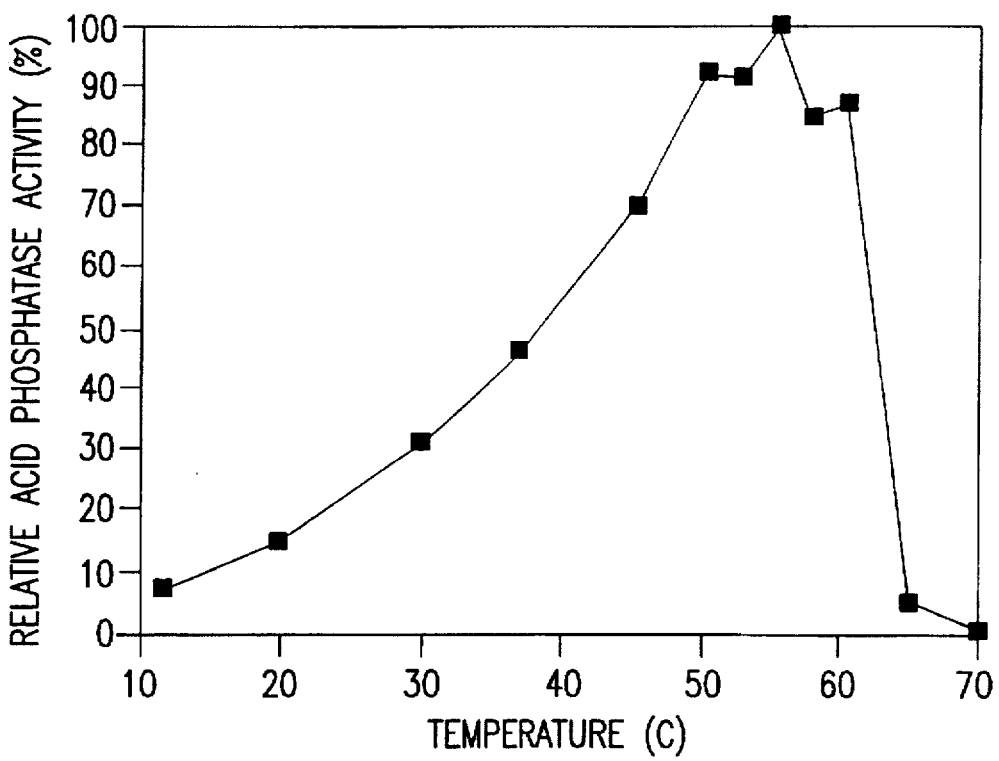
FIG. 4 shows the temperature optima at about 55° C., and >20% maximal enzyme activity in the range of 25° C. to 60° C., for the pH2.5 acid phosphatase of FIG. 3, above.
Figure 5:
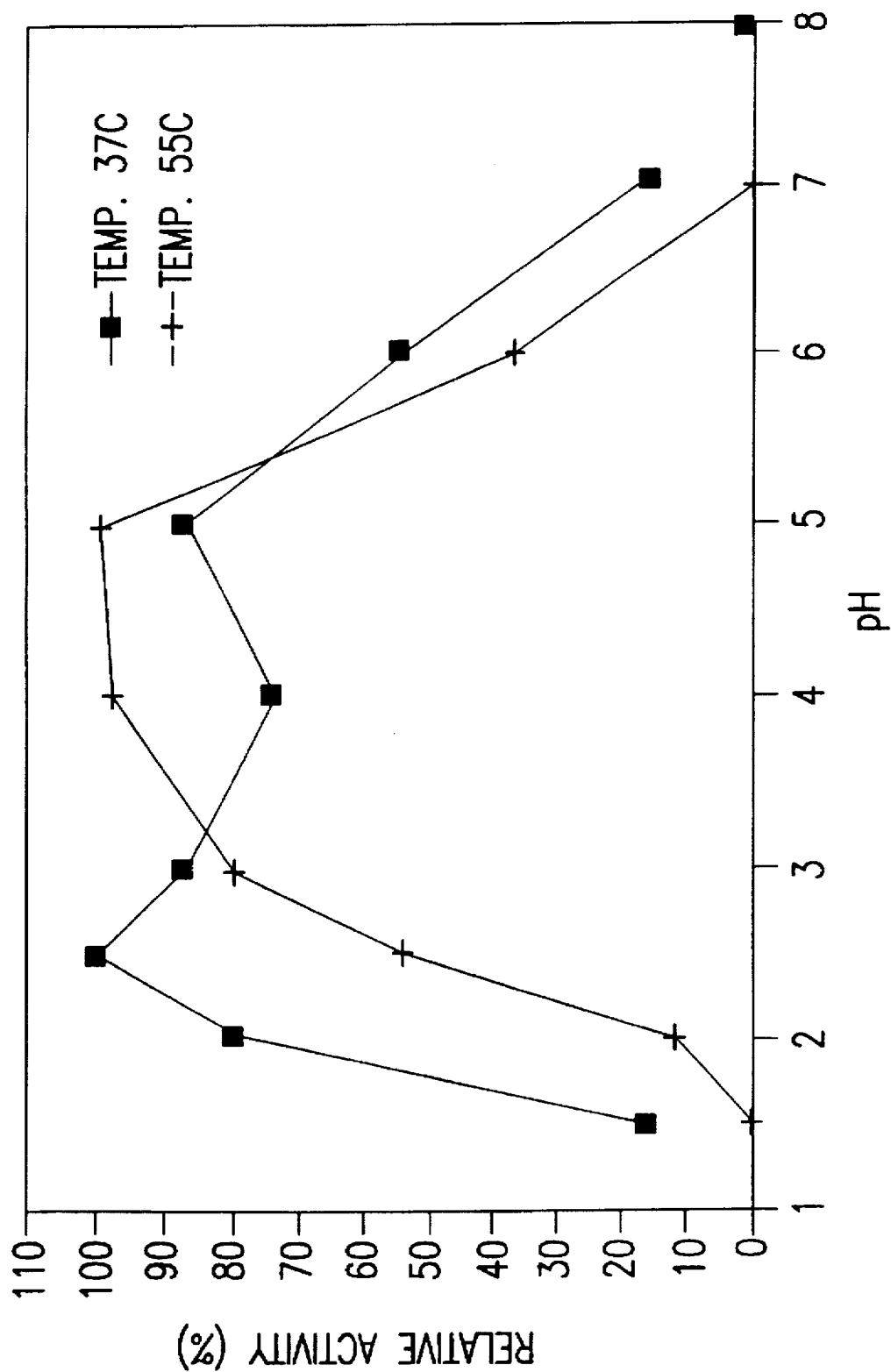
FIG. 5 shows the relative phytase activity (i.e., liberation of phosphate from sodium phytate) of Finase, a commercial preparation containing phytase and phosphatases, as a function of pH at 37° C. (squares) and 55° C. (+)
Figure 6:
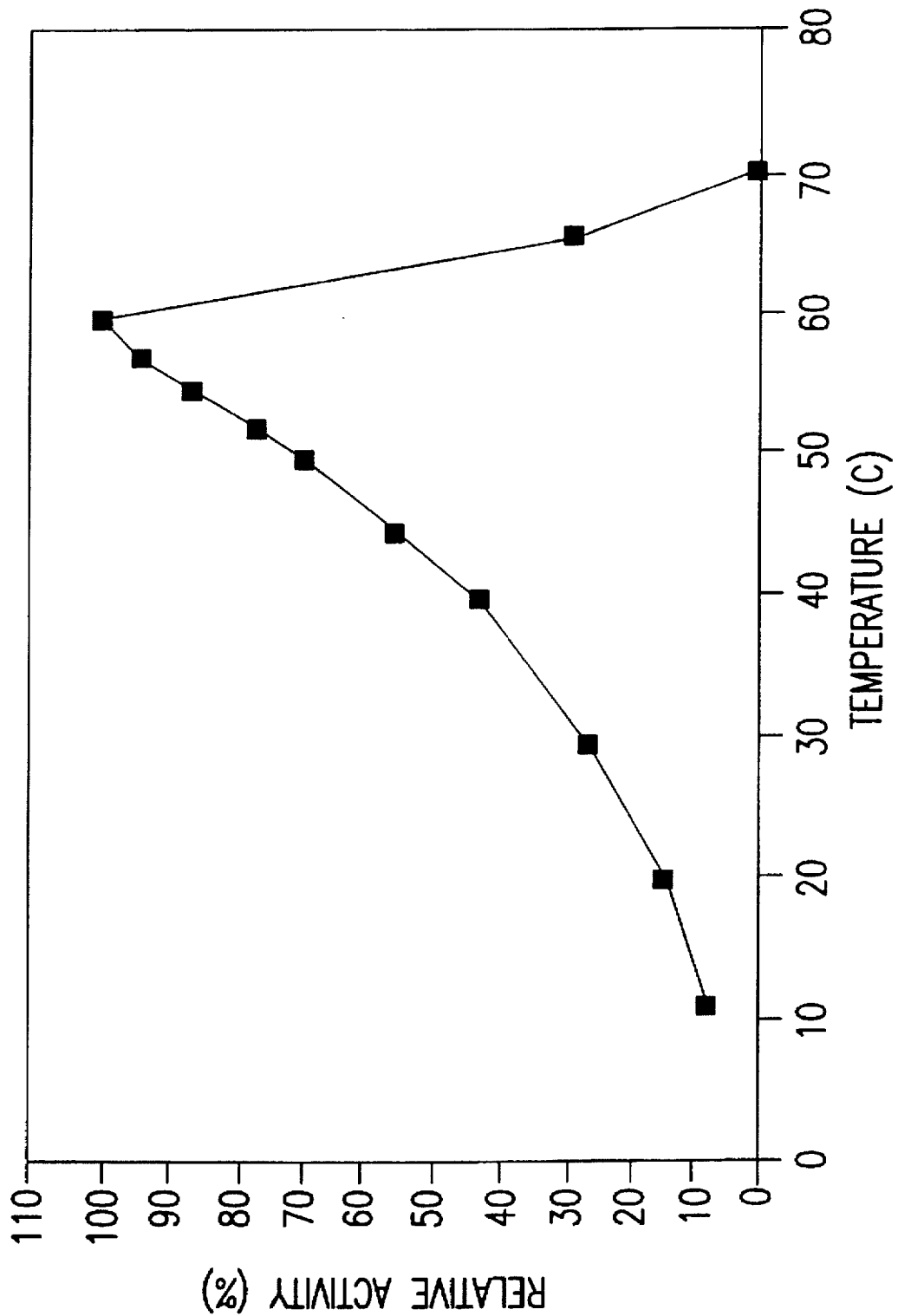
FIG. 6 shows the relative phytase activity (i.e., phosphate-liberating activity) of Finase (FIG. 5) as a function of temperature, i.e., between 10° C. and 70° C., at pH5.

Catalytic properties of the purified phytase and pH2.5 acid phosphatase enzymes:

Phytase: The purified phytase exhibited optimal enzyme activity (as measured at 37° C., in conditions of excess substrate), at a pH of approximately pH5.0 with a shoulder at pH2.5 and >20% of maximal enzyme activity in the range of pH2 to pH7 (FIG. 1). The temperature optimum for the purified phytase enzyme (at optimal Na-phytate substrate and pH5.0) was found to be in the range of 55°–60° C. with >20% of maximal enzyme activity in the range of 25° C. to 65° C. (FIG. 2). The purified phytase enzyme catalyzed hydrolysis of sodium phytate in the absence of added metal ion (i.e., the enzyme exhibited no absolute requirement for metal ions and thus was "metal ion independent"); however, the activity of the purified phytase enzyme was increased in the presence of $Mn^{2+}$, $Mg^{2+}$ and $Ca^{2+}$.

pH2.5 acid phosphatase: The apparent Km of the pH2.5 acid phosphatase for Na-phytate substrate at 37° C. and pH2.5 was determined to be about 0.7 mM; and, for paranitrophenylphosphate (PNP) at 37° C. and pH2.5 the apparent Km was 4 mM. The purified pH2.5 acid phosphatase enzyme exhibited a pH optimum in the range of pH2.0 to pH2.5 (i.e., at 37° C., in the presence of optimal concentrations of Na-phytate substrate) with >20% of maximal activity in the range of pH1.5 to pH3.5 (FIG. 3). The temperature optimum for pH2.5 acid phosphatase-mediated hydrolysis of Na-phytate was found to be about 55° C. with >20% of maximal enzyme activity in the range of 25° C. to 60° C. (FIG. 4). For comparison the pH/activity profile of a commercial non-purified Finase preparation is shown in FIG. 5, and the temperature/activity profile is shown in FIG. 6.

Degradation of phytate by phytase and pH2.5 acid phosphatase and mixtures thereof: Finase is a commercial preparation of enzymes from *Aspergillus* that includes a mixture of phytase and phosphatase. The ratio of pH2.5 acid phosphatase (HFU) activity to phytase activity (PU) of Finase was determined to be approximately 7:1. A comparison was made of the rate of phytate degradation by a commercial Finase enzyme preparation with the rate of the degradation by preparations of purified phytase, purified pH2.5 acid phosphatase and by mixtures thereof containing different acid phosphatase to phytase ratios. The ratio of acid phosphatase activity (HFU) to phytase activity (PU) of the purified phytase is approximately 0.4:1 whereas the acid phosphatase exhibits no phytase activity at pH5.0. The ratios of the enzyme mixtures are indicated in Tables 1.a and 1.b. The comparison was made at pH2.5 37° C. and at pH5.0 37° C. using 10 mM Na-phytate as substrate. The enzyme activities of all different preparations used in the experiments at pH2.5 were 10,000 HPU per mmol of Na-phytate substrate (HPU is the unit of phytase activity measured at pH2.5 using 0.2M glycine (HCl) buffer pH2.5 instead of Na-citrate buffer, see Materials and Methods at the end of Example 1). In the experiments conducted at pH5.0 the enzyme dosage per mmol of Na-phytate substrate was 10,000 PU, with the exception of the experiment carried out using purified acid phosphatase alone. Samples were taken from the reaction mixture after the times indicated (hours, h; 0, 1, 2, 8, 24, and 48h); the samples were freeze-dried and then later analyzed for inositol hexa-, penta-, tetra- and triphosphates (i.e., IP6, IP5, IP4 and IP3, respectively), as well as for free inositol (Ins) and inorganic phosphorus (Pi). Inositol hexa-, penta-, tetra-, and triphosphates were analyzed by the method of Sandberg et al. (1987). Inositol was analyzed by HPLC using Sugar Pak 1 column (300 mm×6.5 mm, Waters), 0.1 mM Ca-EDTA as eluent (Calcium-Titriplex Merck 8439), flow 0.6 ml/min at 90° C. The detection was by RI (Waters), using myo-inositol (Fluka) 0.1–0.5 mg/ml as the standard. Inorganic phosphorus was analyzed as described in Materials and Methods in the end of Example 1. The results of these experiments are presented in Table 1a and Table 1b, below.

TABLE 1a

| pH 2.5 | | Yield, % of Theoretical[a] | | | | | |
|---|---|---|---|---|---|---|---|
| Enzyme(s) dosage/mmol substrate | Time (h) | IP6 | IP5 | IP4 | IP3 | Ins | $P_i$ |
| | 0 | 100 | 0 | 0 | 0 | 0 | |
| Finase | 1 | 40 | 13 | 19 | 0 | 0 | |
| 10,000 HPU | 2 | 39 | 20 | 51 | 8 | 0 | |
| | 8 | 0 | 0 | 2 | 38 | 5 | |

TABLE 1a-continued

| pH 2.5 | | Yield, % of Theoretical[a] | | | | | |
|---|---|---|---|---|---|---|---|
| Enzyme(s) dosage/mmol substrate | Time (h) | IP6 | IP5 | IP4 | IP3 | Ins | $P_i$ |
| | 24 | 0 | 0 | 0 | 0 | 57 | |
| | 48 | 0 | 0 | 0 | 0 | 94 | 103 |
| | 0 | 100 | 0 | 0 | 0 | 0 | |
| Phytase | 1 | 20 | 29 | 20 | 0 | 0 | |
| 10,000 HPU | 2 | 5 | 30 | 68 | 22 | 0 | |
| | 8 | 0 | 0 | (+) | 24 | 0 | |
| | 24 | 0 | 0 | 0 | 0 | 0 | |
| | 48 | 0 | 0 | 0 | 0 | 0 | 87 |
| | 0 | 100 | 0 | 0 | 0 | 0 | |
| pH 2.5 Acid Phosphatase | 1 | 67 | 8 | 26 | 0 | 0 | |
| 10,000 HPU | 2 | 54 | .9 | 37 | (+) | 0 | |
| | 8 | 26 | 2 | 42 | 12 | 1 | |
| | 24 | 2 | 1 | 8 | 4 | 40 | |
| | 48 | 1 | 0 | 5 | 67 | 88 | |
| | 0 | 100 | 0 | 0 | 0 | 0 | 0 |
| Phytase 9,000 HPU | 1 | 44 | 23 | 32 | 20 | 0 | 16 |
| pH 2.5 Acid Phosphatase 1,000 HPU | 2 | 6 | 13 | 71 | 17 | 0 | 31 |
| | 8 | 0 | 2 | 10 | 0 | 2 | 79 |
| HFU:PU | 24 | 0 | 0 | 0 | 0 | 33 | 93 |
| 0.8:1 | 48 | 0 | 0 | 0 | 0 | 63 | 98 |
| | 0 | 100 | 0 | 0 | 0 | 0 | 0 |
| Phytase 5,000 HPU | 1 | 38 | 12 | 47 | (+) | 0 | 15 |
| pH 2.5 Acid Phosphatase 5,000 HPU | 2 | 17 | 7 | 76 | (+) | 6 | 27 |
| | 8 | 0 | 0 | 7 | 19 | 12 | 69 |
| HFU:PU | 24 | 0 | 0 | 0 | 0 | 76 | 99 |
| 4.4:1 | 48 | 0 | 0 | 0 | 0 | 101 | 104 |
| | 0 | 100 | 0 | 0 | 0 | 0 | 0 |
| Phytase 1,000 HPU | 1 | 40 | 16 | 39 | (+) | 0 | 10 |
| pH 2.5 Acid Phosphatase 9,000 HPU | 2 | 27 | 8 | 26 | (+) | 1 | 17 |
| | 8 | 7 | 2 | 21 | 17 | 9 | 45 |
| HFU:PU | 24 | 0 | 0 | 6 | 5 | 46 | 79 |
| 36.4:1 | 48 | 0 | 0 | 0 | 0 | 102 | 103 |

[a]Yield, % of theoretical: the starting concentration of 10 mM Na-phytate substrate (IP6) in the assays was considered equal to 100% theoretical yield (i.e., of IP6); for IP6, the concentration of residual Na-phytate at the end of the assay was divided by the starting concentration to obtain the % indicated in Tables 1a and 1b; for IP5, IP4, IP3, Ins, and P, the maximal theoretical concentration of each degradation product that could be released from IP6 (i.e., by acid hydrolysis) was calculated and considered equal to 100% theoretical yield of the respective degradation product; the concentration of residual degradation product at the end of the assay was divided by the theoretical concentration to obtain the % indicated in Tables 1a and 1b; (+) traces.

TABLE 1b

| pH 2.5 | | Yield, % of Theoretical[a] | | | | | |
|---|---|---|---|---|---|---|---|
| Enzyme(s) dosage/mmol substrate | Time (h) | IP6 | IP5 | IP4 | IP3 | Ins | $P_i$ |
| | 0 | 100 | 0 | 0 | 0 | 0 | |
| Finase | 1 | 51 | 16 | 24 | 0 | 0 | |
| 10,000 PU | 2 | 35 | 22 | 29 | 14 | 0 | |
| | 8 | 0 | 7 | 1 | 18 | 0 | |
| | 24 | 0 | 0 | 0 | 0 | 18 | |
| | 48 | 0 | 0 | 0. | 0 | 52 | 88 |
| | 0 | 100 | 0 | 0 | 0 | 0 | |
| Phytase | 1 | 43 | 33 | 27 | 11 | 0 | |
| 10,000 PU | 2 | 23 | 18 | 24 | 21 | 0 | |
| | 8 | 1 | 2 | 6 | 24 | 0 | |
| | 24 | 0 | 0 | 0 | 0 | 0 | |
| | 48 | 0 | 0 | 0 | 0 | 0 | 90 |
| | 0 | 100 | 0 | 0 | 0 | 0 | 0 |
| pH 2.5 Acid Phosphatase | 1 | 107 | 0 | 0 | 0 | 0 | 0 |
| 0 PU | 2 | 106 | 0 | 0 | 0 | 0 | 0 |
| 10,000 HPU | 8 | 105 | 0 | 0 | 0 | 0 | 0 |
| | 24 | 93 | 0 | (+) | (+) | 0 | i |
| | 48 | 96 | 0 | (+) | (+) | 0 | i |
| | 0 | 100 | 0 | 0 | 0 | 0 | 0 |
| Phytase 10,000 PU | 1 | 30 | 26 | 45 | (+) | 0 | 18 |
| pH 2.5 Acid Phosphatase 1,000 HPU | 2 | 27 | 23 | 36 | 32 | 0 | 21 |
| | 8 | 1 | 2 | 10 | 29 | 0 | 46 |

TABLE 1b-continued

| pH 2.5 | | Yield, % of Theoretical[a] | | | | | |
|---|---|---|---|---|---|---|---|
| Enzyme(s) dosage/mmol substrate | Time (h) | IP6 | IP5 | IP4 | IP3 | Ins | $P_i$ |
| HFU:PU | 24 | 0 | 0 | (+) | (+) | 4 | 82 |
| 1.4:1 | 48 | 0 | 0 | (+) | (+) | 17 | 90 |
|  | 0 | 100 | 0 | 0 | 0 | 0 | 0 |
| Phytase 10,000 PU | 1 | 34 | 12 | 65 | 0 | 0 | 21 |
| pH 2.5 Acid Phosphatase 5,000 HPU | 2 | 27 | 22 | 38 | 28 | 0 | 24 |
|  | 8 | 1 | 2 | 9 | 27 | 0 | 50 |
| HFU:PU | 24 | 0 | 0 | 0 | 0 | 21 | 88 |
| 5.4:1 | 48 | 0 | 0 | 0 | 0 | 59 | 96 |
|  | 0 | 100 | 0 | 0 | 0 | 0 | 0 |
| Phytase 10,000 PU | 1 | 30 | 11 | 54 | 0 | 0 | 24 |
| pH 2.5 Acid Phosphatase 9,000 HPU | 2 | 31 | 22 | 36 | 28 | 24 |  |
|  | 8 | (+) | 2 | 9 | 25 | 9 | 51 |
| HFU:PU | 24 | 0 | 0 | 0 | 0 | 46 | 88 |
| 9.4:1 | 48 | 0 | 0 | 0 | 0 | 102 | 102 |

[a]As in Table 1a, above.

The results presented in Tables 1a and 1b show that the purified phytase and pH2.5 acid phosphatase enzymes and the Finase commercial enzyme mixture catalyzed hydrolysis of Na-phytate to inositol and inorganic phosphate, but at differing rates and with different pH optima. Under optimal conditions of pH for each of the purified enzymes (i.e., pH5.0 for purified phytase; and pH2.5 for the purified pH2.5 acid phosphatase) approximately equivalent amounts of inorganic phosphate were released in 48 hours by all three enzyme preparations (i.e., 90% Pi for phytase; 88% Pi for acid phosphatase; and, 88% or 103% for the Finase mixture). However, the results also show that inositol (Ins, Tables 1a and 1b) production is markedly slower at pH5.0 than at pH2.5. Inositol, as the end product of Na-phytate hydrolysis, could not be detected at pH2.5 nor at pH5.0 when purified phytase enzyme is used alone, although IP6, IP5, IP4 and IP3 were completely removed during the hydrolysis time. It can be concluded that the probable hydrolytic end products of the purified phytase enzymes are inositol di-and/or monophosphates. In contrast, purified acid phosphatase catalyzed degradation of phytate (i.e., IP6= inositolhexaphosphates) at pH2.5, producing inositol as an end product. These combined results suggested that in a commercial mixture of phosphatases, such as Finase, phytase alone is not sufficient to enable complete conversion of phytate to inositol and inorganic phosphate. Rather, the results suggested that inositol end products may be derived from the action of enzymes with substrate specificity similar to that of purified pH2.5 acid phosphatase. The possibility was therefore considered that the products of phytate hydrolysis by phytase (i.e., IP5, IP4, IP3, IP2, IP 1) might serve as useful substrates for acid phosphatase that would convert the inositolphosphates into free inositol and inorganic phosphate. The results thus suggested a previously unsuspected cooperative enzyme activity for phytate degradation between phytase and pH2.5 acid phosphatase. To further explore this possibility the substrate specificities of the purified phytase and pH2.5 acid phosphatase were evaluated.

The substrate specificities of purified phytase and pH2.5 acid phosphatase were compared at 37° C. using equivalent concentrations of phytate substrate (i.e., 20 mM) and temperature (i.e., 37° C.). Phytase activity was measured at pH5.0 and acid phosphatase activity was measured at pH2.5 using the molybdate phosphate detection system described in the Materials and Methods section appearing at the end of EXAMPLE 1. A comparison of the relative activities of the two different enzymes on different substrates is presented in Table 2, below.

TABLE 2

Substrate Specificity of Substantially Purified Phytase and pH 2.5 Acid Phosphatase

| Substrate | Phytase Relative Activity(%)[a] | pH 2.5 Acid Phosphatase Relative Activity (%)[b] |
|---|---|---|
| Phytic acid Na-salt | 100 | 36 |
| Phytic acid K-Mg-salt | 106 | 34 |
| Phytic acid Ca-salt | 56 | 43 |
| Glucose 6-phosphate | 11 | 62 |
| ATP | 7 | 72 |
| Fructose 1,6-phosphate | 8 | 107 |
| Fructose 6-phosphate | 1 | 18 |
| L-a-glycerophosphate | 1 | 71 |
| p-nitroyhenyl phosphate | 24 | 100 |

[a]Percent relative activity = "the measured activity calculated as a % of that obtained with a standard substrate of phytase (i.e., Na-phytate defined as 100%)."
[b]Percent relative activity = "the measured activity calculated as a % of that obtained with a standard substrate of acid phosphatase (i.e., p-nitrophenyl phosphate; defined as 100%)"

The results presented in Table 1a, Table 1b and Table 2 show that purified phytase, while effective in mediating the hydrolysis of phytic acid, was less effective in catalyzing hydrolysis of other simpler phosphate-containing substrates. In contrast, purified pH2.5 acid phosphatase, while relatively effective in hydrolyzing simpler phosphates, was relatively ineffective in catalyzing hydrolysis of phytic acid. The results support the notion of a cooperative enzymatic mixture wherein the products of a purified phytase (e.g., inositol di-and mono-phosphates) might serve as substrates for a purified pH2.5 acid phosphatase so that free inositol and inorganic phosphate are the ultimate products of the reaction.

"Balanced" enzyme mixtures:

The possibility was next considered that an effective cooperative enzymatic mixture might be constructed by optimizing the amounts of purified phytase and purified pH2.5 acid phosphatases that were mixed together in a preparation so that the activity of the two different enzymes was "balanced", i.e., to achieve cooperative enzyme activity at a particular pH and temperature to give the optimal rate, efficiency, and completeness of phytate degradation to free inositol and inorganic phosphate. Studies were conducted in which mixtures of purified phytase and pH2.5 acid phosphatase were formulated at defined ratios of the two enzyme activities, but while such "balanced" mixtures of purified phytase and pH2.5 acid phosphatase offered advantages of increased rate of phytate hydrolysis and more complete conversion to free inositol and inorganic phosphate over commercial preparations, it was not considered cost-effective to purify, standardize, quality control (QC) and quality assure (QA) such a "balanced" mixture of enzymes for use in most commercial processes (e.g., for animal feeds) within desired ranges of ratios of enzyme activities, e.g., pH2.5 acid phosphatase to phytase.

To solve these problems the possibility was next considered that molecular techniques might be used to produce recombinant enzymes that were of sufficiently high quality to provide uniform standardized preparations, and with the necessary cost-efficiency and QC/QA properties required for commercial products of "balanced" mixtures.

Amino acid sequencing of phytase and pH2.5 acid phosphatase:

In order to obtain internal amino acid sequences of the purified proteins, peptide fragments were prepared using TPCK-trypsin (as described, see Materials and Methods, below). In addition, purified pH2.5 acid phosphatase was alkylated (i.e., using 4-vinyl pyridine) and then digested with lysylendopeptidase C, as described (Materials and Methods). The resultant peptides were purified by reverse-phase high pressure liquid chromatography (RP-HPLC) on a C18 RP column (as described in the Materials and Methods section, below). Amino terminal sequencing of purified peptides was conducted using a gas-pulsed liquid phase sequencer, and the released PTH amino acids were analyzed by RP-HPLC (as described, Materials and Methods). Carboxy-terminal sequencing was conducted using kinetic carboxypeptidase Y digestion, PITC derivatization, and RP-HPLC analysis of the PITC amino acids.

The amino acid sequences of the tryptic peptides of phytase and pH2.5 phosphatase, as well as the lysylendopeptidase peptides of pH2.5 phosphatase are presented in Tables 3 and 4, below. As the results presented in Table 3 and 4 indicate, some peptide preparations were not pure. Tables 3 and 4 also present a comparison of the peptide amino acid sequences with the amino acid sequence deduced from nucleotide sequencing of the genes and the cDNA (Example 2, below), i.e., brackets [] in Tables 3-4.

The amino terminal sequence of purified *Aspergillus niger* var. awamori strain ALKO243 phytase showed N-terminal sequence (i.e., peptide #1081/N-phy Table 3; LAVPAS(R)NQSTXDT) SEQ. ID. NO. 6 similar to, but not identical with the reported amino terminal sequence in an *A. ficuum* phytase (i.e., Ullah, 1988; LAVPASRNQSSGDT). One peptide (i.e., #420/10phy; LYVEMMQ(N)QA(E)Q(T)PLV) SEQ. ID. NO. 8 was similar to, but not identical in sequence to, a reported internal peptide in an *A. ficuum* phytase (i.e., Ullah, 1988, MMQCQAEQEPLVRVLVNDRX) SEQ. ID. NO. 9 . Carboxyterminal sequencing of phytase gave the sequence XSA-OH. One peptide (i.e., #675; Table 3) contained a KDPR SEQ. ID. NO. 10 sequence homologous with sequence reportedly present in other phosphatases (namely KDPRA; SEQ. ID. NO. 11 Ullah, 1991).

TABLE 3

Amino acid sequence of isolated peptides of phytase

| Peptide Nos | Amino Acid Sequence* [Amino Acid Sequence Deduced from DNA sequence]b |
|---|---|
| #132/12 phy | Tyr-Tyr-Gly-His(Leu)-Gly-Ala-Gly-Asn-Pro-Leu-Gly-Pro-Thr-Gln (SEQ ID NO.12) |
| #133 | [Tyr-Tyr-Gly-His----Gly-Ala-Gly-Asn-Pro-Leu-Gly-Pro-Thr-Gln](SEQ ID NO.13) |
| | Thr-Gly-Tyr-Val-Gln(Asn)-Tyr-Val-Gln-Met-(Gln) (SEQ ID NO.14) [not found in DNA] |
| #242/1 phy | Ala-Gln-Pro-Gly-Gln-Ala-Ala-Pro-Lys (SEQ ID NO.15) [Ala-Gln-Pro-Gly-Gln-Ser-Ser-Pro-Lys](SEQ ID NO.16) |
| #420/10 phy | Leu-Tyr-Val-Glu-Met-Met-Gln-(Asn)-Gln-Ala-(Glu)-Gln-(Thr)-Pro-Leu-Val (SEQ ID NO.8) |
| | Leu-Tyr-Val-Glu-Met-Met-Gln-Cys-Gln-Ala-Glu-Gln-Glu-Pro-Leu-Val](SEQ ID NO.17) |
| #410/13 phy | Phe-Ile-Glu-Gly-Phe-Gln-Ser-Asp-Lys (SEQ ID NO.18) [Phe-Ile-Glu-Gly-Phe-Gln-Ser-Asp-Lys](SEQ ID NO.18) |
| #416/7 phy | Tyr-Ala-Phe-Leu-Lys (SEQ ID NO.18) [Tyr-Ala-Phe-Leu-Lys] (SEQ ID NO.19) |
| #659/6 phy | Gly-Leu-Ser-Phe-Ala-Arg (SEQ ID No.20) [Gly-Leu-Ser-Phe-Ala-Arg] (SEQ ID NO.20) |
| #670 & #796/2 phy | Val-Ile-Ala-Ser-Gly-Glu-Lys (SEQ ID NO.21) [Val-Ile-Ala-SAer-Gly-Glu-Lys](SEQ ID NO.21) |
| #418/3 phy | Phe-Tyr-Gln-Arg (SEQ ID NO.22) [Val-Ile-Ala-Ser-Gly-Glu-Lys](SEQ ID NO.21) |
| #785/11phy | Phe-Tyr-Gln-Arg {=#418 above (SEQ ID NO.22)}, and Asp-Ser-Phe-Val-Arg (SEQ ID NO.23) |
| (not pure) | [Asp-Ser-Phe-Val-Arg] (SEQ ID NO.23) |
| #248 (not pure) | Val/Tyr-Leu/Glu-Val/Ser-Asn/Leu-Asp/Gln (SEQ ID NO.24) [not possible to compare to DNA] |
| #784/9 phy | Tyr-Glu-Ser-Leu-Thr-Arg (SEQ ID NO.25) [Tyr-Glu-Ser-Leu-Thr-Arg] (SEQ ID NO.25) |
| #675 (not pure) | Ser-Ala-Ala-Ser-Leu-Asn-Ser (SEQ ID NO.26) {a fragment of the trypsin enzyme} |
| | Leu-Lys-Asp-Pro-Arg (SEQ ID NO.27) [Leu-Lys-Asp-Pro-Arg](SEQ ID NO.27) |
| #783 (not pure)/ | Val-Ile-Ala-Ser-Gly-Glu-Lys (SEQ ID NO.21) {amount = #670 and 796, above} |
| 4 phy | Tyr-Pro-Thr-Glu-Ser-Lys (SEQ ID NO.28) [Tyr-Pro-Thr-Glu-Ser-Lys] |
| #244 (not pure) | Tyr/Asp-Phe/Pro-Asn/Ala-X/X-Gly [not possible to compare to DNA] |
| #793 | Leu-Glu-Asn/Pro-Asp/Phe-Leu-Asp/Ser-Gly/Leu-Phe/Val-Thr-Leu) (SEQ ID NO. 30) |
| | Leu-Glu-Asn-Asp-Leu-Ser-Gly-Val-Thr-Leu-Thr] (SEQ ID NO.31) |
| #792 (double | Tyr-Tyr-Gly-His-Gly-Ala-Gly-Asn-Pro-Leu-Gly-Pro-Thr-Gln-Gly-Val-Gly-Tyr-Ala-(SEQ ID NO.32) |
| sequence)/15 phy | Asn-Glu-Leu-Ile-Ala |
| | {=#132 (half of above} and Val-Tyr-Phe-Ala-Gln-Val-Leu-Ser (SEQ ID NO.33) |
| | From this double sequence, the following sequences can be deduced |
| | Val-Thr-Phe-Ala-Gln-Val-Leu-Ser (SEQ ID NO.34) [Val-Thr-Phe-Ala-Gln-Val-Leu-Ser] (SEQ ID NO.34) |
| | and Tyr-Tyr-Gly-His-Gly-Ala-Gly-Asn-Pro-Leu-Gly-Pro-Thr-Gln-Gly-Val-Gly-Tyr- |
| | Asn-Glu-Leu-Ile-Ala (SEQ ID NO.32) |
| #800/13 phy | Phe-Ile-Glu-Gly-Phe-Gln-Ser-Thr (SEQ ID NO.35) [Phe-Ile-Glu-Gly-Phe-Gln-Ser-Thr] (SEQ ID NO.35) |
| #797/14 phy | Asp/Asn-Tyr-Leu-Gln-Ser-Leu-Lys) (SEQ ID NO.36) ]Asp-Tyr-Leu-Gln-Ser-Leu-Lys] (SEQ ID NO.37) |
| #795 (Odd behavior in peptide sequencing) | Asn-Ile-Glu-Pro-Phe-Gln-Val-Asn (SEQ ID NO.38) [not found in DNA sequence.] |
| #799/8 phy | Val-Leu-Val-Asn-Asp-Arg (SEQ ID NO.38) {=#248, above} [Val-Leu-Val-Asn-Asp-Arg] (SEQ ID NO.39) |
| #1081/N-phy | Leu-Ala-Val-Pro-Ala-Ser-(Arg)-Asp-Gln-Ser-Thr-X-Asp-Thr (SEQ ID NO.6) |

TABLE 3-continued

Amino acid sequence of isolated peptides of phytase

| Peptide Nos | Amino Acid Sequence[a] [Amino Acid Sequence Deduced from DNA sequence][b] |
|---|---|
| C-terminal/C phy | [Leu-Ala-Val-Pro-Ala-Ser-Arg-Asn-Gln-Ser-Thr-Cys-Asp-Thr] (SEQ ID NO.40)<br>-(Arg)-Ser-Ala-OH [Cys-Ser-Ala-End] |

[a]peptide sequence,
X = amino acid not detected;
/ = either one or the other of the two indicated amino acids may be present, the assay was not definitive,
() = the presence of the amino acids in parentheses is subject to question beacuase of a weak signal of the PTH-amino acid; phytase peptides designted (phy) were obtained by tyrptic digestion;
[b][] = [peptide sequence deduced from DNA sequence, Example 2, below]; and,
: peptides number.

In sequencing of pH2.5 phosphatase, no results were obtained from amino terminal sequencing of either native or alkylated proteins purified from *Aspergillus niger* var. awamori strain ALKO243. One peptide (i.e., #1107T/7Lpho, Table 4, below) yielded a sequence that was identical to an amino terminal sequence reported in a phosphatase purified from *A. ficuum* (i.e., Ullah & Cummins, 1987; FSYGAAIPQSTQEKQFSQEFRDG)(SEQ. ID. NO. 4. Peptide #941C/10Lpho from purified pH2.5 phosphatase (ALKO243) may be a continuation of the #1107/7Lpho sequence, since it appears to be included in the *A. ficuum* N-terminus. The peptide #1112T/3Tpho (SEQ. ID. NO. 42) seems to be a continuation of peptide #943C/11Lpho, since it appears to have a partially overlapping sequence (i.e., FSSG in #1112T/3Tpho). The pH2.5 phosphatase peptide #816C/1Lpho contains a possible active site consensus sequence (i.e., RHGXRXP)(SEQ. ID. NO. 43

TABLE 4

Amino Acid Sequence of Isolated Tryptic (T) and Lysylendopeptidase (C) Peptide[a] of pH 2.5 Phosphatase

| Peptide Nos | Amino acid sequencing[b] [DNA sequencing][c] |
|---|---|
| #816C/1 Lpho | Arg-His-Gly-Glu-Arg-Tyr-Pro-Ser-Pro-Ser-Ala-Gly-Lys (SEQ ID NO.44)<br>[Arg-His-Gly-Glu-Arg-Tyr-Pro-Ser-Pro-Ser-Ala-Gly-Lys] (SEQ ID NO.44) |
| #817C and 1107T/7 Lpho | Phe-Ser-Tyr-Gly-Ala-Ala-Ile-Pro-Gln-Ser-Thr-Gln-Glu-Lys (SEQ ID NO.45)<br>[Phe-Ser-Tyr-Gly-Ala-Ala-Ile-Pro-Gln-Ser-Thr-Gln-Glu-Lys] (SEQ ID NO.45) |
| #847C/5 Lpho | Asp-Ile-Glu-Glu-Ala-Leu-Ala-Lys (SEQ ID NO.46)<br>[Asp-Ile-Glu-Glu-Ala-Leu-Ala-Lys] (SEQ ID NO.46) |
| #826C (not pure) | Ser/Ala-Ile-Glu/Pro-(Glu) (SEQ ID NO.47)<br>[not possible to compare to DNA] |
| #943C/11 Lpho | Ala-Arg-Tyr-Gly-His-Leu-Trp-Asn-Gly-Glu-Thr-Val-Val-Pro-Phe-Phe-Ser-Ser-Gly (SEQ ID NO.48)<br>[Ala-Arg-Tyr-Gly-His-Leu-Trp-Asn-Gly-Glu-Thr-Val-Val-Pro-Phe-Phe-Ser-Ser-Gly] (SEQ ID NO.48) |
| #938C (not pure)/2 Lpho | (Ser/Arg)-Tyr/His-Gly-Gly/Glu-Asn/Arg-Gly/Tyr-Pro-Tyr/Ser-(Pro)-Glu/Ser-(Ala)-(Gly) (SEQ ID NO.49)<br>[only part of sequence compared to DNA sequence]<br>[Tyr-Gly-Gly-Asn-Gly-Pro-Tyr] (SEQ ID NO.50) |
| #941C (not pure)/10 Lpho | Gln-Phe-Ser-Gln-Glu-Phe-X-Asp-Gly-Tyr-(Arg) (SEQ ID NO.51) {Predominant species}<br>[Gln-Phe-Ser-Gln-Glu-Phe-Arg-Asp-Gly-Tyr] (SEQ ID NO.52)<br>(Thr/His)-Tyr-Gly-Gly-Asn-Gly-X-Tyr/Pro (SEW ID NO.53) {=#938C, above} {Minor species} |
| #1106T and #1112T/3 Tpho | Phe-Ser-Ser-Gly-Tyr-Gly-Arg (SEQ ID NO.54)<br>[Phe-Ser-Ser-Gly-Tyr-Gly-Arg] (SEQ ID NO.54) |
| #1108T (not pure)/9 Tpho | Val-Ala-Phe-Gly-Asn-Pro-Tyr) (SEQ ID NO.55) and (Asp/Glu)-Leu-Asn-Ala-Ile-Leu-Phe/Lys (SEQ ID NO.56)<br>-from the sequence above the following sequences were deduced:<br>Val-Ala-Phe-Gly-Asn-Pro-(Tyr) (SEQ ID NO.55) and (Asp/Glu)-Leu-Asn-Ala-Ile-Leu-Phe/Lys (SEQ ID NO.56)<br>[Val-Ala-Phe-Gly-Asn-Pro-Tyr] (SEQ ID NO. 55) and [not found in DNA sequence] |
| #1110T (not pure)/6 Tpho | Asp-Ile-Glu-Glu-Ala-Leu-Ala-Lys {=#847C, above (SEQ ID NO.46)} and Gln-Leu-Pro-Gln-Phe-Lys (SEQ ID NO.57) [Gln-Leu-Pro-Gln-Phe-Lys] (SEQ ID NO.57) |
| #1111T/4 Tpho | Val-Ser-Tyr-Gly-Ile-Ala (SEQ ID NO.58) [Val-Ser-Tyr-Gly-Ile-Ala] (SEQ ID NO.58) |

[a]T: = trypsin digestion;
C: = lysylendopeptidase C digestion of 4-vinylpyridine treated pH 2.5 phosphatase;
[b]peptide sequence,
X = amino acid not detected;
/ = either one or the other of the two indicated amino acids may be present, the assay was not definitive,
() = the presence of the amino acids in parenthesis is subject to question because of a weak signal of the PTH-amino acid; phosphatase peptides (pho) obtained by lysylendopeptidase digestion are identified (L), alkylated phosphatase peptides obtained by trypsin digestion are identified (T); and,
[c][] = [peptide sequence deduced from DNA sequence, Example 2, below]; and,
peptide number.

From these amino acid sequences one peptide sequence from phytase (i.e., #420, Leu Tyr Val Glu Met Met Gln (Asn) Gln Ala (Glu) Gln (Thr) Pro Leu Val (SEQ. ID. NO. 16) with the questionable (Asn) corrected to Cys; Ullah, 1988; Table 3) and two from pH2.5 phosphatase (i.e., #816C; Arg His Gly Glu Arg Tyr Pro Ser Pro Ser Ala Gly Lys (SEQ. ID. NO. 62)and #1110T; Gln Leu Pro Gln Phe Lys (SEQ. ID. NO. 62), Table 4) were selected as being useful for the preparation of degenerate oligonucleotide probes for molecular cloning, as described below in Example 2.

Materials and Methods:

Phytase and pH2.5 acid phosphatase enzyme assays: Molybdate detection system:

Both assays measure the amount of inorganic phosphate that is released by enzyme action as colorimetrically quantifying using reduction of a phosphomolybdate complex. One phytase unit (PU) is the amount of enzyme which liberates, under the conditions described below, 1 nmol of inorganic phosphate from Na-phytate in one minute at 37° C. One pH2.5 acid phosphatase unit (HFU) is the amount of enzyme which liberates, under the conditions indicated below, 1 nmol of inorganic phosphate from P-nitrophenyl phosphate in one minute.

Phytase activity was determined by adding 1 ml of substrate (1% sodium phytate freshly prepared daily [Sigma #P3168], in 0.2M citrate buffer, pH5.0) to 1 ml of diluted enzyme supernatant to initiate the hydrolysis of orthophosphate. After exactly fifteen minutes at 37° C., the hydrolysis reaction was terminated by the addition 2 ml of 15% TCA (trichloroacetic acid, Merck #807) followed by mixing, cooling, and centrifugation to remove any precipitate that forms. Released orthophosphate was measured by the addition of an equal volume of freshly prepared Reagent C (i.e., 3 volumes of 1M sulfuric acid mixed with 1 volume of 2.5% (w/v) ammonium molybdate (Merck #1182) and 1 volume of 10% (w/v) ascorbic acid (Merck #127) to a 1:10 dilution of the hydrolysis reaction mixture (above). The Reagent C mixture was incubated at 50° C. for twenty minutes. The absorbances were measured at 820 nm against a reagent blank and known standards (1:100–1:400 dilutions of 9.0 mM $KH_2PO_4$: Merck #4873) that were used to construct a standard curve. The amount of phosphate liberated by phytase was used to calculate phytase in the following manner: namely, the $A_{820nm}$ value for the phytase was compared with the $A_{820nm}$ values of the phosphate standard curve and after correcting for any dilution factors the phytase activity was obtained by dividing the phosphorus concentration (nmol/ml) by the hydrolysis time (i.e., 15 min).

pH2.5 acid phosphatase activity was determined in a similar fashion: namely, 0.1 ml of diluted enzyme (diluted in 0.2M Glycine-HCl buffer, pH2.5) was added to 1.9 ml of substrate (30 mM p-nitrophenyl phosphate [Boehringer Mannheim] dissolved in 0.2M Glycine —HCl buffer) pH2.5. After a fifteen-minute incubation at 37° C., the reaction was terminated by addition of an equal volume of 15% TCA (as above). The released orthophosphate was measured using Reagent C (as described above), and the activity determined by a comparison to known diluted phosphate standards (as above) and by using the calculations described above.

Preparation of tryptic peptide fragments for amino acid sequencing:

Purified phytase (70 µg) in 50 mM Tris-HCl pH7.9 was digested with 2% (w/w) trypsin (TPCK-treated, Sigma) for 2 h at 37° C. and then with a further 2% (w/w) trypsin for 21 h. Purified pH2.5 acid phosphatase in 100 mM Tris-HCl pH8.0 was treated with 2% (w/w) trypsin for 20 h at 37° C. and then with a further 2% (w/w) trypsin for 6 h. The peptides were purified as described below.

Preparation of lysylendopeptidase C peptide fragments for amino acid sequencing:

Purified pH2.5 acid phosphatase was alkylated using 4-vinylpyridine as follows: To lyophilized pH2.5 acid phosphatase (75 µg) was added 40 µl 0.5M Tris-HCl pH7.5 containing 6M guanidium hydrochloride, 2 mM EDTA and 34 mM DTT. After addition of 1 µl 4-vinylpyridine (Sigma), the reaction mixture was kept at room temperature (22° C.) for 1 h. The reaction was stopped by addition of 10 ml 1.4M DTT. Alkylated phosphatase was then purified on HPLC with a C-1 reverse-phase column (TSK TMS 250; 0.46×4 cm) using a 20% to 70% ACN/0.06% TFA gradient (80% to 30% 0.1% TFA) in 30 min. The fractions absorbing at 218 nm were pooled and evaporated in a Speed-Vac vacuum centrifuge. The dried sample was then resuspended by adding 60 µl 70 mM Tris-HCl pH9.1 and digested with 2% (w/w) lysylendopeptidase C (Wako Chemicals) for 2 h at 37° C. After addition of a further 2% (w/w) lysylendopeptidase C, the incubation at 37° C. was prolonged to 26 h. The peptides were purified as described below.

Peptide purification and amino terminal sequencing:

The peptides obtained from enzymatic digestion (above) were separated by HPLC on a C-18 reverse-phase column (Vydac 218 TP B5; 0.46 ×25 cm) with a 90 min gradient from 0 to 60% ACN/0.06% TFA (100 to 40% 0.1% TFA). Absorbance at 218 nm was used for detection of peptides. Amino terminal sequencing of the purified peptides, as well as the native proteins, was done by degrading them in a gas-pulsed liquid-phase sequencer (Kalkkinen & Tilgmann, 1988). The released PTH-amino acids were analyzed on-line by using narrow-bore reverse-phase HPLC.

Carboxy terminal sequencing of phytase:

A lot of purified phytase (53 µg) was digested with carboxypeptidase Y (Sigma, 0.6 U) in 50 mM sodium acetate pH5.6 containing 10% urea and 0.05% SDS at room temperature (22° C.). Samples of the digestion were withdrawn at various time points. These were dried in a Speed-Vac vacuum centrifuge and derivatized with phenylisothiocyanate (PITC) according to the amino acid analyzing kit Pico-Tag (Waters association). Analysis of the derivatized amino acids was performed by reverse-phase HPLC with the Pico-Tag C-18 column, and quantified by identically derivatized amino acid standards.

EXAMPLE 2

Isolation And Characterization Of Phosphatase Genes Phytase And pH2.5 Acid Phosphatase

[General materials and methods are described in the section entitled "Materials and Methods, " which follow the example.]

For molecular cloning of the phytase and the pH2.5 acid phosphatase genes interior peptides from the enzymes (as described above) were prepared from A. niger var. awamori strain ALKO243. The genomic DNA encoding phytase and pH2.5 acid phosphatase were cloned and cDNA was also cloned so that the complete coding sequence could be determined. Finally, expression vectors were constructed (as described in Example 3, below) that secreted each of the enzymes in a functional form, and a dual-gene-transformed strain was also selected that synthesized and secreted the desired cost-effective and "balanced" mixture of enzymes at a ratio of pH2.5 acid phosphatase to phytase confering upon the mixture the property of cooperative enzyme activity that is desirable in a particular commercial use, e.g., in animal feeds.

Design of oligonucleotide probes:

Several internal peptide fragments were sequenced from purified phytase and pH2.5 acid phosphatase, Example 1, above. A degenerate oligonucleotide complementary to all eight possible codon combinations of a chosen region (brackets, Table 3) of an internal phytase peptide was synthesized using the Pharmacia Gene Assembler Plus: namely, the peptide from phytase with the sequence Leu Tyr Val Glu Met Met Gln Cys Gln Ala Glu Gin (SEQ. ID. NO. 19) (i.e., peptide #420, Table 3 with the questionable (Asn) corrected with Cys; Ullah, 1988). PHY-1, shown in Table 5, is a 17-base oligonucleotide mixture which contains one perfect match out of eight combinations.

Figure 7:
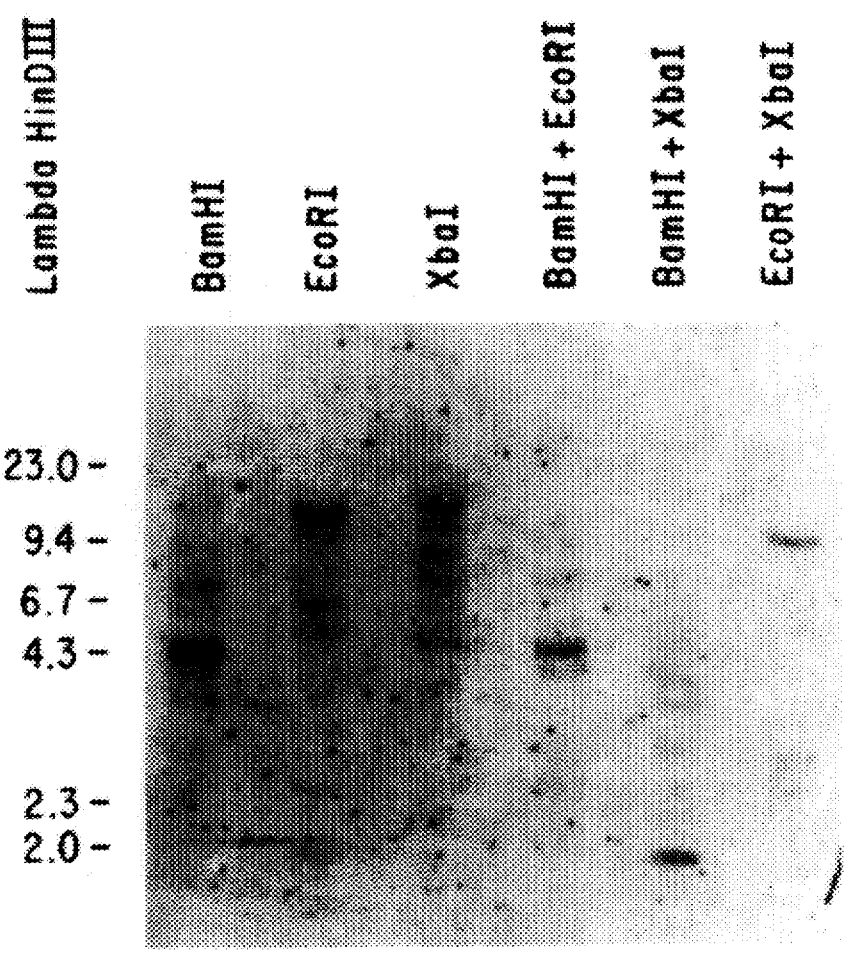
FIG. 7 shows an autoradiogram of radiolabeled degenerate oligonucleotide phytase probe PHY-1 hybridizing under stringent conditions with endonuclease fragments of genomic DNA generated with BamHI; EcoRI; XbaI; BamHI+EcoRI; BamHI+XbaI; and EcoRI+XbaI (as described in Example 2, below)
Figure 8:
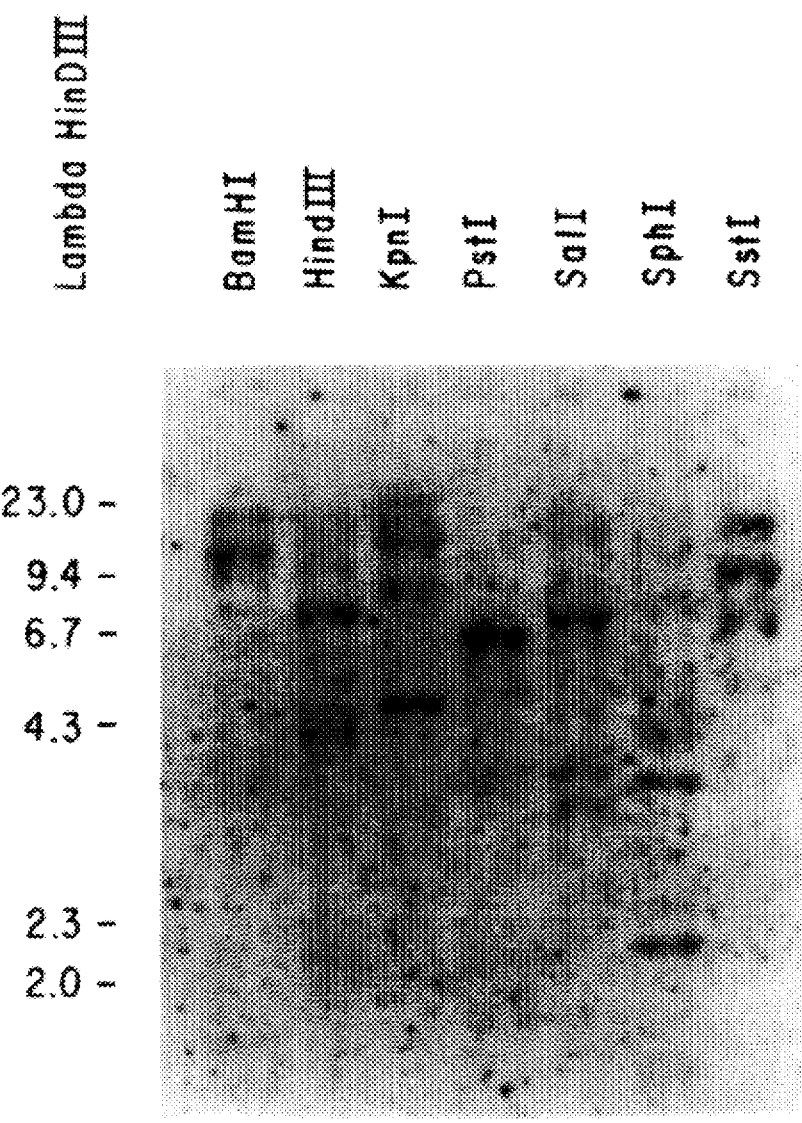
FIG. 8 shows an autoradiogram of radiolabeled specific oligonucleotide pH2.5 acid phosphatase probe PHY-31 hybridizing under stringent conditions with endonuclease fragments of genomic DNA generated with BamHI, HindIII, KpnI, PstI, SalI, SphI, or SstI (as described in Example 2, below)

A 17 mer degenerate oligonucleotide, PHY-31, was designed from an acid phosphatase peptide: namely, peptide #816C from pH2.5 phosphatase (i.e., Arg His Gly Glu Arg Tyr Pro Ser Pro Ser Ala Gly Lys(SEQ. ID. NO. 66)). Through the incorporation of a neutral inosine, one perfect match out of 64 possible combinations exists in PHY-31. The nucleotide sequence of oligo PHY-31 and corresponding peptide sequence is shown in Table 5. PHY-34 is a 17 mer mixture with 128-fold degeneracy constructed to coding sequence for peptide #1110T of pH2.5 acid phosphatase; PHY-35 is a 17 mer mixture with 64-fold degeneracy also constructed to coding sequence for peptide #1110T. Both PHY-34 and PHY-35 are necessary for complete representation of Peptide #1110T. Peptide #1110T is derived from a trypsin digestion of purified native pH2.5 acid phosphatase (Table 4, above).

with a 4% SDS-TE buffer. Cell debris was removed and supernatant was removed and extracted twice with an equal volume of Tris-saturated phenol:chloroform (1:1). Genomic DNA was precipitated with $NH_4OAC$ and EtOH. Pelleted DNA was purified by ultracentrifugation through CsCl as recovered as described by Maniatis et al. Hybridization to genomic DNA with ($\lambda^{32}P$) ATP labelled degenerate oligos (Maniatis et al., 1982) was done at 42° C. overnight on filters in oligo hybridization solution (6×SSPE, 0.5% SDS, 3×Denhardts, 100 µg/ml tRNA). Non-specific binding was removed by washing the filters twice for 30 minutes at room temperature with 2×SSC, 0.1% SDS, and once for 5 minutes at 42° C. in fresh solution. Overnight exposure on Kodak X-Omat AR film with intensifying screens revealed positively hybridizing bands Likewise, genomic DNA from ALKO243 was probed with radiolabelled specific pH2.5 acid phosphatase oligo PHY-31 (under the conditions described in FIG. 7, above). The autoradiogram is shown in FIG. 8. Although the specificity of PHY-31 was not as high as with PHY-1, it appeared as if, at most, two bands were recognized by this oligonucleotide probe.

Isolation and characterization of the phytase gene:

Genomic DNA was partially digested with Sau3A in order to produce fragments 10–23 kb in length. Digested DNA was ligated to BamHI cut dephosphorylated Lambda Dash II vector arms [Stratagene]. The ligation was packaged in vitro

TABLE 5

Oligonucleotide Probes for Phytase and pH2.5 Phosphatase

| Enzyme | Amino Acid Sequence[a] | Oligonucleotide Probe |
|---|---|---|
| Phytase | Peptide #420 (SEQ. ID. NO: 59): | Oligo PHY-1: |
| | Leu Tyr Val Glu [Met Met Gln Cys Gln] Ala Glu Gln | 3'- CAT CAT GTT ACG GTT CG -5' (SEQ. ID. NO: 60) |
| | | 3'- CAT CAT GTC ACA GTC CG -5' (SEQ. ID. NO: 61) |
| pH2.5 Acid P'ase | Peptide #816C (SEQ. ID. NO: 44): | Oligo PHY-31: |
| | Arg [His Gly Glu Arg Tyr Pro] Ser Pro Ser Ala Gly Lys | 3'- GTG CCG CTC GCI ATG GG -5' (SEQ. ID. NO: 62) |
| | | 3'- GTA CCA CTT TCI ATA GG -5' (SEQ. ID. NO: 63) |
| | | 3'- GTG CCG CTC GCI ATG GG -5' (SEQ. ID. NO: 64) |
| | | 3'- GTG CCC CTC GCI ATG GG -5' (SEQ. ID. NO: 65) |
| | Peptide #1110T (SEQ. ID. NO: 57) | Oligo PHY 34: |
| | [Gln Leu Pro Gln Phe Lys] | 5'- CAA CTG CCG CAA TTT AA -3' (SEQ. ID. NO: 66) |
| | | 5'- CAG CTA CCA CAG TTC AA -3' (SEQ. ID. NO: 67) |
| | | 5'- CAA CTT CCT CAA TTT AA -3' (SEQ. ID. NO: 68) |
| | | 5'- CAA CTC CCC CAA TTT AA -3' (SEQ. ID. NO: 69) |
| | | Oligo PHY 35: |
| | | 5'- CAA TTA CCG CAA TTT AA -3' (SEQ. ID. NO: 70) |
| | | 5'- CAG TTG CCA CAG TTC AA -3' (SEQ. ID. NO: 71) |
| | | 5'- CAA TTA CCT CAA TTT AA -3' (SEQ. ID. NO: 72) |
| | | 5'- CAA TTA CCC CAA TTT AA -3' (SEQ. ID. NO: 73) |

[a][ ] = region of sequence utilized in construction of degenerate oligonucleotides; peptides as described in Tables 3 and 4, above.

Probing Genomic ALKO243 DNA With Degenerate Oligonucleotides:

In order to evaluate the specificity of the degenerate oligonucleotides, total genomicDNA from ALKO243 was probed with PHY-1 end labelled with [$\lambda-^{32}P$]-ATP to a high specific activity using E. coli Polynucleotide T4 kinase [BRL]. FIG. 7 shows that with a high stringency wash, a unique band hybridized to phytase oligo PHY-1. At this stringency, a single band was recognized by the degenerate oligo which made it a good candidate for library screening.

FIG. 7. A. niger var. awamori strain ALKO243 genomic DNA probed with phytase oligonucleotide PHY-1. Genomic DNA was isolated by a neutral lysis method. Briefly, finely ground frozen dried mycelia was lysed using Stratagene's Gigapack Gold packaging extracts. Packaged phage was used to infect E. coli strain P2392 to obtain plaques. $5 \times 10^4$ plaque forming units were screened with phytase oligo PHY-1 using the following conditions: namely, 42° C. overnight on filters in oligonucleotide hybridization solution (6×SSPE, 0.5% SDS, 3×Denhardts, 100 µg/ml tRNA). Non-specific binding was removed by washing the filters twice for 30 minutes at room temperature with 2 X SSC, 0.1% SDS, and once for 5 minutes at 42° C. in fresh solution. Overnight exposure on Kodak X-Omat AR film with intensifying screens revealed positively hybridizing plaques. Twelve strongly hybridizing plaques were picked for further characterization. Lambda phage with inserts that hybridized to the PHY-1 probes, and had an identical size to genomic DNA fragments on 0.8% agarose gel electrophoresis, were chosen for subcloning and eventual nucleotide sequencing (as described below, Materials and Methods).

Subcloning and sequencing of phytase genomic clones:

Bacteriophage DNA isolated essentially by the method of Yamamoto (1970) from each of the 12 candidates was digested with restriction endonucleases and probed with the PHY-1 oligonucleotide. A 1.8 kb BamHI/XbaI hybridizing fragment previously identified in genomic Southerns was isolated from clone number CH7 and subcloned into M13mp18 and M13mp19 [BRL]. Subclone CH7 that reacted positively with oligonucleotide probes for phytase (i.e., PHY-1) was sequenced.

The nucleotide sequence of this subclone revealed regions corresponding to the reported nucleotide sequence of other known phytase peptide sequences, thus confirming the probable identity of the clone as a phytase genomic DNA. Continued sequencing of an overlapping 2.6 kb SphI fragment revealed an open reading frame of 1409 bp that included 15 internal peptide sequences and N-terminal peptide sequence. Analysis of upstream sequence with the IntelliGenetics' PC/GENE program "SIGNAL" (based on the method of Standen, 1984), revealed a strong eukaryote Kozak consensus sequence followed by a methionine initiation codon. However, this ATG was out of frame with respect to the remainder of the sequence. A potential 102 bp intron delineated by consensus fungal donor, lariat and acceptor sequences (Rambosek and Leach, 1987) was identified between the potential initiation codon and the N-terminal peptide. Splicing of this putative intron restored the reading frame between the proposed ATG and the N-terminal peptide amino acid sequence. By incorporating this single putative intron in the 5' end of the phytase gene, the entire polypeptide was encoded by 470 amino acids. Sequence and translation of the phytase gene is shown in FIG. 9.

FIG. 9. Nucleotide sequence from the 2.6 kb SphI fragment including the phytase gene with deduced translation. The proposed intron donor (GTRNGT)(SEQ. Id. NO. 74), lariat (RCTRAC)(SEQ. ID. NO. 75) and acceptor (YAG) consensus sequences are overlined. The nucleotide sequence corresponding to peptide #420 (Table 3) is underlined. The nucleotide sequence was determined by the M13-dideoxy method (Sanger et al., 1977) of overlapping subclones with the use of the United States Biochemical Sequenase II kit.

The relative molecular mass of the translated phytase polypeptide was calculated at approximately 51,400 daltons. A codon usage analysis of phytase revealed a frequency of G+C at silent third position of sense codons (i.e., excluding the Trp and Met codons) of 68.3%. The entire structural gene and upstream sequence was subcloned as a 2.6 kb SphI fragment into pUC-18 and designated pFF-1 (FIG. 10).

Figure 10A:
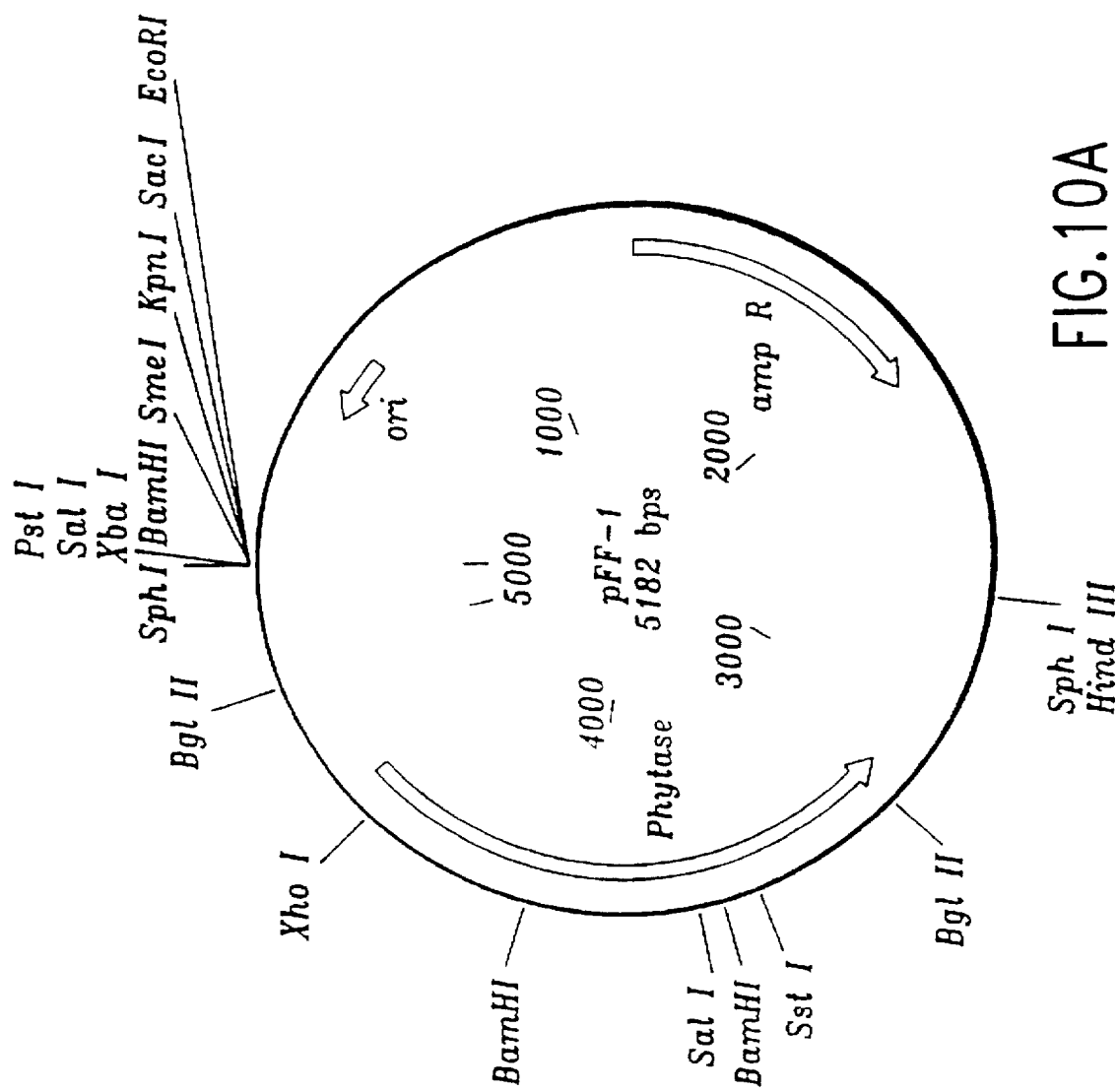
Figure 10B:
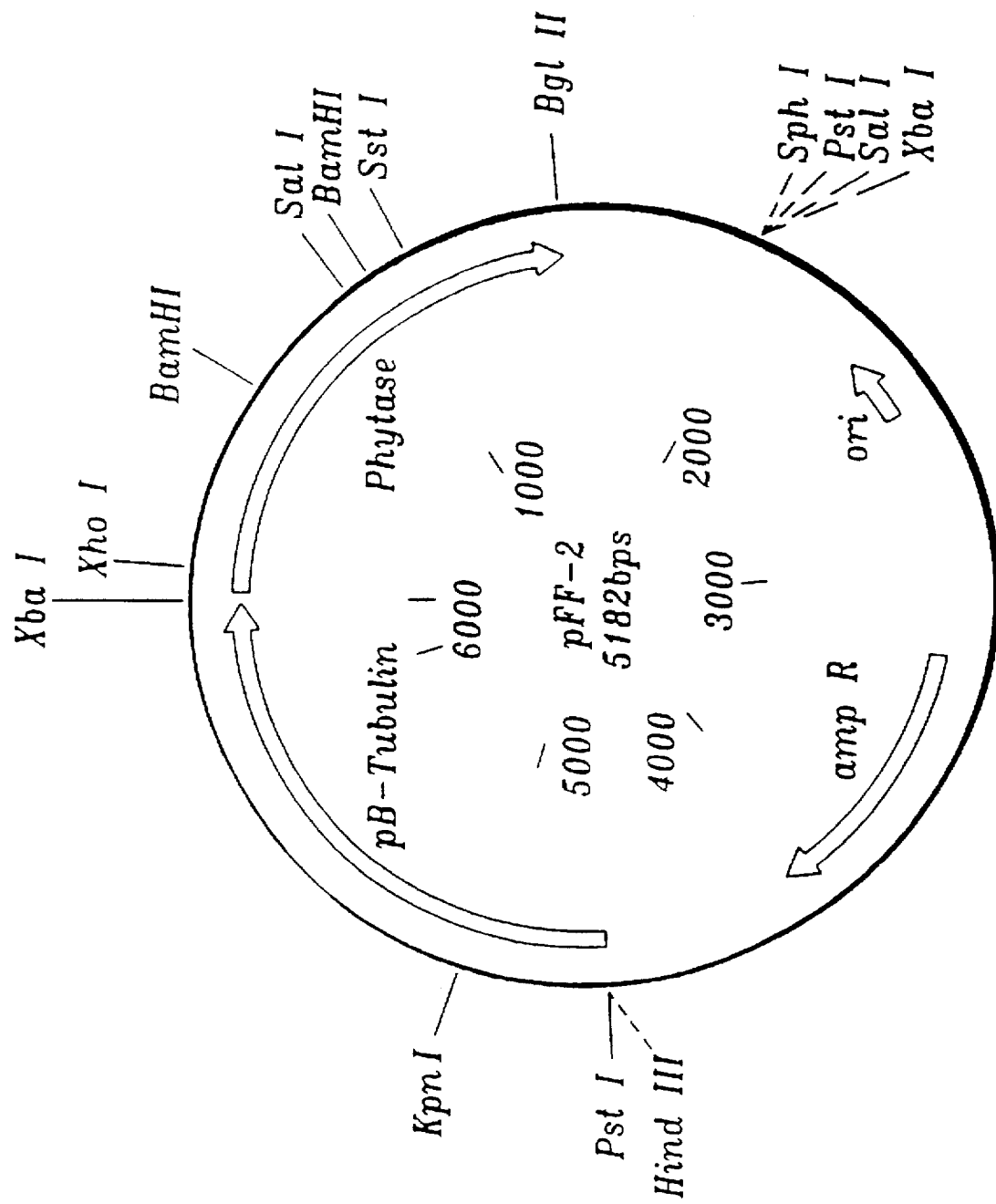
Figure 10C:
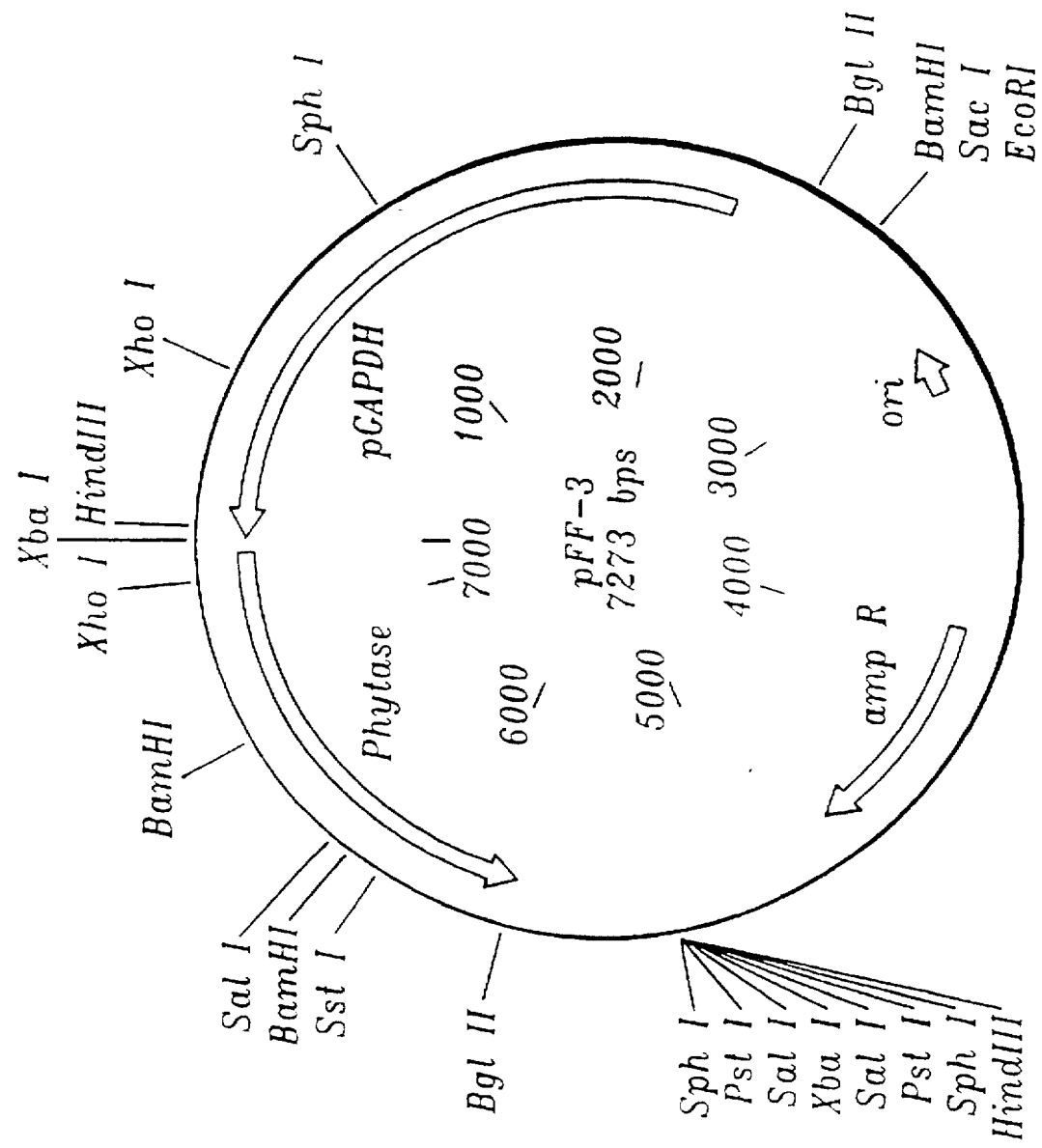
Figure 12A:
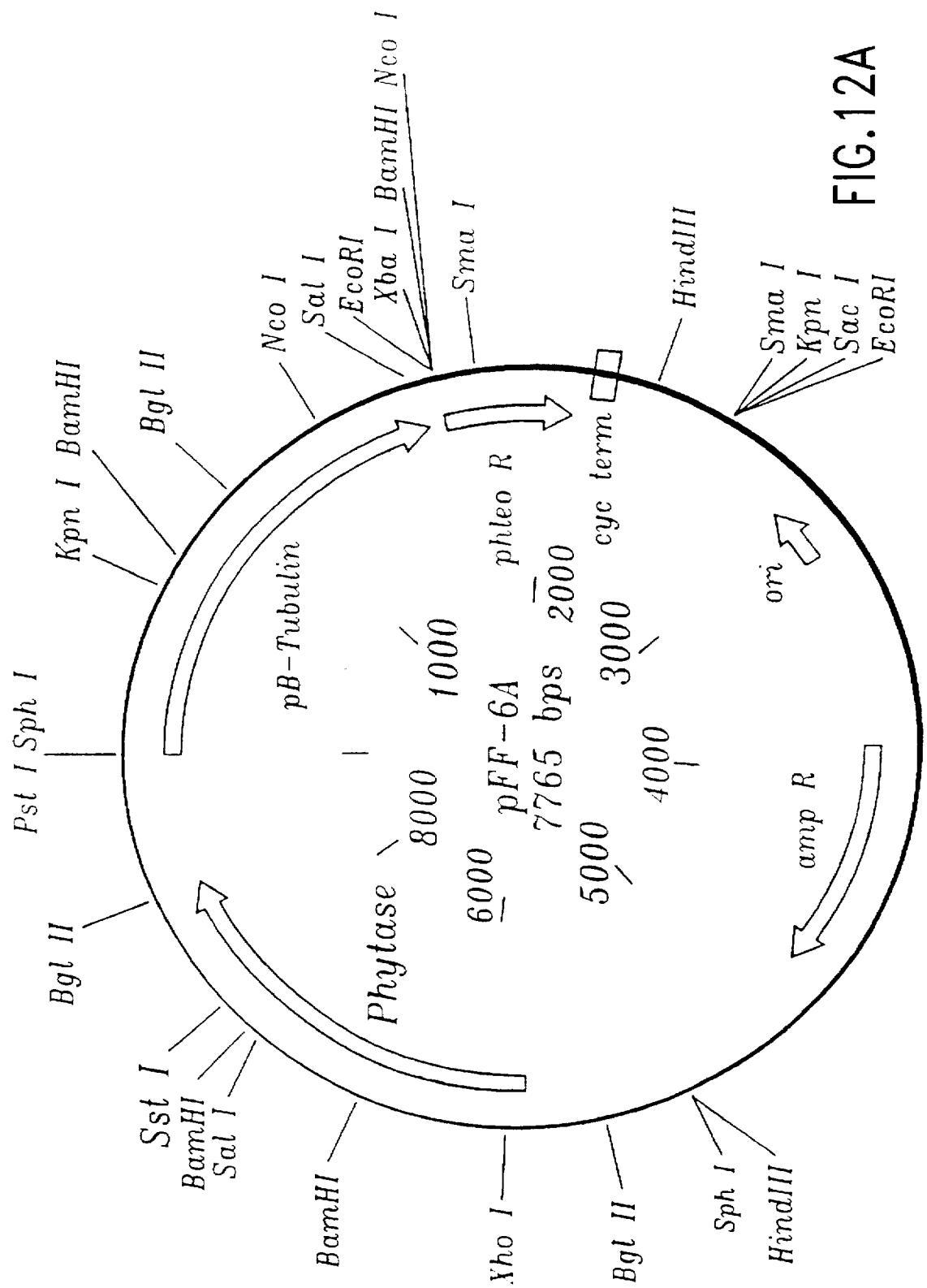
FIG. 12A, FIG. 12B, FIG. 12C and FIG. 12D shows the organization of phytase expression vector constructs pFF-6A, pFF8, pFF9, and pFF11 that were designed to remove any *E. coli* nucleotide sequences (as described in Example 4, below)
Figure 12B:
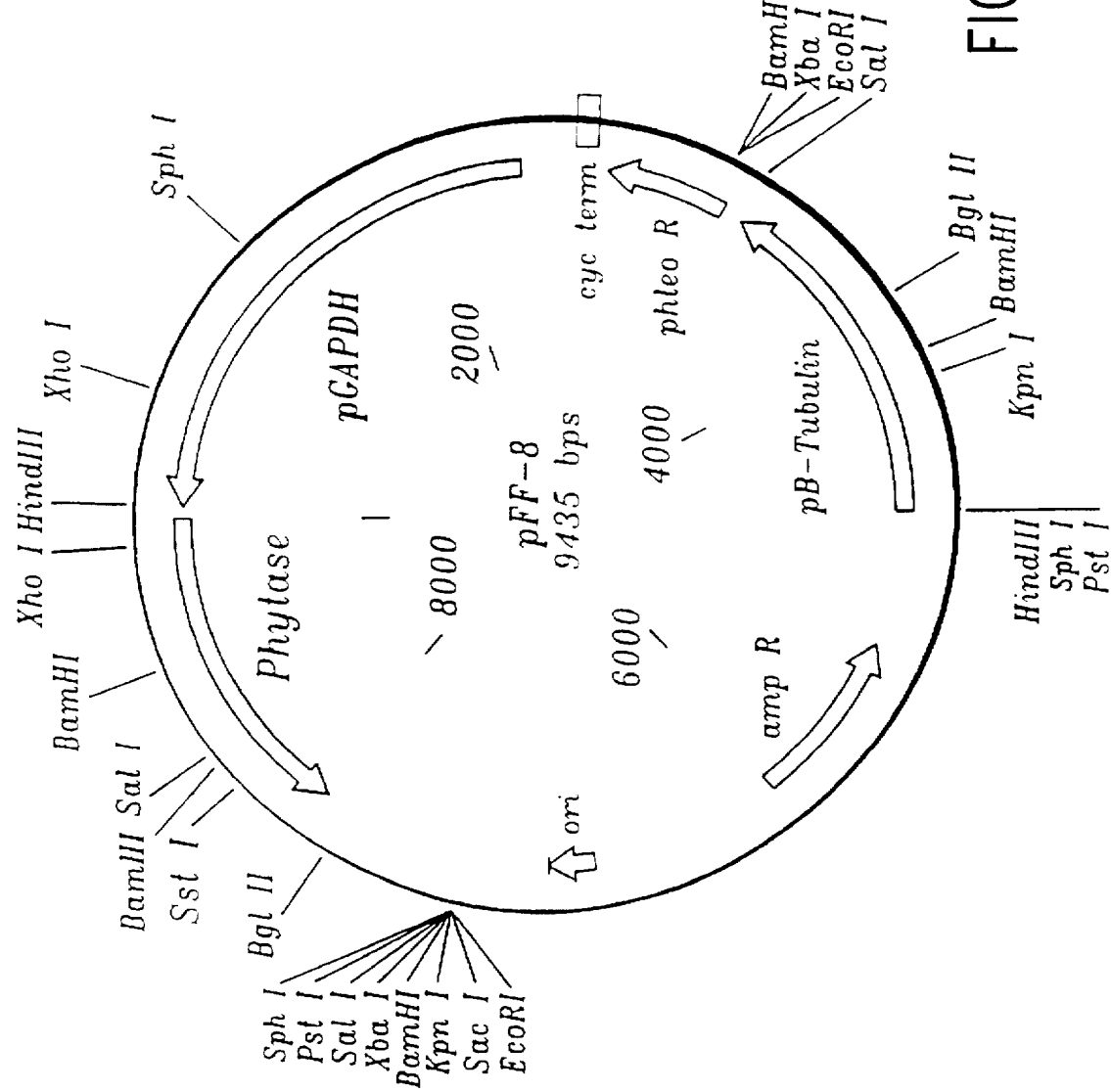
Figure 12C:
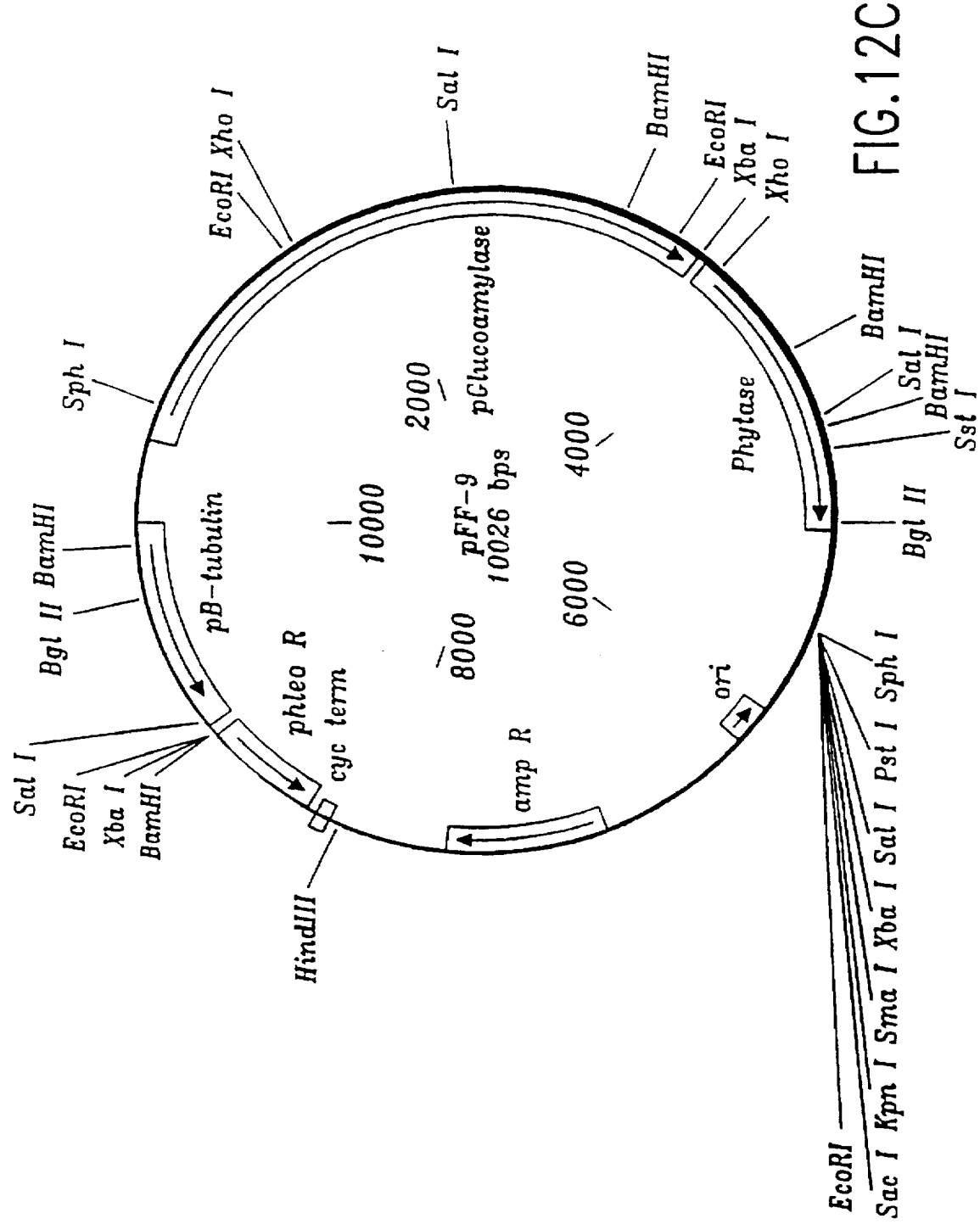
Figure 12D:
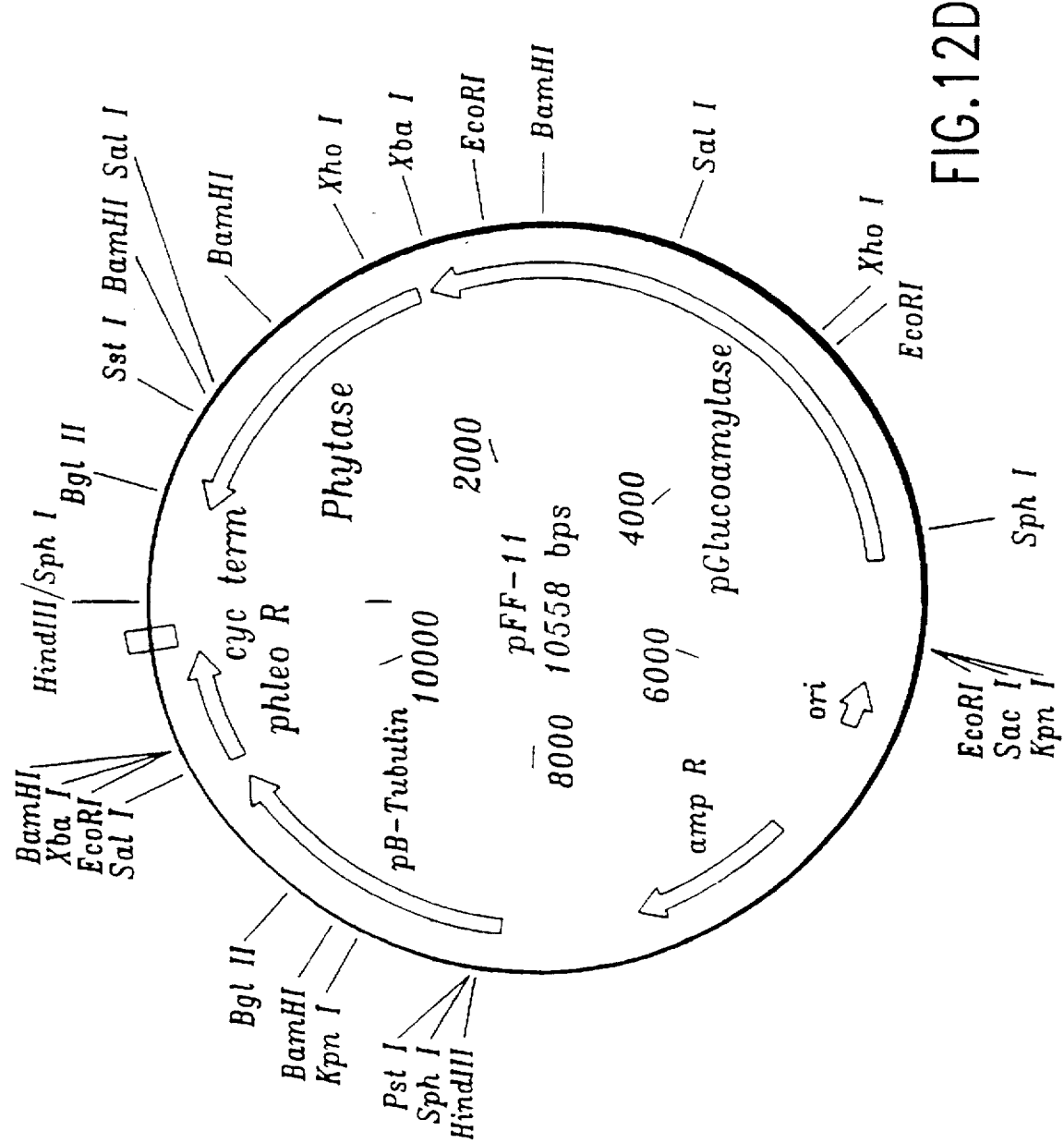
Figure 13A:
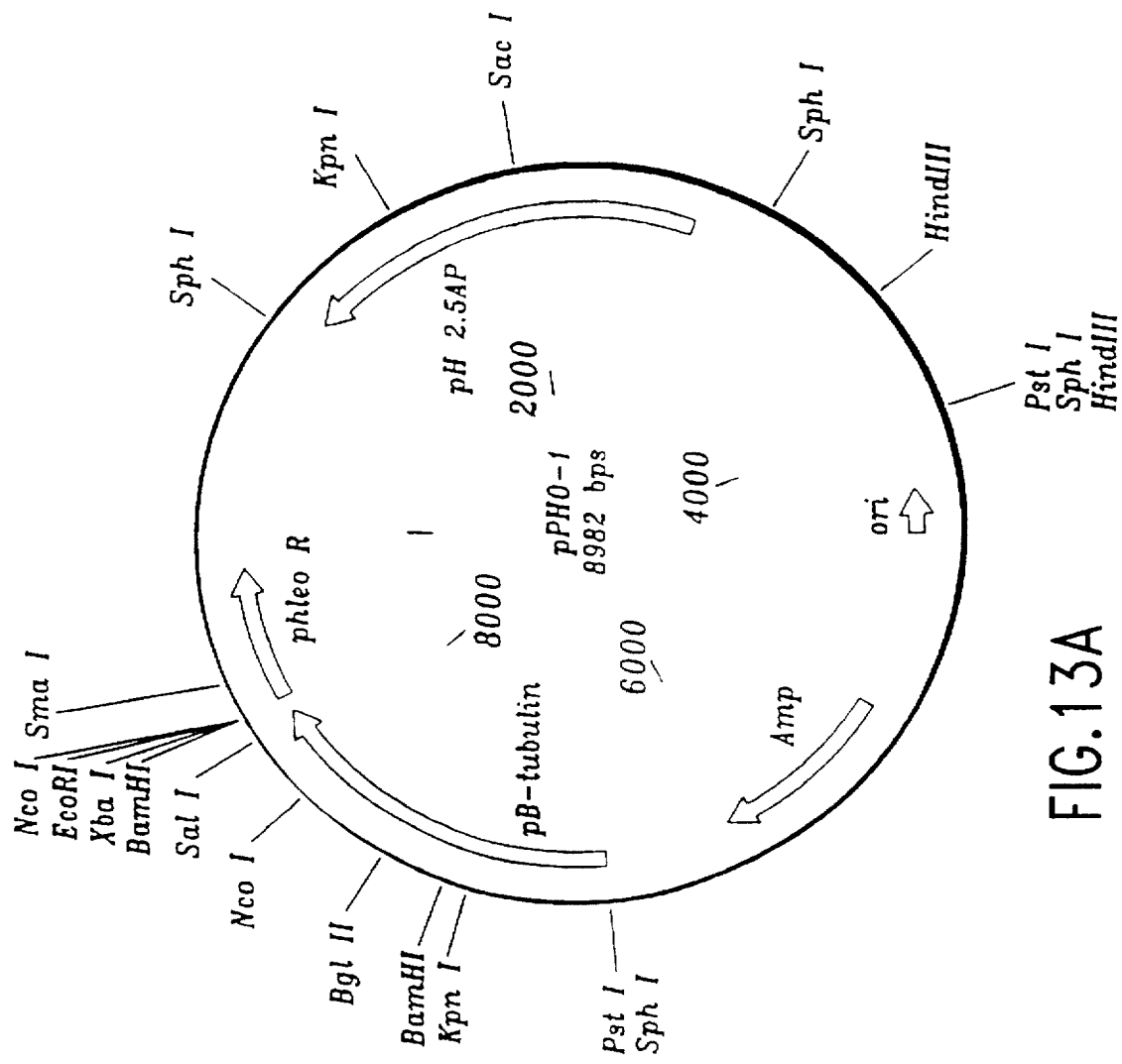
FIG. 13A, FIG. 13B, FIG. 13C and FIG. 13D shows the organization of pH2.5 acid phosphatase vector constructs pPHO-1-4A from which linear fragments can be isolated as described in Example 4, below.
Figure 13B:
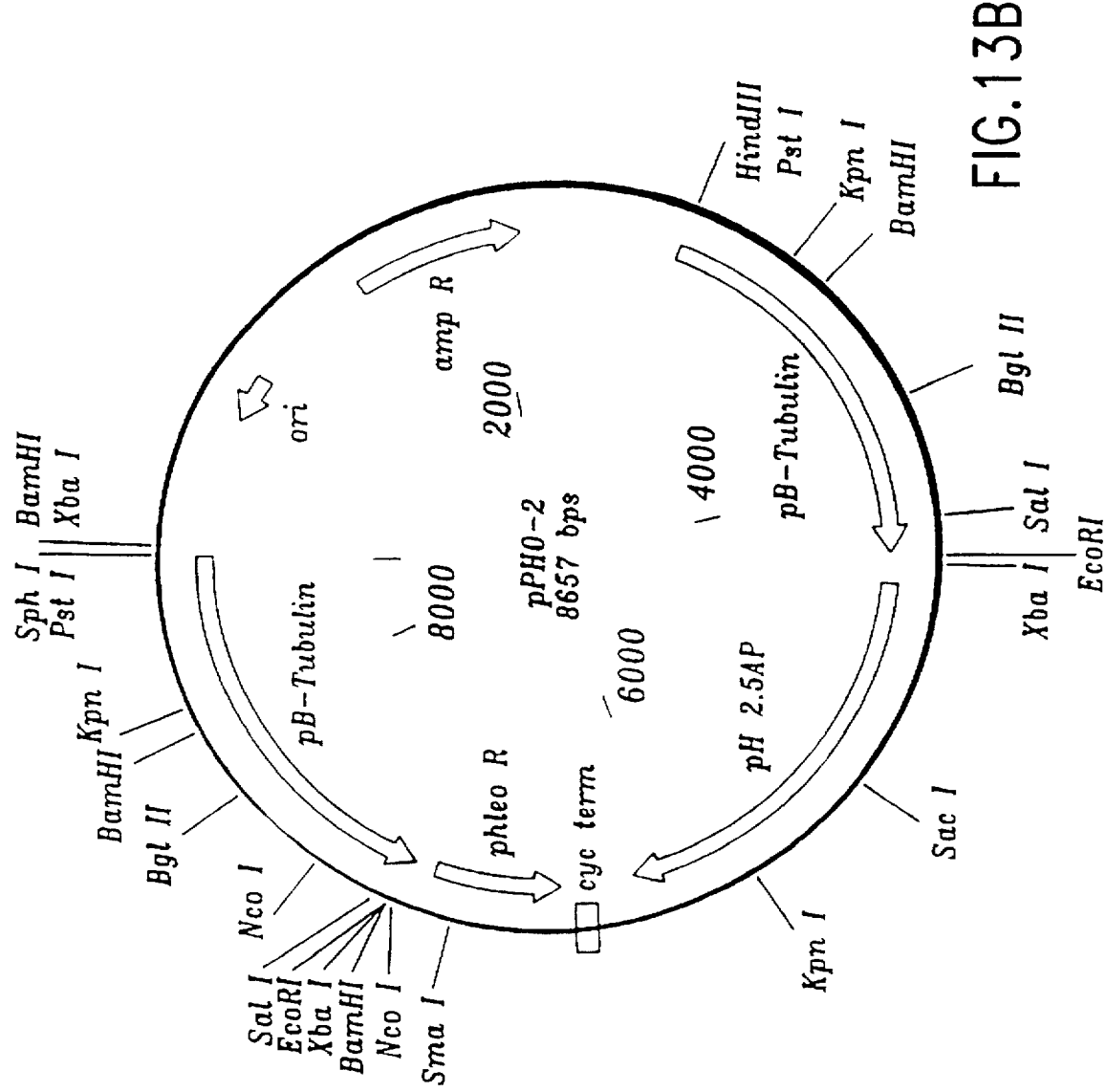
Figure 13C:
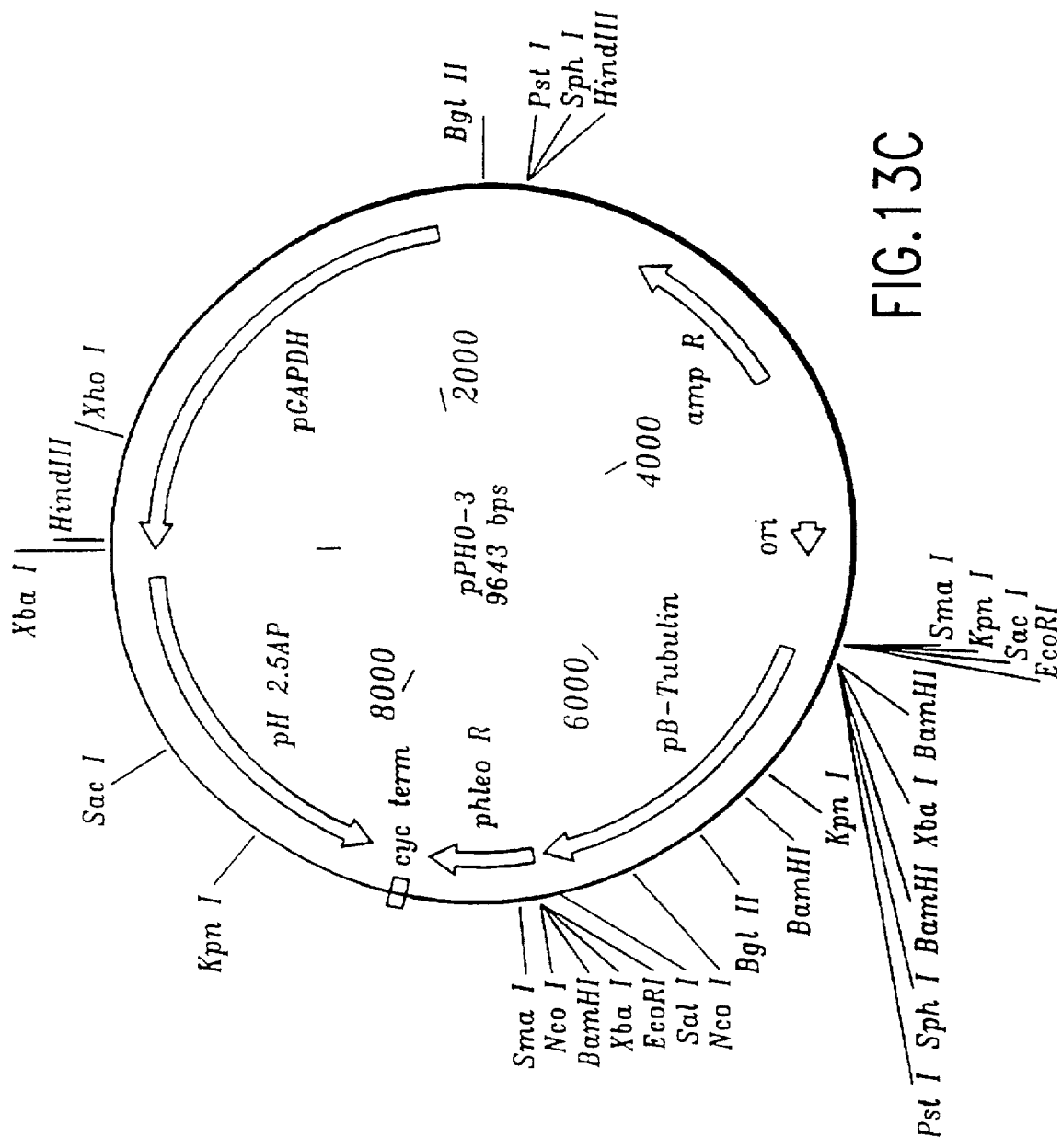
Figure 13D:
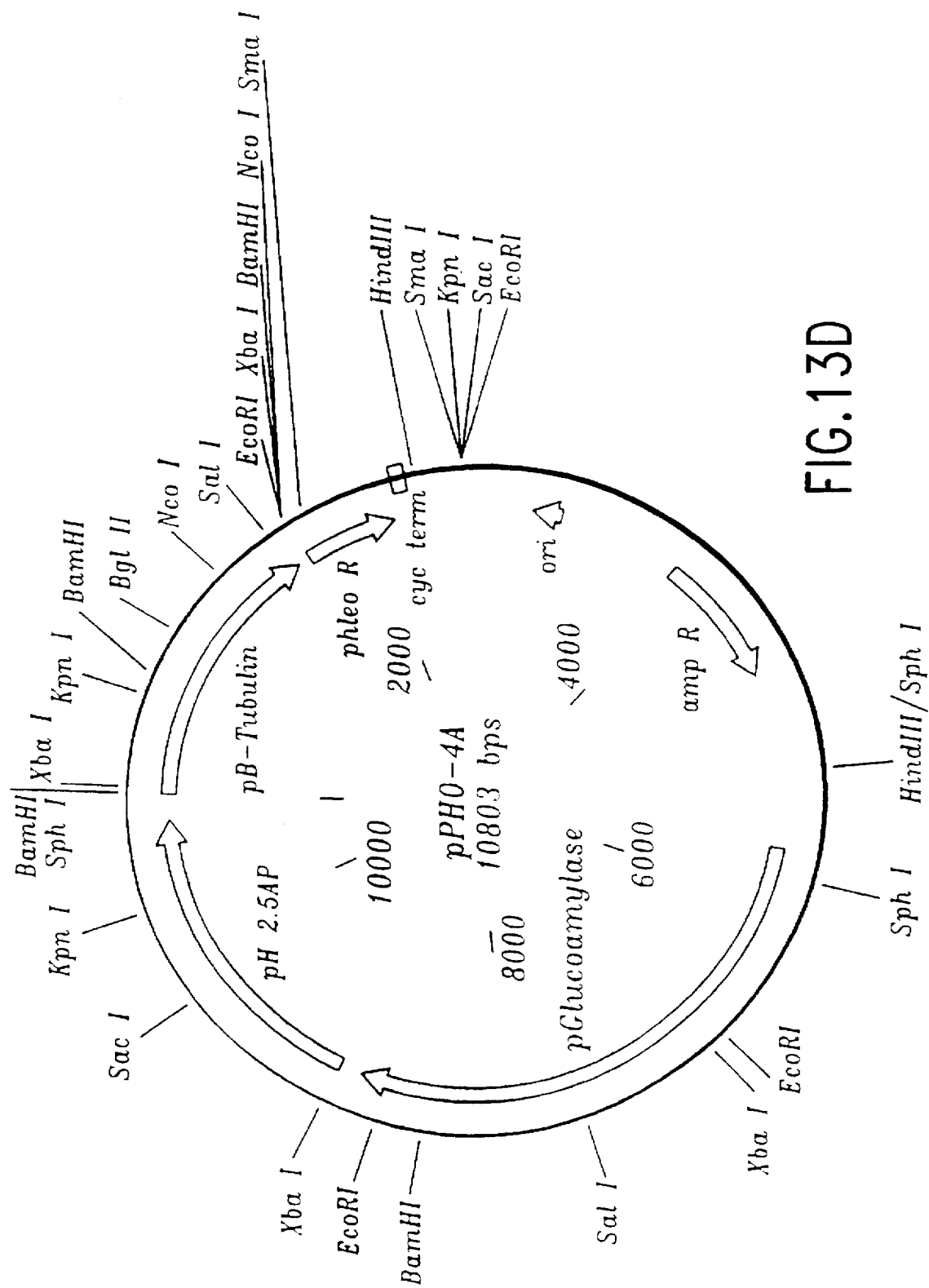

FIG. 10. Circular transformation vectors of phytase. (A) pFF-1: a 2.6 kb SphI fragment containing the phytase gene and its native promoter was subcloned from a positive lambda clone into pUC-18. An XbaI site was introduced at the −26 position of the phytase coding region in pFF-1 by site directed mutagenesis to give pSELFX. (B) pFF-2: phytase under control of the A. niger β-tubulin promoter. A 2.0 kb XbaI fragment from pSELFX was ligated to a unique XbaI site in the fungal expression vector pTL-113 to give pFF-2. (C) pFF-3: phytase under control of the A. niger GAPDH promoter. The 2.0 kb XbaI fragment from pSELFX was ligated to a unique XbaI site in pPRE-81 to give pFF-3.

(D) pFF-4: phytase under control of the A. niger GA promoter. The 2.0 kb XbaI fragment from pSELFX was ligated to a unique XbaI site in pGA to give pFF-4.

Isolation and characterization of the pH2.5 acid phosphatase gene:

The same lambda library was re-plated and screened with pH2.5 acid phosphatase oligonucleotide PHY-31 using conditions established with genomic hybridizations above. Twelve hybridizing plaques were picked for further characterization. Bacteriophage DNA isolated from each of the candidates was digested with restriction endonucleases and probed with either the PHY-31 oligo, or a second oligo mixture, PHY-34/35 that was derived from an independent pH2.5 acid phosphatase peptide (Table 5). One of the clones, AP99, contained a 2.1 kb SphI fragment previously identified in genomic Southern analysis, that hybridized strongly to both oligonucleotides. Strong hybridization to two oligonucleotides derived from independent peptide sequence strongly suggested that the clone contained pH2.5 acid phosphatase sequence. This fragment was subcloned into M13mp18 and M13mp19 for sequencing. The nucleotide sequence of this subclone revealed an ORF of 785 bp with a potential 5' initiation ATG (methionine), a fungal signal sequence, and a translated sequence compatible with the N-terminal peptide and other internal peptide sequences determined in Example 1, above (Table 4). Downstream of the ORF, termnination codons were identified in all three reading frames until nucleotide 1151, after which an additional pH2.5 acid phosphatase peptide sequence was identified. These results necessitated the inclusion of an intron(s) in the 3' portion of the gene.

Identification of cDNA clones for pH2.5 acid phosphatase:

PolyA mRNA was purified (as described, below; Materials and Methods) and used for polymerase chain reaction (PCR) cloning of a portion of pH2.5 acid phosphatase cDNA. Briefly, first strand synthesis was performed with the oligonucleotide primer AP273 which was annealed to subspecies mRNA encoding pH2.5 acid phosphatase: namely, AP273 5'-CTACCCCTCTGCATCTAG-3' (SEQ. ID. NO. 76). Oligonucleotide PCR primers UPPHOS and DOWNPHOS were synthesized with flanking EcoRI restriction sites: namely, UPPHOS 5'-GAATTCCGAGTCCGAGG-TCATGGGCGCG-3(SEQ. ID. NO. 77); and,

DOWNPHOS 5'-GAATTCCCGGGACCTACCCC-TCTGCAT-3(SEQ. ID. NO. 78).

UPPHOS and DOWNPHOS were inversely oriented and separated by 978 bases in genomic clones. PCR amplification of the cDNA-mRNA complex with oligonucleotide primers UPPHOS and DOWNPHOS yielded a specific product of approximately 850 bps. The amplified product was isolated from agarose gels and digested with EcoRI. This fragment was then subcloned into pUC-18 digested with EcoRI for double stranded sequencing.

PCR-amplified cDNA from the 3' portion of the gene was sequenced and revealed the presence of three short introns, each exhibiting consensus fungal donor, lariat and acceptor sequences. The exon sequence is derived by splicing the nucleotides 136–916, 971–1088, 1141–1245 and 1305–1740 (as shown in FIG. 11). The resultant translated sequence codes for a protein of 479 aa. The entire sequence with translation is shown in FIG. 11.

The deduced pH2.5 acid phosphatase polypeptide has a calculated molecular weight of approximately 52,700 daltons. A codon usage analysis of pH2.5 acid phosphatase revealed a very high frequency of G+C at silent third position of sense codons of 79.3%.

The 2.1 kb SphI fragment contained only 135 bp of upstream pH2.5 acid phosphatase sequence. Because this length of promoter sequence may not have been enough for efficient expression, a larger fragment was subcloned from the lambda clone. pAP-3 contains a 5.1 kb SalII/PstI fragment from lambda clone AP99 and the nucleotide sequence is shown in FIG. 11.

FIG. 11. Nucleotide sequence from the 2.1 kb SphI fragment containing the pH2.5 acid phosphatase gene with deduced amino acid translation. The intron donor, lariat and acceptor sequences as determined by cDNA sequencing are overlined. The nucleotide sequence corresponding to peptides #816 and #1110 (Table 4) is underlined. The genomic nucleotide sequence was determined by the M13-dideoxy method (Sanger et al., 1977) with the use of the United States Biochemical Sequenase II kit.

Materials and Methods:
Enzymes:

Restriction enzymes were purchased from Bethesda Research Laboratories and New England Biolabs (Beverly, Mass., USA). T4 DNA ligase, T4 DNA polymerase, T4 kinase, and the Klenow fragment from *E. coli* DNA polymerase I were purchased from BRL (Gaithersburg, Md., USA). Calf intestine phosphatase (CIP) was purchased from Boehringer Mannheim (Indianapolis, Ind., USA). Spheroplasting enzyme, Novozyme, was purchased from Novo Biolabs (Bagsvaerd, Denmark). All enzymes were used in accordance with the manufacturer's recommendations. Enzyme assay substrates phytic acid and paranitrophenylphosphate (PNPP) were purchased from Sigma (St. Louis, Mo., USA) and BMB, respectively.

Bacterial and fungal strains, plasmids and phage:

*A. niger* var. awamori strain ALKO243 (ATCC#38854) was used for isolation of the genes for phytase and pH2.5 acid phosphatase.

*E. coli* strains LE392 and P2392 and the phage Lambda Dash II, used in the construction of the *A. niger* gene bank, were obtained from Stratagene (La Jolla, Calif., USA). *E. coli* strain JM109 was used as a host in transformations with constructions derived from the plasmids pUC18 and pUC19. The phage M13mp18 and M13mp19 used in the dideoxynucleotide sequencing were obtained from Bethesda Research Laboratories (Gaithersburg, Md., USA).

Phleomycin resistant vector pLO-3, which contains the phleomycin resistance gene (a phleomycin binding protein gene from *Streptoalloteichus hindustanus*) coupled to a yeast cytochrome C1 terminator, was derived from the plasmid pUT713 (CAYLA, Toulouse Cedex, France). It is expressed in fungus by the β-tubulin promoter of *A. niger*.

General growth media:

*E. coli* JM109 was grown in L-broth. Transformants were selected on L-plates supplemented with 1.5% agar and containing 125 µg/ml ampicillin. Complete medium (CM) for growth of fungus in liquid is composed of: 50 ml of 20×Clutterbuck's salts (120 g NaNO$_3$, 10.4 g KCl, 10.4 g MgSO$_4$ 7H$_2$O, 30.4 g KH$_2$PO$_4$), 2.0 ml Vogel's Trace Elements (0.3M citric acid, 0.2M ZnSO$_4$, 25 mM Fe(NH$_4$)$_2$(SO$_4$)$_2$·6H$_2$O, 10 mM CuSO4, 3 mM MnSO$_4$·H$_2$O, 8 mM boric acid, 2 mM Na$_2$MoO$_4$·2H$_2$O), 5.0 g tryptone, 5.0 g yeast extract, 10 g glucose, in one liter of distilled water. *A. niger* strains ALKO243 and ALKO2268 were grown on PD agar slants (2.4% Potato Dextrose Broth [Difco #0549]; 1.5% Agar [Difco #0140]) for seven to twelve days at 28° C.

Isolation of genomic DNA from *A. niger* var. awamori strain ALKO243:

One slant of ALKO243 grown on PDA for 5 days at 35° C. was soaked with 5 ml of NP-40 H$_2$O (0.005% (v/v) Nonidet P40 detergent). Spores were scraped from slants andmacerated in glass tubes with 3 mm glass beads. 1×10$^8$ spores were used to inoculate 500 ml CM in a 2-liter flask. Cultures were grown at 35° C. with shaking at 200 RPM for 48 hours. Mycelia were collected on mira-cloth, frozen in liquid nitrogen and lyophilized overnight. All of the frozen dried mycelia (approximately 2.0 grams) were ground with sea sand in a mortar chilled with liquid nitrogen. Ground mycelia were transferred to a 250 ml centrifuge bottle and resuspended in 30 ml 4% SDS-TE buffer (10 mM Tris Base, 1 mM EDTA, 4% SDS) and allowed to lyse at room temperature for 1 hour. Cell debris were removed by centrifugation at 4000×g for 5 minutes and the supernatant was removed to a 30 ml centrifuge tube. The samples were extracted twice with an equal volume of Tris-saturated phenol:chloroform (1:1) each time removing the aqueous phase to a clean tube. DNA was precipitated by adding 10% (v/v) 5M NH$_4$OAc and 2.5 volumes of EtOH, and incubating overnight at −80° C. The preparation was thawed at room temperature until "syrupy" and was centrifuged at 12000×g for 30 minutes at 4° C. The supernatant was removed and the pellet dissolved in 19 ml TE (10 mM Tris Base, 1 mM EDTA) with gentle pipeting, to which was added 19.0 g CsCl. Two 11.5 ml ultracentrifuge tubes were filled with DNA in TE+CsCl, 0.9 ml of 10 mg/ml ethidium bromide was added and the mixture was centrifuged at 45,000 RPM (20° C.) for 22 hours in a Sorvall T865.1 rotor. Banded genomic DNA was visible under UV light and collected through an 18 m gauge hypodermic needle. Ethidium was removed by extraction with NaCl saturated isopropanol. CsCl was removed by dialysis against TE. DNA was precipitated with ethanol in 0.3M NaOAc.

Construction of genomic gene bank:

Genomic DNA from *A. niger* var. awamori strain ALKO243 was cut with Sau3A in order to produce fragments 10–23 kb in length. Cut DNA was ligated to purchased BamHI cut dephosphorylated Lambda Dash II vector arms. The ligation was packaged in vitro using Stratagene Gigapack Gold packaging extracts. Packaged phage was used to infect *E. coli* strain P2392 to obtain plaques.

Screening the gene bank with oligonucleotides:

Plaques were lifted onto Schleicher & Schuell NC (BA85) nitrocellulose membranes as recommended by the manufacturer. Using the amino acid sequences from phytase and pH2.5 acid phosphatase (Example 1, above), degenerate oligonucleotides were prepared for each protein. The oligonucleotide mixture for each protein was complementary to all possible codon combinations of the chosen region of the peptide. Oligonucleotides were synthesized using the Pharmacia Gene Assembler Plus and the sequences are shown in Table 5, above.

Isolation of Lambda DNA:

Single isolated hybridizing plaques were picked into 500 ml SM (per liter: 5.8 g NaCl, 2.0 g MgSO$_4$, 50 ml 1M Tris-HCl, pH7.5; 5 ml 2% (w/v) gelatin solution). 20 ml chloroform was added and phage particles were eluted overnight at 4° C. 220 ml of cell lysate was mixed with 200 ml LE392 cells grown in the presence of Mg and maltose; 8 ml NZCYM media (10.0 g NZ-amine, 5.0 g NaCl, 5.0 g yeast extract, 2.0 g MgSO$_4$·7H$_2$O, and 1.0 g Casamino acids per liter; pH adjusted to pH7.5) was added; and, the culture was grown with shaking at 37° C. until cells lysed (about 6 hours). 100 ml chloroform was then added and incubation was continued for 15 minutes to ensure complete lysis. The sample was then centrifuged 5 min at 8000 g and the supernatant was removed to fresh tube. RNAse A and DNAse I were added to 1 mg/ml each; the samples were incubated for 30 minutes at 37° C; and, an equal volume of 20% (wv) PEG 8000, 2M NaCl in SM was added to precipitate the phage. Samples were incubated for at least 1 hour on ice. The resultant phage were pelleted by centrifuging 10,000×g for 20 minutes at 4° C.; the supernatant was decanted; and, the phage pellet was resuspended in 0.5 ml SM. DNA was purified further by addition of SDS, EDTA and Proteinase K, followed by extraction with phenol:chloroform and isopropanol precipitation. The sizes of the lambda DNA inserts were then examined on 0.8% agarose gels, the DNA was blotted to nitrocellulose and hybridized with the radiolabelled oligonucleotide PHY-1 or PHY-31 probes. DNA fragments that hybridize to the probes and had a size identical to genomic DNA fragments were chosen for subcloning.

Isolation of total RNA from *A. niger*:

Three 200 ml cultures of *A. niger* var. awamori ALKO243 were grown in RNA broth media (2% corn starch [Sigma], 1% proteose peptone [Difco], 30 g/l glucose, 5 g/l NH$_4$NO$_3$, 0.5 g/l MgSO$_4$·7H$_2$O, 0.5 g/l KCl, 0.183 gl FeSO$_4$·7H$_2$O) for 48 hours at 30° C., 220 RPM. The mycelia were filtered through Whatman filter paper #1 and rinsed with 10 ml of DEPC-treated H$_2$O (0.1% diethyl pyrocarbonate in sterile distilled water), then lyophilized overnight at −80° C. 1.5 grams (3 g total) of dried mycelia was crushed under liquid nitrogen into a fine powder, then transferred to a centrifuge tube containing 10 ml of Breaking Buffer (50 mM Tris-HCl pH7.4, 150 mM NaCl, 5 mM EDTA pH8, 5% SDS) and 10 ml of phenol/chloroform/isoamyl alcohol (P/CIA: 50:48:2). The mixture was allowed to thaw for thirty minutes at room temperature and was then centrifuged for 10 minutes at 10,000 RPM at 4° C. The aqueous layer was removed using a wide bore pipette into a clean centrifuge tube and re-extracted with P/CIA until the interface was clear. An equal volume of 6M LiCl was added to the final aqueous layer to precipitate the RNA and chilled overnight at −80° C. The mixture was then centrifuged for twenty minutes at 10,000×g and 4° C., and the pellet was resuspended in 2.4 ml of GTC solution (4M Guanidine thiocyanate, 25 mM Sodium citrate pH7, 5% N-lauryl sarcosine, 100 mM b-mercaptoethanol). An equal volume of isopropanol was added, the precipitate was chilled on dry ice for 40 minutes, and then centrifuged at 4° C. for 30 minutes. The pellet was rinsed in 80% EtOH, re-spun, vacuum dried, and finally resuspended in 1 ml of DEPC-H$_2$O. The concentration of RNA was determined spectrophotometrically at 260 nm.

Isolation of mRNA:

Polyadenylated messenger RNA (polyA mRNA) was affinity purified from total RNA using oligo(dT)-cellulose columns according to the manufacturers instructions (Pharmacia Fine Chemicals, Piscatawy, N.J.). Briefly, 1.25 mg of total RNA was applied to two separate columns that were previously subjected to centrifugation and equilibration in High-salt buffer (Pharmacia). After three washes in Low-salt buffer (Pharmacia), the mRNA was eluted from the column at 65° C. in prewarmed Elution Buffer (10 mM Tris-HCL, pH7.4, containing 1 mM EDTA); and precipitated by adding 0.1 volume of 10 mg/ml glycogen and 2.5 volumes of ethanol. The mixture was chilled at −80° C. for 2 hours, then centrifuged at 4° C. for 30 minutes. The recovered MRNA was dissolved in Elution Buffer to a final concentration of 1.3 mg/ml.

PCR isolation of pH2.5 acid phosphatase cDNA:

First strand synthesis was performed with the BMB cDNA kit according to manufacturers' recommendations with 1.0 mg mRNA and oligonucleotide primer AP273, synthesized complementary to 3' pH2.5 phosphatase nucleotide sequence: namely, AP273 5'-CTACCCCTCTGCATCTAG-3'(SEQ. ID. NO. 76). Oligonucleotide PCR primers UPPHOS and DOWNPHOS were synthesized with flanking EcoRI restriction sites: namely, UPPHOS  5'-GAATTCCGAGTCCGAGG-TCATGGGCGCG-3'(SEQ. ID. NO. 77); and,

DOWNPHOS 5'-GAATTCCCGGGACCTACCCC-TCTGCAT-3'(SEQ. ID. NO. 78), as described above.

Subcloning and sequencing of phytase and pH2.5 acid phosphatase clones:

Hybridizing restriction fragments of lambda genomic clones were gel purified using the "Glassmilk Purification Kit" available commercially from GeneClean (Bio 101, La Jolla, Calif.). The restriction fragments were subcloned into M13mp-18 and M13mp-19 cut with the appropriate enzymes. The nucleotide sequence of clones reacting positively with oligonucleotide probes for phytase and pH2.5 acid phosphatase was determined by the M13-dideoxynucleotide sequencing method (Sanger et al., *Proc. Nat. Acad Sci. USA* 74:5463–5467, 1977) using the United States Biochemical Sequenase II kit. cDNA was sequenced in regions of suspected introns by alkaline denaturation double stranded sequencing. The phytase gene was completely contained within a 2.6 kb SphI fragment that was subcloned into pUC-18 to give pFF-1. The complete pH2.5 acid phosphatase gene was isolated as a 2.1 bp SphI fragment that was subcloned into pUC-18 to give pAP-1.

pSELFX, is a plasmid containing a phytase nucleotide sequence in which an XbaI site was introduced into the gene sequence by modifying the nucleotides at position −26 and −24 relative to the ATG start codon. The nucleotide changes were introduced by site-specific mutagenesis of the 2.6 kb SphI fragment containing the phytase gene, using the Promega Altered Sites Mutagenesis Kit. The oligonucleotide used for directing mutagenesis is shown below: namely, Oligo PHY-40: 5'-AGAAGAAATT<u>TCTAGA</u>ACAGCAGCGATTGG-3'

(XbaI)

pAP-1Xba is a plasmid containing a pH2.5 acid phosphatase nucleotide sequence in which an XbaI site was introduced into the gene sequence by modifying the nucleotides at positions −24 and −27 relative to the ATG start codon. The nucleotide changes were introduced by PCR-mutagenesis. The primers for PCR-mutagenesis are shown below: namely, Oligo #271 5'-CGAGAGCACCTT<u>CTCTAGA</u>TTTTGTCAAATGTACC-3' (SEQ. ID. NO. 80)

(XbaI)

and,

Oligo #272 5'-ACCCTCACCGAACTTGCGGGCCG-3' (SEQ. ID. NO. 81)

pAP-1 DNA was used as a template for PCR amplification. The resulting amplified fragment was cleaved with XbaI and NruI and the fragment was then ligated to XbaI/NruI cut pAP-1 to give plasmid pAP-1Xba. The plasmid was sequenced to insure that no mutations were introduced into the region which had been PCR amplified. pAP-2 was generated by ligating the BamHI/HindIII fragment treated with Klenow reagent from pAP-1XBA into SmaI cut pUC-18. Transformants containing the correctly oriented pAP-2 were identified by analysis of the size of restriction endonuclease fragments.

The entire structural gene for pH2.5 acid phosphatase was removed from pAP-2 as a 2.0 kb XbaI fragment for construction of pH2.5 acid phosphatase transformation vectors that over-expressed the subject enzyme (Example 4, below). The complete pH2.5 acid phosphatase gene was also isolated as a 5.0 kb PstI/SalI fragment that was subcloned into pUC-18 to give pAP-3. pAP-3 was used in the construction of pH2.5 acid phosphatase transformation vectors for over-expressing the subject enzyme (Example 4, below).

Northern blotting procedure:

Ten and twenty mg amounts of total RNA (isolated as above) were applied to wells of a 1.5% agarose-formaldehyde gel and separated by electrophoresis. RNA molecular weight markers (0.24 kb–9.5 kb "RNA Ladder," Bethesda Research Labs) were also applied to the gel for size comparisons. The gel was blotted onto nitrocellulose (Schleicher and Schuell; Keene, NH), baked for one hour at 80° C. in a vacuum oven, prehybridized in 50% formamide, 5X SSC, 0.1% SDS, 5×Denhardt's and 100 mg/ml calf thymus DNA at 37° C. for 24 hours, then hybridized in the same solution with radiolabelled probe at 42° C. for 24 hours. The filter was washed twice in 2×SSC/0.1% SDS at room temperature for fifteen minutes, then once in 0.1×SSC/ 0.1% SDS and autoradiographed using Kodak S-Omat AR film with intensifying screens.

EXAMPLE 3

Homology With Other Phosphatases

A comparison was made between the amino acid sequence of the pH2.5 acid phosphatase and phytase and other published acid phosphatase sequences. Homology (alignment score of 17.705) was determined using the PC/GENE matrix program PCOMPARE (based on the method of Neddleman and Wunsch, 1970). Significant homology was found between the pH2.5 acid phosphatase and other acid phosphatase enzymes "PHO-3" (Bajwa, et al., 1984) and "PHO-5" (Arima, et al., 1983), both isolated previously by others from Saccharomyces cerevisiae. The area of highest homology, R H G X R X P (SEQ. ID. NO. 82)(aa positions 81–87), was used to search the EMBL CDPROT17 protein database release 1991. The RHGXRXP (SEQ. ID. NO. 82) sequence was found in several other acid phosphatases (as shown in Table 6.

TABLE 6

Homology of phytase and pH2.5 Acid Phosphatase with Other Acid Phosphatase[a]

| Organism | Gene Name[b] | Amino Acid Sequence | | | | | | | | | | | | | | SEQ ID NO. |
|---|---|---|---|---|---|---|---|---|---|---|---|---|---|---|---|---|
| A. niger | Phytase | A | Q | V | L | S | R | H | G | A | R | Y | P | T | E | S | K | G | K | (SEQ ID NO. 83) |
| A. niger | pH2.5 AP | V | I | M | V | K | R | H | G | E | R | Y | P | S | P | S | A | G | K | (SEQ ID NO. 84) |
| E. coli | APPA | V | V | I | V | S | R | H | G | V | R | A | P | T | K | A | T | Q | L | (SEQ ID NO. 85) |
| Yeast | PHO-1 | V | H | T | L | Q | R | H | G | S | R | N | P | T | G | G | N | A | A | (SEQ ID NO. 86) |
| Yeast | PHO-5 | L | Q | M | V | G | R | H | G | E | R | Y | P | T | V | S | L | A | K | (SEQ ID NO. 87) |
| Yeast | PHO-3 | L | Q | M | L | A | R | H | G | E | R | Y | P | T | Y | S | K | G | A | (SEQ ID NO. 88) |
| Rat | LAP | V | T | L | L | Y | R | H | G | D | R | S | P | V | K | A | Y | P | K | (SEQ ID NO. 89) |
| Rat | PAP | V | T | L | V | F | R | H | G | D | R | G | P | I | E | T | F | P | N | (SEQ ID NO. 90) |
| Human | ACP2 | V | T | L | L | Y | R | H | G | D | R | S | P | V | K | T | Y | P | K | (SEQ ID NO. 91) |
| Human | ACPP | V | T | L | V | F | R | H | G | D | R | S | P | I | D | T | F | P | T | (SEQ ID NO. 92) |

[a]Homology with other acid phosphatases found using the target sequence R H G X R X P with IntelliGenetics PC/GENE program QGSEARCH on the EMBL CDPROT17 protein database using default search parameters; BOLD residues are identical;
[b]APPA = A pH2.5 acid phosphatase from E. coli ([Touati and Danchin, 1987]; PHO-1 = An acid phosphatase from Scizosaccharamyces pombe ([Elliot et al., 1986]); PHO-5 = repressible acid phosphatase from Saccharomyces cerevisiae ([Arima et al., 1983]); PHO-3 = non-repressible acid phosphatase from S. cerevisiae ([Bajwa et al., 1984]); LAP = rat lysosomal acid phosphatase ([Himeno et al., 1989]); PAP = a rat prostatic acid phosphatase ([Roiko et al., 1990]); ACP2 = a human lysosomal acid phosphatase ([Pohlmann et al., 1988]); ACPP = a human prostatic acid phosphatase ([Tailor et al., 1990]).

The RHGXRXP region is conserved between organisms as diverse as E. coli and humans. This conservation suggests functional significance and thus may reflect an active site region of these phosphatases.

EXAMPLE 4

Over-Expression Of Recombinant Phytase And ph2.5 Acid Phosphatase In Aspergillus Niger

[General materials and methods are described in the section entitled "Materials and Methods," which follows this example.]

Construction of expression vectors phytase:

A number of vectors were designed for the reintroduction of phytase and pH2.5 acid phosphatase using both native and alternative fungal promoters. One set of vectors carrying the phytase gene, pFF1-pFF4 (FIG. 10, above), contained no fungal selectable marker and were introduced by co-transformation with the plasmid pLO3 (see Materials and Methods, below).

Recombinant strains resulting from vectors pFFI-2 contained foreign DNA sequences derived from the E. coli selectable marker. Therefore, a second set of vectors termed pFF6-pFF11 was designed to remove these sequences. The latter vectors contained a fungal selectable marker and restriction sites allowing linear fragments to be isolated free of E. coli sequences (FIG. 12).

FIG. 12. Linear transformation vectors of phytase. (A) pFF-6A: phytase under control of its native promoter. The 2.6 kb SphI fragment from pFF-1 was cloned into the SphI site of pLO3 to give pFF-6, was isolated as a linear 4.9 kb HindIII fragment. (B) pFF-8: phytase under control of the GAPDH promoter. The phleomycin resistance cassette from pLO3 was isolated as a HindIII (filled)/PstI fragment and subcloned into BglII (filled)/PstI cut pPRE-81 to give pPRE-82. The pSELFX XbaI fragment containing phytase was added to pPRE-82 partially cut with XbaI to give pFF-8, that was isolated as a 6.7 kb PstI fragment. (C)pFF-9: phytase under control of the GA promoter. The phleomycin resistance cassette from pLO3 was isolated as a KpnI (filled)/HindIII fragment and ligated to pFF-4 partially cut with KpnI. blunted, then cut with HindIII. pFF-9 was isolated as a 7.3 HindIII/KpnI linear fragment. (D)pFF-11: phytase under control of the GA promoter and signal sequence. Oligos #260 and #261 (see Materials and Methods, below) were annealed and ligated to XbaI/XhoI digested pFF-1, the GA promoter added as a KpnI/XbaI fragment, and the phleomycin resistance marker (Phleo$^r$) cassette was added as a HindIII fragment to give pFF-11. Linear DNA was isolated as a 7.35 KpnI fragment.

Construction of expression vectors: pH2.5 acid phosphatase with and without phytase:

Transformation vectors for pH2.5 acid phosphatase consisted of linear vectors, termed pPHO1-pPHO4A, that were constructed for introduction of the pH2.5 acid phosphatase gene (FIG. 13). Two vectors, pFIN-1A and pFIN-1B, were also engineered to contain both the phytase and pH2.5 acid phosphatase genes expressed from the glucoamylase promoter in a single plasmid (FIG. 14).

FIG. 13. Vectors from which linear fragments can be isolated for the reintroduction of pH2.5 acid phosphatase. (A) pPHO-1: pH2.5 acid phosphatase under control of its native promoter. The phleo$^r$ cassette was isolated as a HindIII fragment, blunt-ended, and ligated to pAP-3 (the pH2.5 acid phosphatase gene in a 5.0 kb PstI/SalI fragment in pUC-18 (5)), cut with EcoRI and also blunt-ended. Linear DNA was isolated as a 6.3 kb PstI fragment. (B) pPHO-2: pH2.5 acid phosphatase under control of the b-tubulin promoter. The pH2.5 acid phosphatase gene contained in a 2.0 kb XbaI fragment from pAP-1Xba (Materials and Methods, below) was subcloned into pTL-113, which was then partially cut with SphI, filled, and ligated to a fragment containing the phleomycin-resistance marker cassette, yielding pPHO-2. (C) pPHO-3: pH2.5 acid phosphatase under control of the GAPDH promoter. pPHO-2 was partially digested with XbaI to give a 4.3 kb XbaI fragment containing pH2.5 acid phosphatase and the phleo$^r$ cassette, which was the ligated into the XbaI site of pPRE-81. (D) pPHO-4A: pH2.5 acid phosphatase under control of the GA promoter. The 2.0 kb Xba fragment from pAP-1Xba was subcloned into pGA, and a 5.5 kb KpnI fragment containing the GA promoter and pH2.5 acid phosphatase was isolated and filled in and then ligated into pLO3.

Figure 14A:
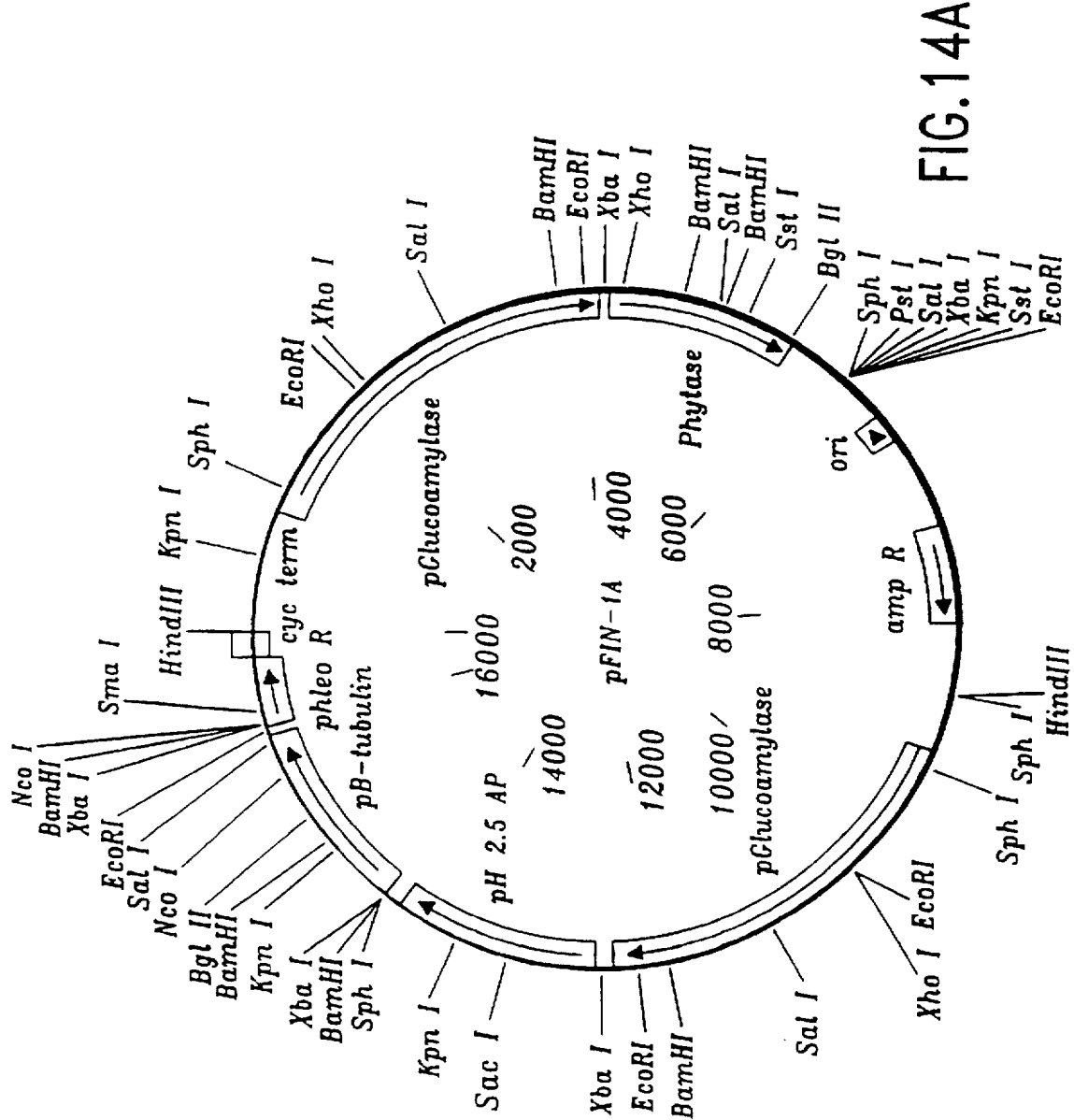
FIG. 14A and FIG. 14B shows the organization of two transformation vectors having both the pH2.5 acid phosphatase gene and phytase gene, namely, pFIN-1A and pFIN-1B (as described in Example 4, below)
Figure 14B:
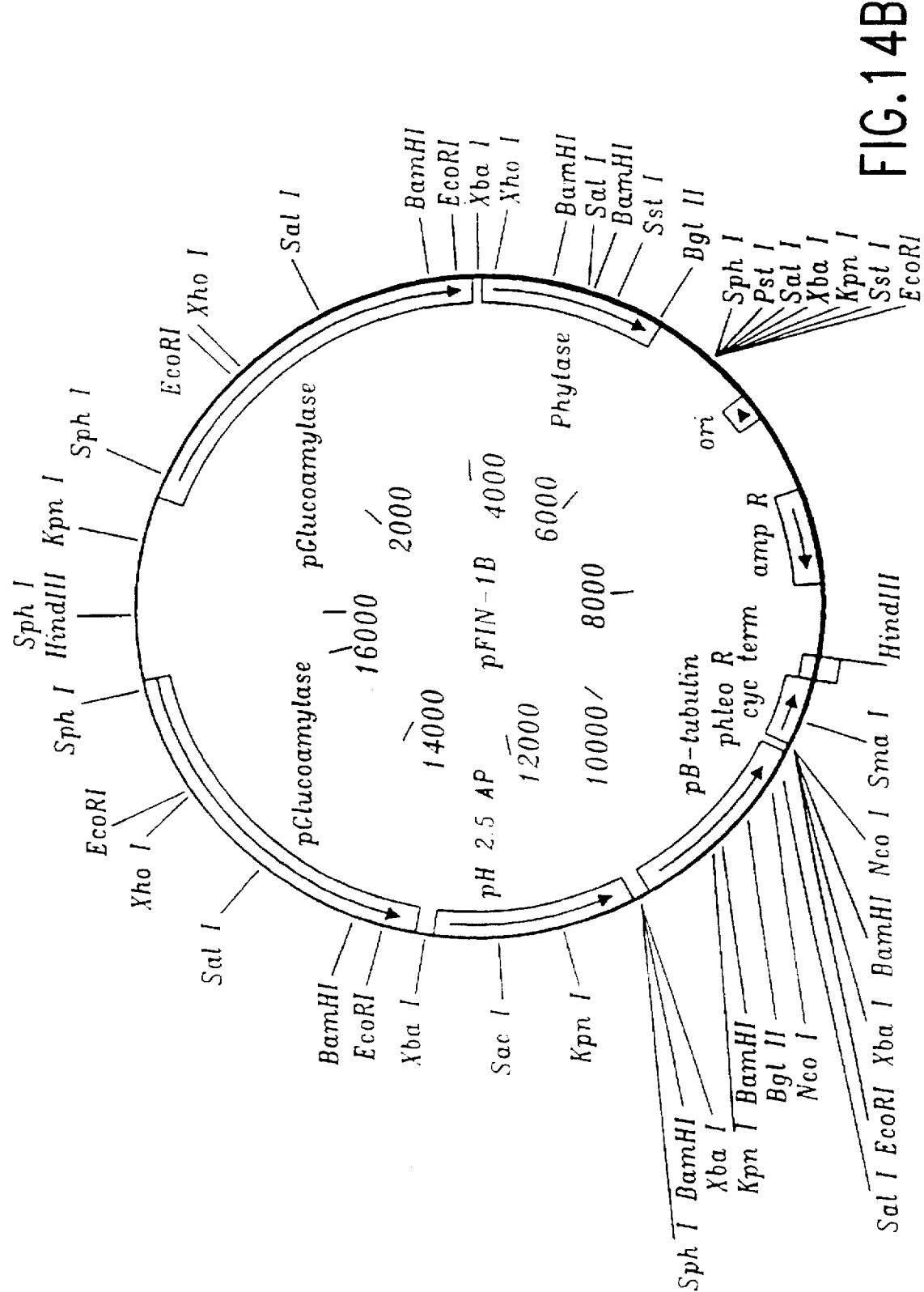

FIG. 14. A dual-enzyme-transformation vector was constructed for over-expression of both phytase and pH2.5 acid phosphatase by a single plasmid. (A) pFIN-1A and (B) pFIN-1B: combination plasmids with both phytase and pH2.5 acid phosphatase under control of separate copies of the GA promoter. An 8.1 kb HindIII fragment was isolated from pPHO-4A and ligated into HindIII-digested pFF-4.

Transformation vector constructs: general considerations:

As is evident from the information in the discussion above of FIGS. 12-15, several different fungal promoter constructions were evaluated: namely, the β-tubulin promoter, theglyceraldehyde 3-phosphate dehydrogenase promoter (GAPDH), and the glucoamylase promoter (GA). The latter two fungal promoters were isolated from *A. niger* ATCC1015 (Tailor, P. et al. 1990). These respective promoters were tested to determine their ability to drive expression of phytase and pH2.5 acid phosphatase.

To facilitate fusion of alternative promoters into the constructs, an XbaI restriction site was introduced by site-directed mutagenesis at the −26 position of the phytase gene. Similarly, an XbaI site was engineered at position −28 of the pH2.5 acid phosphatase gene by PCR mutagenesis (see Materials and Methods, below). The engineered XbaI sites were subsequently used for fusions to alternative fungal promoters previously engineered to contain such XbaI sites in the 5' regulatory regions of the gene.

The results obtained in cells transformed with phytase vector constructs are presented first, below, followed by the results obtained with pH2.5 acid phosphatase.

Transformation of *A. niger* strains ALKO243 and ALKO2268:

*A. niger* var. awamori strain ALKO243 and *A. niger* strain ALKO2268, a mutant strain exhibiting higher production of phytase derived from ALKO243 by UV-mutagenesis, were used as hosts for engineered phytase and pH2.5 acid phosphatase. *A. niger* strains ALKO243 and ALKO2268 were transformed by a modification of the procedure of Tilburn et al. (1983) using phleomycin resistance as a drug-selectable genetic marker. Because the cloned phytase and pH2.5 acid phosphatase genes were maintained on plasmids without a selectable marker, spheroplasts were co-transformed with a phleomycin resistant vector pLO-3 that contains the phleomycin binding protein gene from *Streptoalloteichus hindustanus* coupled to a yeast cytochrome C1 terminator. pLO-3 was derived from the plasmid pUT713 [CAYLA, Toulouse Cedex, France] and is expressed in fungus by the β-tubulin promoter of *A. niger*. Transformants were selected with an equal volume overlay containing 50 μg/ml phleomycin for strain ALKO243 and 195-200 μg/ml for strain ALKO2268. (Strains ALKO243 and ALKO2268 were both sensitive to spheroplast lysis, and required different osmotic buffering conditions; see Materials and Methods, below.) Thirty to forty-five sporulating colonies were obtained per μg of DNA on selection plates. All phleomycin resistant colonies had integrated the phleomycin resistance marker (Southern analysis, data not shown).

Screening of transformants for over-expression of phytase:

Transformants producing higher phytase activity than parental *A. niger* strain ALKO243 were identified in a phytase plate screening assay that colorimetrically measures the accumulation of inorganic phosphate by the reduction of a phosphomolybdate complex (Materials and Methods, below). Transformants with high activity in the plate assay were subsequently tested for phytase production by assaying the enzyme activity released into the broth of a fermentation culture (as described, below).

Figure 15:
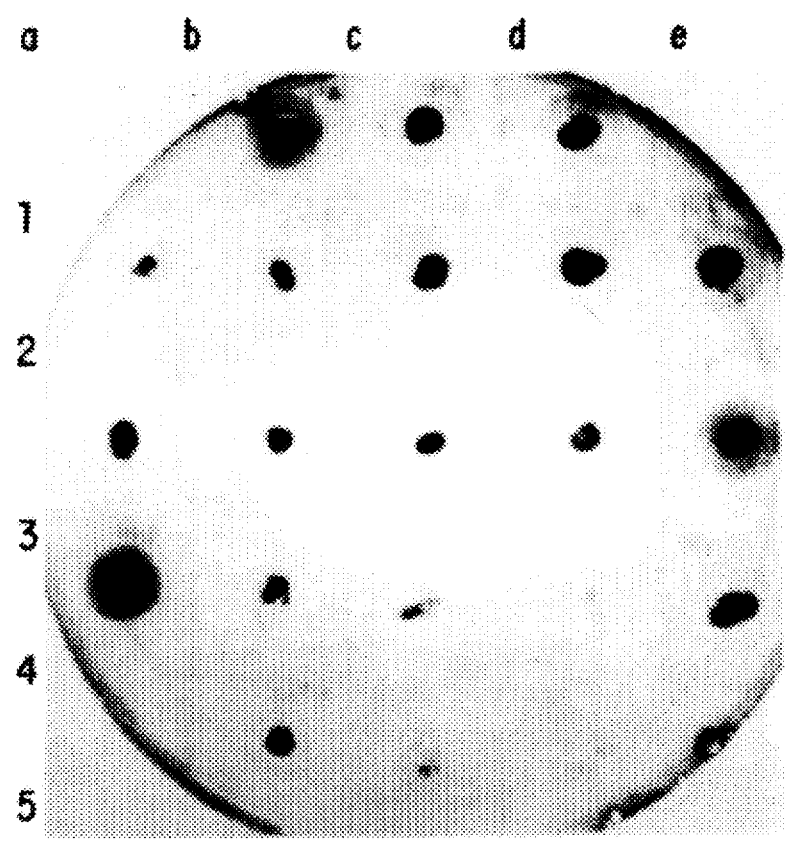
FIG. 15 shows phytase activity in a plate assay of transformed *A. niger* var. awamori subclones that over-produce phytase by up to 1260-fold over the levels produced by the parental ALKO243 strain. (The size of the circles formed by the molybdate indicator complex around clones is proportional to enzyme activity; as described in Example 4, below.

FIG. 15 shows a plate assay for detecting increased phytase activity. Conidia from *A. niger* phytase transformants GAD-10 through GAD-120 was spotted onto plate assay media, incubated for two days at 30° C., and overlaid with Reagent C for color detection (Materials and Methods, below). Positives GAD 130 (a4), GAD 112 (e3) and GAD 118 when grown in shaker flask cultures, exhibited titers of 108,000 PU/ml, 35,600 PU/ml, and 36,700 PU/ml, respectively (i.e., increases of about up to about 1260-fold higher than ALKO243). Phytase activity for untransformed ALKO2268 (b5) was 4,000 PU/ml.

Analysis of phytase over-producing transformants:

The amount of phytase produced by transformants was analyzed by growing the cells in shaker flask cultures and titering the amount of enzyme in the broth, as follows: briefly, cultures were established in shaker flasks under optimal conditions (Materials and Methods, below) and incubated for 5 days, at which time the cells were removed by centrifugation and the supernatant broth from the culture was titrated to determine the amount of phytase activity. (Both the plate assay (above) and the broth titer assay measured the amount of inorganic phosphate released by enzymatic hydrolysis of sodium phytate substrate by colorimetrically quantifying the reduction of a phosphomolybdate complex.)

Using the native phytase promoter (from plasmid; pFF-1 see, Example 2, Materials and Methods, above), of the 58 transformants generated, four exhibited increased production of phytase that was 6.5- to 7.0-fold greater than that produced by non-transformed over-producer strain ALKO2268 ("Untransformed", Table 7, below) or by ALKO2268 control cells that were transformed with a control plasmid pLO-3 which contained no phytase sequences.

TABLE 7

Over-expression of phytase in transformants of production strain ALKO2268[a]

| Strain | Plasmid | Promoter | Activity[b] | Increase[c] |
|---|---|---|---|---|
| ALKO2268 Untransformed | — | Native | 4,000 | — |
| GAD17 | pFF-1 | Native | 26,000 | 6.5 |
| GAD33 | pFF-1 | Native | 17,500 | 4.4 |
| GAD40 | pFF-1 | Native | 10,500 | 2.6 |
| GAD48 | pFF-1 | Native | 28,000 | 7.0 |

[a]Recombinant ALKO2268 over-producers of either phytase in shake flask cultures, i.e., fermentation in a soy flour cultivation media, after 5 days of shaking at 28° C. Cellular and media components were removed by centrifugation. Enzyme activity was determined by adding dilutions of the culture broth supernatant to 1% sodium phytate [Sigma], in 0.2 M citrate buffer, pH 5.0. After fifteen minutes at 37° C., each reaction was terminated by adding 15% TCA (trichloroacetic acid, [Merck]). Released orthophosphate was measured by adding an equal volume of Reagent C (3:1:1 ratio of 1 M sulfuric acid [Mallinckrodt], 2.5% ammonium molybdate [Signma], 10% ascorbic acid [Sigma]) to a 1:10 dilution of the hydrolysis reaction and incubating at 50° C. for twenty minutes. Absorbance of the reaction mixture was measured against a reagent blank and known phosphate standards (1:100–1:400 dilutions of 9.0 mM KH$_2$PO$_4$) at 820 nm;
[b]Activity is expressed as phytase units per ml (i.e., PU/ml);
[c]Increase is expressed as the fold increase in activity (i.e., in PU/ml) over the activity (i.e., in PU/ml) with ALK02268 (i.e., activity of transformant activity of ALK02268).

Further studies involved use of heterologous promoters driving phytase expression. 1467 phytase transformants were examined using the plate assay (157 were derived from strain ALKO243, and 1310 were from strain ALKO2268). Of these, 302 were identified in the plate assay as being potential over-producers of phytase. Of the phytase-over-producing transformants, 25 (i.e., 1.7% of the 1467 evaluated) had enzyme activity in excess of 700-fold greater PU/ml than that produced by ALKO243. (The results obtained with 18 of the 25 transformants are shown in Table 8.) The transformant exhibiting the highest phytase production (i.e.,GAI-6; 181,000 PU; about 2,100-fold greater PU/ml than ALKO243) was the result of transformation with the pFF-9 construct containing a glucoamylase (GA) fungal promoter. The latter transformant showed significantly increased levels of phytase production compared to ALKO2268 (an over-producer) or to ALKO243 (a wild-type strain) (see Table 8, below).

TABLE 8

A. niger phytase transformants which produced phytase enzyme over 700-fold greater than ALKO243 in shake flask cultures*

| Transformant | Strain | Plasmid[a] | Promoter | Activity[b] | Increase[c] |
|---|---|---|---|---|---|
| GAI-6 | A.2268 | PFF-4 | GA | 181,000 | 2129 |
| GAL-142 | A.2268 | pFF-3 | GAPDH | 174,000 | 2047 |
| GAN-1 | A.2268 | pFF-3 | GAPDH | 170,000 | 2000 |
| GAG-12 | ALK0243 | pFF-3 | GAPDH | 166,000 | 1953 |
| GAO-248 | A.2268 | pFF-9 | GA | 164,000 | 1929 |
| GM42 | A.2268 | PFF-4 | GA | 145,000 | 1706 |
| GAK446 | A.2268 | pFF-4 | GA | 132,000 | 1553 |
| GM-2 | A.2268 | pFF-4 | GA | 131,000 | 1541 |
| GAK4-52 | A.2268 | pFF-4 | GA | 131,000 | 1541 |
| GAM-111 | A.2268 | pFF-6A | NATIVE | 129,000 | 1518 |
| GAK447 | A.2268 | pFF-4 | GA | 121,000 | 1424 |
| GAM-225 | A.2268 | pFF-9 | GA | 112,000 | 1318 |
| GAD-103 | A.2268 | pFF-3 | GAPDH | 108,000 | 1271 |
| GAD-23 | A.2268 | pFF-3 | GAPDH | 108,000 | 1271 |
| GAM-199 | A.2268 | pFF-9 | GA | 107,600 | 1266 |
| GAE-32 | A.2268 | pFF-6A | NATIVE | 72,600 | 854 |
| GAL-65 | A.2268 | pFF-9 | GA | 72,200 | 849 |
| GAE-3 | A.2268 | pFF-6A | NATIVE | 67,500 | 794 |
| Control | ALK02268 | None | Native | 3,800 | 45 |
| Control | ALK0243 | None | Native | 85 | 1 |

[a]Plasmids pFF-9, pFF-8 and pFF-6A were used in linear form with all E. coli sequences excised.
Transformant designation;
GA = glucoamylase promoter;
GAPDH = glyceraldehyde 3-phosphate dehydrogenase promoter;
NATIVE = native phytase promoter;
[b]= Activity from shake flask fermentation culture; Enzyme activities (i.e., in PU/ml) are averages of two independent fermentations;
[c]Increase is expressed as the fold increase in activity in shake flask culture over the activity with ALKO243 in shake flask culture (i.e., activity in PU/ml of transformant per activity in PU/ml of ALK0243).

Figure 16A:
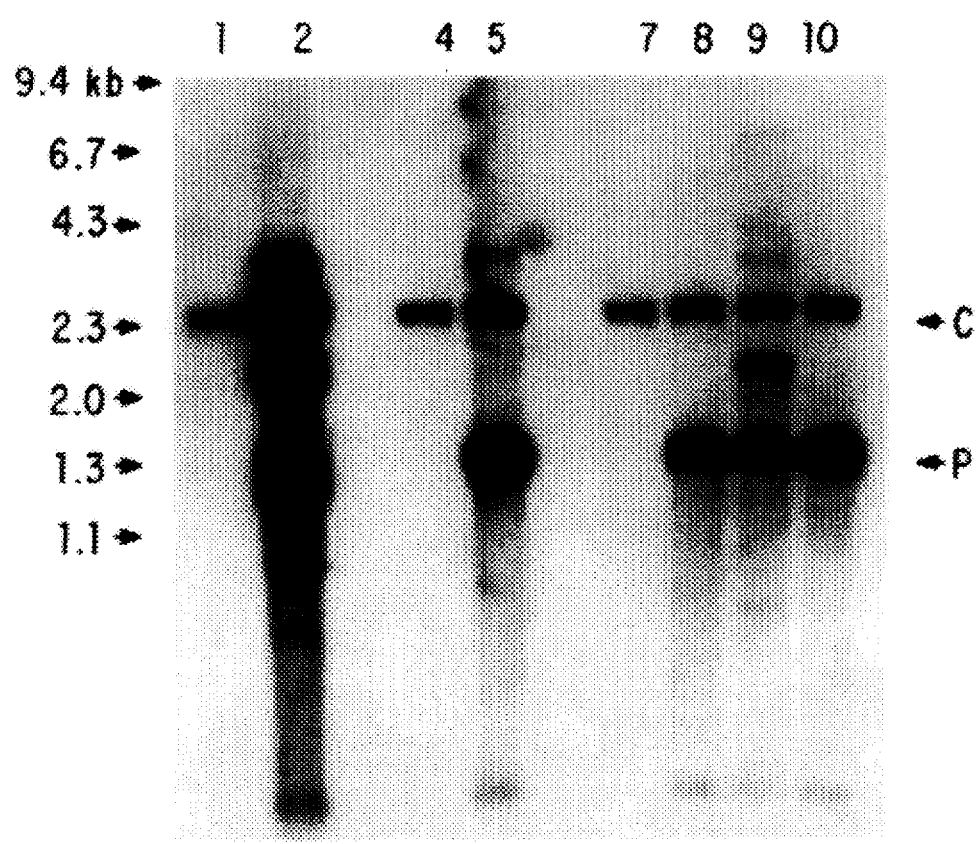
FIG. 16A shows Southern blot analysis of untransformed control ALKO2268 (lanes 1, 4 and 7) and over-producing phytase transformants (lanes 2, 5, 8, 9 and 10)

Molecular characterization: phytase transformants:

Southern and Northern analyses were conducted with DNA and MRNA (respectively), isolated from phytase transformants GAE 32, GAK 4–47, GAL 65, GAM 225 and GAO 248 (Table 8) that over-produced phytase in shake flask fermentation cultures. Genomic DNA was isolated from the respective transformant strains, digested with restriction enzymes, and probed with a radiolabelled cloned phytase DNA restriction fragment (i.e., isolated from pFF1, above), to determine the gene copy number and the method of integration in the transformants. An increase in gene copy number was determined by comparing the density of the blot at 1.3 kb (i.e., the transformation vector construct DNA) against the density of the endogenous chromosomal copy of the phytase gene (i.e., at 2.4 kb) and against control ALKO2268 genomic DNA. Quantification was achieved by scanning densitometry (FIG. 16A). Three to five additional phytase vector gene copies, arranged in multiple different patterns of integration (data not shown), were detected in transformants GAE 32, GAK 4–47, GAL-65, GAM-225 and GAO-248.

Figure 16B:
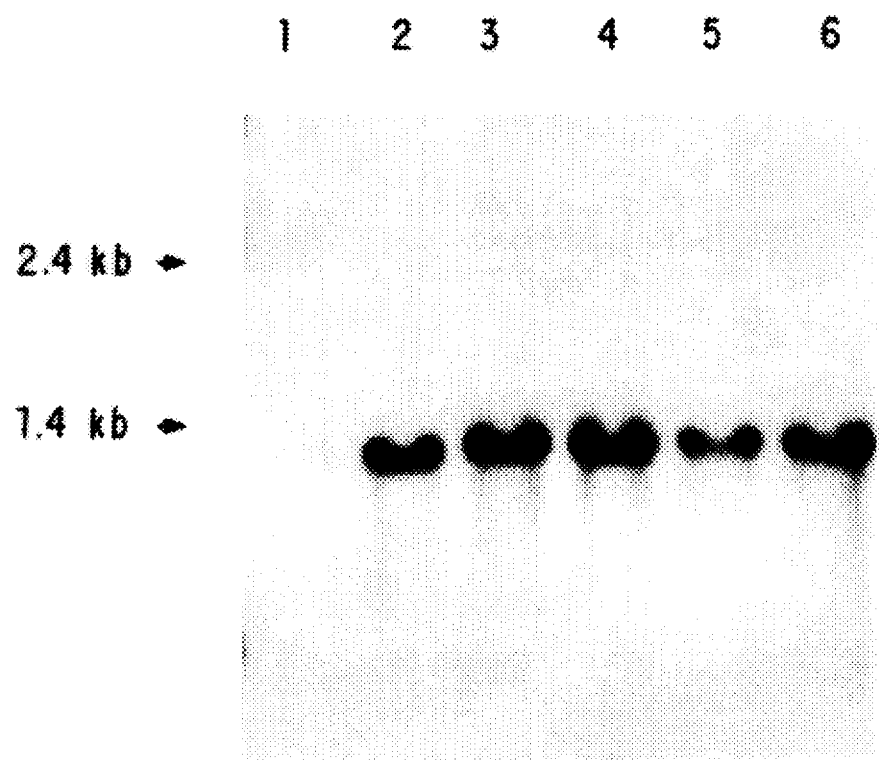
FIG. 16B shows Northern blot analysis of mRNA levels in untransformed Control ALKO2268 (lane 1) and transformed strains (lanes 2–6)

Expression of phytase mRNA levels by Northern blotting demonstrated that message levels of transformants were consistently increased by seven- to thirteen-fold over non-transformed controls (FIG. 16B). However, actual levels may be higher because it proved difficult to isolate mRNA from cells grown in production media, and it was therefore necessary to make these comparisons under sub-optimal conditions for cell growth and phytase expression.

FIG. 16A. Southern blot analysis of phytase genomic copy number in over-producing phytase transformants:

genomic DNA was digested with BamHI, blotted, electrophoresed, and the filter was probed with BamHI fragments of the 5' region of pFF-1. Gene copy number was determined by comparing blot density of gene copies (at 1.3 kb) in transformants with the blot density of the endogenous phytase gene (at 2.4 kb) by scanning densitometry. Lanes 1, 4, 7: Untransformed control ALKO2268. Lanes 2, 5, 8, 9, 10: over-producing phytase transformants GAE-32, GAK-47, GAL-65, GAM-225, GAO-248, respectively.

FIG. 16B. Northern blot analysis messenger RNA levels in phytase over-producing transfornants: 20 μg of each total RNA sample was electrophoresed in a formaldehyde gel and transferred to nitrocellulose. Each transformant was probed with the restriction fragments of the phytase gene (i.e., BamHI fragments from pFF-1.). Increased phytase message level was measured by scanning densitometry of the mRNA. RNA from ALKO2268 (Lane 1) was used as baseline control. Lanes 2–6: GAE-32, GAK-47, GAL-65, GAM-225, GAO-248, respectively.

The results presented in Table 9, below, summarize the quantitative results obtained by scanning the density of the Southern and Northern blots in FIG. 16A and FIG. 16B.

TABLE 9

Comparison of phytase gene copy number mRNA levels and enzyme production by phytase over-producers

| Strain | plasmid[a] | Copy No. | mRNA[b] | Activity[c] | Increase[d] |
|---|---|---|---|---|---|
| ALKO243 | None | 1.0 | — | 85 | 1 |
| ALKO2268 | None | 1.0 | 1.0 | 3,800 | 45 |
| GAO-248 | pFF9 (GA, lin) | 6.0 | 9.2 | 164,000 | 1,929 |
| GAK47 | pFF4 (GA, cir) | 3.0 | 13.2 | 121,400 | 1,428 |
| GAM-225 | pFF9 (GA, lin) | 3.0 | 7.6 | 112,000 | 1,318 |
| GAE-32 | pFF6 (nat, cir) | 6.0 | 11.3 | 72,600 | 854 |
| GAL-65 | pFF9 (GA, lin) | 3.0 | 11.8 | 72,200 | 849 |

[a]nat = native promoter;
cir = circular vector;
lin = linear DNA fragment;
GA = glucoamylase promoter;
[b]mRNA = messenger RNA amplification levels (as fold-increase over levels in ALKO243);
[c]Activity = phytase production in fermentation culture represented in phytase units per ml (i.e., PU/ml), conditions described in Table 7, above;
[d]= Increase is expressed as the fold increase in activity in shake flask culture over the activity with ALKO243 in shake flask culture (i.e., activity in PU/ml of transformant per activity in PU/ml of ALKO243).

Analysis of over-producing pH2.5 acid phosphatase transformants:

It was not possible to develop a plate screening assay specific for pH2.5 acid phosphatase; therefore, transformants were analyzed by evaluating enzyme production in the culture broth after 5 days of fermentation in shake flasks (as described above, Table 7, and in the Materials and Methods, below). The conditions for measuring production of pH2.5 acid phosphatase in the fermentation shake-flask assay are described below (Table 10) using paranitrophenylphosphate as the substrate (also described below in the Materials and Methods). As in Table 7, above, the levels of enzyme in the culture broth supernatant were titered and the levels of enzyme were compared with the levels produced over the same 5-day period of incubation by a control culture of the ALKO243 strain of A. niger.

Of the 55 transformants generated with the plasmid pAP-3 containing the native promoter driving expression of pH2.5 acid phosphatase (Example 2, Materials and Methods, above), four transformants showed increases in production of pH2.5 acid phosphatase that was 25- to 57-fold greater (Table 10) than the levels produced by parental strain ALKO243. The highest producing transformant (GAQ56) exhibited nearly a 58-fold increase over untransformed ALKO2268 (Table 10), and up to a 126-fold increase is illustrated in Table 11, below.

TABLE 10

Over-expression of pH 2.5 acid phosphatase in transformants of production strain ALKO2268[a]

| Strain | Plasmid | Promoter | Activity[b] | Increase[c] |
|---|---|---|---|---|
| Untransformed: | | | | |
| A.2268 | None | Native | 2,300 | — |
| Transformed: | | | | |
| GAQ56 | pAP-3 | Native | 133,000 | 57.5 |
| GAO13 | pAP-3 | Native | 102,500 | 44.5 |
| GAQ66 | pAP-3 | Native | 77,800 | 33.8 |
| GAO62 | pAP-3 | Native | 57,600 | 25.0 |

[a]Conditions, as described in Table 7, above;
[b]Activity in acid phosphatase units per ml (i.e., HFU/ml);
[c]Increase is expressed as the fold increase in activity in shake flask culture over the activity with ALKO2268 in shake flask culture (i.e., activity in HFU/ml of transformant per activity in HFU/ml of ALKO2268).

Further studies evaluated heterologous promoters driving pH2.5 acid phosphatase expression. 1181 transformants over-produced pH2.5 acid phosphatase (410 resulted from strain ALKO243 and 771 were from strain ALKO2268). 32 transformants (2.7%) were identified that produced pH2.5 acid phosphatase in excess of 30 HFU/ml. The highest producing transformant (i.e., GAO-69) averaged 126 HFU/ml. This expression resulted from transformation with a plasmid construct having a fungal glucoamylase (GA) promoter (Table 11).

TABLE 11

A. niger pH 2.5 acid phosphatase transformants over-producing enzyme at levels over 40-fold higher than ALKO243 in shake flask fermentation cultures[a]

| Transformant | Strain | Plasmid | Promoter | Activity[b] | Increase[c] |
|---|---|---|---|---|---|
| GAO-69 | A.2268 | pPREPHO-4 | GA | 693,000 | 126 |
| GAW-131 | A.2268 | pPHO-4A | GA | 583,000 | 106 |
| GBL-128 | ALKO243 | pPHO-3 | GAPDH | 566,500* | 103* |
| GBL-97 | ALKO243 | pPHO-3 | GAPDH | 533,500* | 97* |
| GAO-61 | A.2268 | pPREPHO-4 | GA | 451,000 | 82 |

TABLE 11-continued

A. niger pH 2.5 acid phosphatase transformants over-producing enzyme at levels over 40-fold higher than ALKO243 in shake flask fermentation cultures[a]

| Transformant | Strain | Plasmid | Promoter | Activity[b] | Increase[c] |
|---|---|---|---|---|---|
| GAW-89 | A.2268 | pPHO-3 | GAPDH | 412,500 | 75 |
| GAW-130 | A.2268 | pPHO-4A | GA | 385,000 | 70 |
| GAW-121 | A.2268 | pPHO-4A | GA | 379,500 | 69 |
| GBL-87 | ALKO243 | pPHO-3 | GAPDH | 346,500* | 63* |
| GBL-119 | ALKO243 | pPHO-3 | GAPDH | 335,500* | 61* |
| GAO-84 | A.2268 | pPREPHO-4 | GA | 330,000 | 60 |
| GAW-54 | A.2268 | pPHO-3 | GAPDH | 280,500 | 51 |
| GBL-129 | ALKO243 | pPHO-3 | GAPDH | 264,000* | 45* |
| GAW-141 | A.2268 | pPHO-4A | GA | 258,500 | 47 |
| GBL-103 | ALKO243 | pPHO-3 | GAPDH | 242,000* | 44* |
| GAW-112 | A.2268 | pPHO-4A | GA | 236,500 | 43 |
| GBL-92 | ALKO243 | pPHO-3 | GAPDH | 236,500* | 43* |
| GAW-114 | A.2268 | pPHO-4A | GA | 231,000 | 42 |
| GAT-143 | ALKO243 | pPHO-4A | GA | 231,000 | 42 |
| Control | ALKO2268 | None | native | 2,300 | 0.5 |
| Control | ALKO243 | None | native | 5,500 | 1 |

[a]Transformed ALKO2268 and ALKO243 over-producers of pH 2.5 acid phosphatase in shake flask fermentation cultures (conducted as described in Table 7, above). Enzyme activity was determined by adding dilutions of the culture broth supernatant to 30 mM p-nitrophenyl phosphate (Boehringer Mannheim) in 0.2 M glycine-HCL, pH 2.5 buffer. The reaction was terminated and orthophosphate assayed as described in the footnote to Table 7. Enzyme activities are averages of activities from two independent fermentations except (*), which were from single fermentations. Plasmids pPHO-3 and pPHO-4A were used in linear forin with E. coli sequences excised.
Transformant designation:
GA = glucoamylase promoter;
GAPDH = glyceraldehyde 3-phosphate dehydrogenase promoter;
[b]Activity in acid phosphatase units per ml (i.e., HFU/ml);
[c]Increase is expressed as the fold increase in activity in shake flask culture over the activity with ALKO243 in shake flask culture (i.e., activity in HFU/ml of transformant per activity in HFU/ml of ALKO243).

Molecular characterization of pH2.5 acid phosphatase transformants:

Copy number and message levels were determined using Southern and Northern blot analysis and scanning densitometry (as described above) for five of the highest pH2.5 acid phosphatase over-producers identified in the shake flask fermentation cultures (Table 11, above). DNA from pH2.5 acid phosphatase transformants GAT-143, GAW-54, GAW-89, GAW-121 and GAW-130 was digested with restriction enzymes and hybridized to a radiolabelled pH2.5 acid phosphatase-specific probe. Overall, the pH2.5 acid phosphatase transformants had higher gene copy numbers (Table 12, below) than observed above with the phytase transformants (Table 9, above). In contrast, message levels for pH2.5 acid phosphatase transformants (Table 12) were not as high as observed in phytase transformants (Table 9). However, as with phytase transformants above, the pH2.5 acid phosphatase message levels were not measured under optimal fermentation conditions because of the difficulty encountered in isolating RNA from cells under production culture conditions. Therefore, expression under production conditions may be higher than that measured here.

TABLE 12

Comparison of pH 2.5 Acid Phosphatase Gene Copy Number with mRNA levels and Enzyme Production by Recombinant Transformed Strains[a]

| Strain | Plasmid | Copy No. | pH 2.5 Acid Phosphatase mRNA | Activity[b] | Increase[c] |
|---|---|---|---|---|---|
| A.2268 | None | 0 | 1.0 | 2,300 | 0.4 |
| GAT-143 | pPHO4A (GA, lin) | 10.0 | 5.6 | 231,000 | 42.0 |
| GAW-54 | pPHO3 (GAP, lin) | 7.0 | 5.7 | 280,500 | 51.0 |
| GAW-89 | pPHO3 (GAP, lin) | 12.0 | 3.0 | 412,500 | 75.0 |
| GAW-121 | pPHO4A (GA, lin) | 11.0 | 3.0 | 379,500 | 69.0 |
| GAW-130 | pPHO4A (GA, iin) | 7.0 | 7.2 | 385,000 | 70.0 |

[a]GA = glucoamylase promoter;
GAP = glyceraldehyde 3-phosphate dehydrogenase promoter;
lin = linear DNA fragment;
mRNA = messenger RNA amplification levels (as fold-increase over levels in ALKO243);
[b] = pH 2.5 acid phosphatase activity represented in acid phosphatase units per ml (HFU/ml); comparisons made with cells grown in shake flask cultures; Activity = enzyme activity measured as described in Table 10, above;
[c]Increase is expressed as the fold increase in activity in shake flask culture over the activity with ALKO243 in shake flask culture (i.e., activity in HFU/ml of transformant per activity in HFU/ml of ALKO243).

Materials and Methods:

Plasmid constructions were designed so that vector backbone sequences could be easily removed prior to transformation of the respective genes into fungi. Linear DNA was isolated from agarose and purified by GeneClean to remove any possible contaminating specificities. Constructs A–D and Constructs E–H expressing the phytase and pH2.5 phosphatase genes, respectively, under different regulatory control were prepared as described below.

Phytase and pH2.5 acid phosphatase expression plasmids:
Construct A: pFF-6 phytase under control of its native promoter.

The 2.6kb SphI fragment containing the phytase gene was cloned into the SphI site of pLO-3. Two orientations were generated, termed pFF-6A and pFF-6B. Linear DNA was isolated from either vector as a 4.9 kb HindIII fragment.

Construct B: pFF-8 Phytase under control of the *A. niger* GAPDH promoter.

Fungal expression vector pPRE8-1 was cut with BglII and blunted with DNA polymerase I Klenow fragment; the plasmid was then cut with PstI to completion. The phleomycin resistance (Phleo$^r$) marker expression cassette was removed from pLO-3 (as a HindIII (filled)/PstI fragment), and ligated to the cut pPRE8-1 to give pPRE8-2. Transformants were identified by restriction analysis. The 2.0 kb XbaI fragment containing the phytase gene (Example 2, Materials and Methods) was ligated into a unique XbaI site downstream from the GAPDH promoter in plasmid pPRE8-2. Correctly oriented transformants containing pFF-8 were identified by restriction analysis. Linear DNA was isolated from pFF-8 as a 6.7 kb PstI fragment.

Construct C: pFF-9 Phytase under control of the *A. niger* GA promoter.

The 2.0 kb XbaI fragment containing the phytase gene (Example 2, Materials and Methods, above) was ligated to the unique XbaI site of fungal expression vector pGA to give pFF-4. Transformants containing correctly oriented plasmid were identified by restriction analysis. pFF-4 was cut partially with KpnI to produce singularly cut linear plasmid. The ends were blunted with T4 DNA Polymerase. The plasmid was then cut to completion with HindIII. pLO-3 was first cut with KpnI and blunted with T4 DNA Polymerase, and then cut with HindIII. The 2.1 kb fragment containing the phleo$^r$ expression cassette was purified from agarose with GeneClean and ligated to cut pFF-4. Transformants containing pFF-9 were identified by restriction analysis. Linear DNA was isolated from pFF-9 as an 7.3 kb HindIII/KpnI fragment.

Construct D: pFF-11 Phytase under control of the *A. niger* GA promoter with secretion via the GA signal sequence.

Oligonucleotides 260 and 261 were synthesized coding for an XbaI site upstream from the translation initiation region and signal sequence for glucoamylase, which was located, in turn, upstream from nucleotide sequence encoding the N-terminus of phytase (SEQ. ID. NO. 1). (The construct also contained a native XhoI site immediately downstream from this region.) The two synthetic oligonucleotides used in this construct had the following nucleotide sequence: namely, a phleo$^r$ cassette was added as a HindIII fragment into a unique HindIII site of the construction. Transformants containing correctly oriented plasmid were identified by restriction analysis. Linear DNA was isolated from pFF-11 as a 7.35 KpnI fragment. Construct E: pPHO-1 pH2.5 Acid Phosphatase (AP) under control of its native promoter.

pAP-3 was cut with EcoRI and blunt-ended with Klenow. The phleo$^r$ cassette was removed from pLO-3 as a HindIII fragment, blunt-ended with Klenow, and ligated into the cut pAP-3 plasmid. Transformants containing correctly oriented pPHO-1 were identified by restriction analysis. Linear DNA was isolated from pPHO-1 as a 6.3 kb PstI fragment.

Construct F: pPHO-2, pH2.5 Acid Phosphatase gene under control of the *A. niger* b-tubulin promoter.

Fungal expression vector pTL113 was cut with XbaI and dephosphorylated with calf intestinal phosphatase. A 2.0 kb XbaI fragment containing the pH2.5 phosphatase gene (Example 2, Materials and Methods, above) was ligated into cut pTl113 to give pPREPHO-2. Transformants containing correctly oriented plasmids were identified by restriction analysis. pPREPHO-2 was partially cut with SphI to give singularly cut linear plasmid. The ends of cut pPREPHO-2 were blunted with T4 DNA Polymerase. A 2.7 kb blunt-ended HindIII fragment containing the phleo$^r$ expression cassette from pLO-3 was ligated into the cut pPREPHO-2 vector. Transformants containing correctly oriented pPHO-2 plasmid were identified by restriction analysis. Linear DNA was isolated as a 6.0 kb PstI fragment.

Construct G: pPHO-3, pH2.5 acid phosphatase gene under control of the *A. niger* GAPDH promoter.

A 4.3 kb XbaI fragment containing the pH2.5 phosphatase gene (Example 2, above) and the phleo$^r$ expression cassette was removed from pPho-2 by partial digestion. The fragment was purified from agarose with GeneClean and ligated into a unique XbaI site in fungal expression vector pPRE8-1. Transformants containing correctly oriented pPHO-3 plasmid were identified by restriction analysis. Linear DNA was isolated as a 7.0 kb PstI fragment.

Construct H: pPHO-4, pH2.5 Acid Phosphatase gene under control of the *A. niger* GA promoter.

The 2.0 kb XbaI fragment containing the pH2.5 acid phosphatase gene (Example 2, above) was ligated into XbaI cut fungal expression vector pGA to give pPPEPHO-4. Transformants containing correctly oriented plasmid were identified by restriction analysis. A 5.5 kb Kpnl fragment containing the GA promoter and the pH2.5 Acid phosphatase gene was removed from pPREPHO-4 by partial digestion. The resulting fragment was purified from agarose with GeneClean and blunt-ended with T4 DNA Polymerase. The blunt-ended fragment was ligated into pLO-3 cut with PstI, and then the DNA was blunt-ended to give plasmids in two different orientations, termed pPHO-4A and pPHO-4B. Transformants containing each orientation were identified by restriction analysis. Linear DNA was isolated as an 8.1 kb HindIII fragment.

Oligo260:  5'- CTAGACACCTCAGCAATGTCGTTCCGATCTCTACTCGCCCTGA
GCGGCCTCGTCTGCACAGGGTTGGCACTGGCAGTCCCCGCC-3'  (84 mer) (SEQ. ID. NO. 93); and, Oligo261:  5'- TCGAGGCGGGGACTGCCAGTGCCAACCCTGTGCAGACGAGGC
CGCTCAGGGCGAGTAGAGATCGGAACGACATTGCTGAGGTGT-3'  (84 mer) (SEQ. ID. NO. 94)

Oligonucleotides 260 and 261 were annealed and then ligated to XbaI/XhoI cut pFF-1 to give pFF-1GA. The glucoamylase promoter from pGA was ligated into pFF-1GA (as a KpnI/XbaI fragment) to give pPREFF-11. Finally, DNA transformation of *A. niger* strains ALKO243 and ALKO2268:

Spheroplasts were obtained by first adding 0.5 ml to 1 ml of a fungal spore suspension from conidiating cultures grown on PD slants to 50 ml of CM media in 250-ml flasks. For ALKO243, cultures were grown overnight at 35° C., 200 RPM, before filtration. ALKO2268 cultures were grown 48 hours at 30° C., 200 RPM. The resulting mycelia were collected onto a double layer of cheesecloth, added to 50 ml of KCM buffer (0.7M KCl, 10 mM MOPS, pH5.8) with 5 mg/ml Novozym 234 (Novo BioLabs) and incubated at 30° C., 85 RPM overnight for spheroplast generation.

The spheroplasts were harvested by filtration through a funnel packed with mira cloth and covered with cheesecloth into four 15 ml conical centrifuge tubes, then spun for ten minutes, 1500 RPM in a bench top centrifuge. The pellets were gently resuspended in a total of 15 ml Sorbitol Buffer (1M Sorbitol, 50 mM $CaCl_2$) and re-centrifuged. The pellet was again washed in Sorbitol Buffer (SB) then resuspended in SB to a density of $5\times10^7$/ml.

5 μg of linear or plasmid DNA in 20 μl TE was added to 200 μl of spheroplasts. For co-transformations 1 μg of selectable phleomycin resistance marker gene DNA, pLO3, was also added. 50 μl of PCM (40% PEG 8000, 10 mM MOPS, pH5.8, 50 mM $CaCl_2$ [$CaCl_2$ added just before use]) was gently pipetted into the DNA-spheroplast mixture and incubated on ice for 30 minutes.

1 ml of PCM was added to the transformation mix, the mix was pipetted into 50 ml of Regeneration Agar (MA: CM plus 1.3M mannitol, 3% agar) and divided into five petri dishes. Spheroplasts were allowed to regenerate 3 to 5 hours at 35° C. before overlaying with an equal amount of OL+phleomycin (OL: 1% peptone, 1% agar; phleomycin [CAYLA]: 50 μg/ml for ALKO243, 195 μg/ml for ALKO2268). Putative transformants were transferred to PD+phleomycin slants and grown at 28° C.

Phytase plate assay:

Transformants producing higher phytase yields were identified by a plate assay that colorimetrically measures the accumulation of inorganic phosphate by the reduction of a phosphomolybdate complex. Conidia from putative transformants was spotted onto assay plates and incubated two days at 30° C. 20 ml of Reagent C (3:1:1 ratio of 1M sulfuric acid [Mallinckrodt], 2.5% ammonium molybdate [Sigma], 10% ascorbic acid [Sigma] was applied to the top of the media, and the plates were incubated at 50° C. for fifteen minutes before scoring for color intensity. (Plate assay agar: 2% corn starch [Sigma #S-4126], 1% protease peptone [Difco #0122-1], 30 g glucose/l, 5 g $NH_4NO_3$/l, 0.5 g $MgSO_4\cdot7H_2O$/l, 0.5 g KCl, 0.183 g $FeSO_4\cdot7H_2O$l, 3% agar, 3% sodium phytate [Sigma #P-3168].)

Phytase and pH2.5 acid phosphatase enzyme assays:

Enzyme assays were conducted as described in Example 1, above.

Production of phytase and pH2.5 acid phosphatase by transformed recombinant cells:

Transformed recombinant filamentous fungi expressing phytase and pH2.5 acid phosphatase were cultivated under identical conditions in a soy-based production medium [(50 g/l soy flour, 30 g/l glucose, 5 g/l, $NH_4NO_3$, 0.5 g/l $MgSO_4\cdot7H_2O$, 0.5 g/lKCl, 0.183 g/l$FeSO_4\cdot7H_2O$, pH5.0 )] for five days on a rotary shaker at 200 RPM and 28° C. Transformants utilizing the glucoamylase promoter were additionally grown in soy glucoamylase media (soy media plus 4% corn starch and 6% glucose. Enzyme samples were collected by centrifuging an aliquot of the fermentation culture at 13,000 RPM in a microcentrifuge for ten minutes, then transferring the enzyme-containing supernatant to a fresh tube for enzyme assay (below).

EXAMPLE 5

Balanced Over-expression Of Both The Phytase Gene And The pH2.5 Acid Phosphatase Gene Analysis of dual-enzyme-transformants with both phytase and pH2.5 AP genes:

Because both pH2.5 acid phosphatase and phytase are required for optimal degradation of phytic acid, it was considered highly advantageous to construct strains that might over-produce both enzymes. Since phytic acid was dephosphorylated most efficiently when ratios of phytase units to acid phosphatase units are tailor-made for the specific use (Example 1, above), it was considered even more desirable if transformant strains could be selected that would over-produce both enzymes in this desired range of ratio.

A. niger ALKO243 transformants were selected using the combinations of transformation vector plasmids shown in Table 13 and co-transfection with a phleomycin selectable marker (as described above, Example 4, Materials and Methods). Following co-transformation with the indicated combinations of phytase and pH2.5 acid phosphatase containing plasmids (Table 13), the transformants were grown in shaker flask cultures (as described in Table 7 and Table 10, Example 4, above) to evaluate enzyme production.

All dual-enzyme transformants were first assayed to determine the amount of pH2.5 acid phosphatase; if levels were significantly elevated, then phytase activity was assayed.(Since phytase has two pH optimums at pH2.5 and pH5.0 [above, Example 1], its activity can be detected under pH2.5 acid phosphatase parameters.) (The acid phosphatase values were adjusted to account for the percentage of phytase activity that appears in the pH2.5 acid phosphatase assay.) Nine of 425 transformants were found to over-produce both phytase and pH2.5 acid phosphatase; and, at greater than 4:1 HFU/PU (i.e., pH2.5 acid phosphatase HFU divided by phytase PU).

TABLE 13

DNA Constructs Used to Construct Dual-Enzyme-Transformants of ALKO243 with Elevated Levels of both pH 2.5 Acid Phosphatase and Phytase

| Plasmid DNA Combination | Number Analyzed |
|---|---|
| pPHO1/PFF4 | 3 |
| pPHO3/pFFl | 108 |
| pPHO3/pFF2 | 50 |
| pPHO3/pFF4 | 11 |
| pPHO3(lin)/pFF6(lin) | 74 |
| pPHO3(lin)/pFF8(lin) | 7 |
| pPHO4A/pFF1 | 21 |
| pPHO4A/pFF2 | 22 |
| pPHO4A/pFF3 | 25 |
| pPHO4A/pFF4 | 22 |
| pFF6/prepho2 | 2 |
| pFIN-1A | 84 |
| pFIN-1B | 46 |
| Total | 475 |

Eighteen of the 475 combination transformants (Table 13) demonstrated activities in excess of 20-fold HFU/ml greater than ALKO243 for pH2.5 acid phosphatase and 250-fold PU/ml greater than ALKO243 for phytase activity (Table 14).

TABLE 14

A. niger ALK0243 Dual-Enzyme-Transformants Expressing Both Phytase and pH 2.5 Acid Phosphatase (pH 2.5AP) at Levels of Enzyme Activity Greater than the ALK0243 parent cell by greater than 20-fold for pH 2.5 Acid Phosphatase (A.P.) and greater than 250-fold for Phytase (Phy.)[a]

| Transformant | Plasmid(s)/Promoter AP/Phy | Activity HFU/ml | Activity PU/ml | Ratio HFU/PU | Increase A.P. | Increase Phytase |
|---|---|---|---|---|---|---|
| GAX-11 | pPHO-4A/pFF-4(GA/GA) | 280,500 | 53,000 | 5.3 | 51 | 624 |
| GAX-12 | pPH0-4A/pFF-4(GA/GA) | 176,000 | 29,000 | 6.1 | 32 | 342 |
| GBE-14 | pPH0-3/pFF-4 (GAPDH/GA) | 147,300 | 29,400 | 5.0 | 27 | 346 |
| GBH-134 | pPH0-3/pFF-2 (GAPDH/β-T) | 291,500 | 39,000 | 7.5 | 53 | 459 |
| GBH-157 | pPH0-3/pFF-2 (GAPDH/β-T) | 247,500 | 54,000 | 4.6 | 45 | 635 |
| GBJ-9 | pFIN-JA (GA/GA) | 212,400 | 38,800 | 5.5 | 39* | 456 |
| GBJ-10 | pFIN-IA (GA/GA) | 241,000 | 38,100 | 5.6 | 44* | 445 |
| GBJ-13 | pFIN-JA (GA/GA) | 259,800 | 25,300 | 10.2 | 47* | 299 |
| GBJ-16 | pFIN-JA (GA/GA) | 280,600 | 23,200 | 12.1 | 51* | 273 |
| GBJ-26 | pFIN-JB (GA/GA) | 328,100 | 45,700 | 7.2 | 60* | 538 |
| GBJ-27 | pFIN-JB (GA/GA) | 218,100 | 39,700 | 5.5 | 40* | 467 |
| GBJ-28 | pFIN-1B(GA/GA) | 372,300 | 23,600 | 15.8 | 68* | 278 |
| GBJ-31 | pFIN-IB(GA/GA) | 299,000 | 30,400 | 9.8 | 54* | 355 |
| GBJ-35 | pFIN-IB(GA/GA) | 255,300 | 28,400 | 9.0 | 46* | 334 |
| GBJ-35 | pFIN-JB (GA/GA) | 277,500 | 25,600 | 10.8 | 50* | 301 |
| GBJ-40 | pFIN-4A (GA/GA) | 401,000 | 38,200 | 10.5 | 73 | 449 |
| GBJ-76 | pPH0-4A/PFF-2 (GA/β-T) | 201,600 | 46,100 | 4.4 | 37* | 542 |
| GBJ-82 | pPH0-4A/pFF-2 (GA/β-T) | 309,800 | 40,100 | 7.7 | 56* | 472 |
| ALK0243 | control/native (native) | 5,500 | 85 | 64.7 | 1 | 1 |

[a]Enzyme activities were determined in shake flask cultures (as described in Table 10, Example 4, above). The results are expressed as the average of at least two independent fermentation cultures except (*) which was taken from a single fermentation culture. pH 2.5 acid phosphatase (pH 2.5 AP) levels were adjusted to subtract the background phytase activity (i.e., the percentage of phytase that could be detected at pH 2.5 in the pH 2.5 acid phosphatase assay conditions; Materials and Methods);
[b]All plasmids utilized in these studies were circular and in the whole circular form. Plasmids pFIN-1A and pFIN-1B are single plasmids that contain both the pH 2.5 acid phosphatase (A.P.) and phytase (Phy.) gene sequence.
Transformant = Transformant designation; Promoter for acid phosphatase (A.P)/promoter for physase (Phy));
GA = glucoamylase promoter;
GAPDH = glyceraldehyde 3-phosphate dehydrogenase promoter;
β-T = β-Tubulin promoter;
[c]HFU/ml, acid phosphatase units; PU/ml, phytase units (see Tables 7–10, above);
[d]Ratio HFU/PU = Activity for acid phosphatase (HFU/ml)/Activity for phytase (PU/ml);
[e]Increase is expressed as the fold increase in acid phosphatase (HFU/ml) or phytase (PU/ml) activity in shake flask culture over the activity with ALK0243 in shake flask culture (i.e., activity in HFU/ml or PU/ml, respectively, of transformant per activity in HFU/ml or PU/ml, respectively, of ALK0243).

Figure 17A:
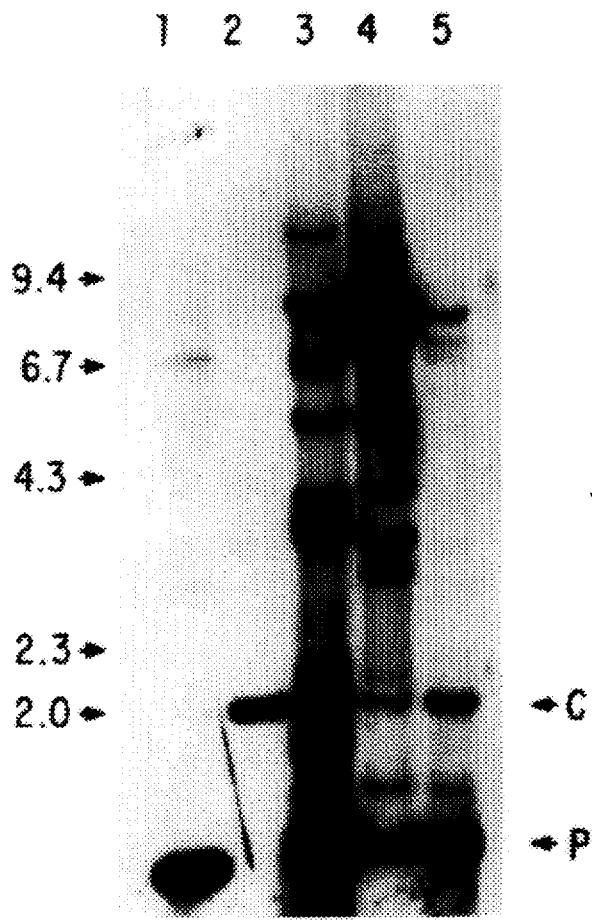
FIG. 17A shows Southern blot analysis of untransformed control ALKO243 (lane 2) and dual-transformed strains (lanes 3, 4 and 5) probed for phytase genes.

Molecular Characterization:

Strains GAX7, GAX-11 and GAX-12 were characterized to determine their relative amounts of gene dosage, message levels and enzyme production. The three transformants all show evidence of tandem integration occurring from the introduction of the phytase transformation vector pFF4. Two of the strains, GAX-7 and GAX-11, also show evidence of multiple integration events (FIG. 17A). The increase in phytase message level over ALKO243 mRNA levels varied from a 17.5-fold increase (for GAX-11) to a 34.4-fold increase (for GAX-12) (FIG. 17B; Table 15).

Figure 17B:
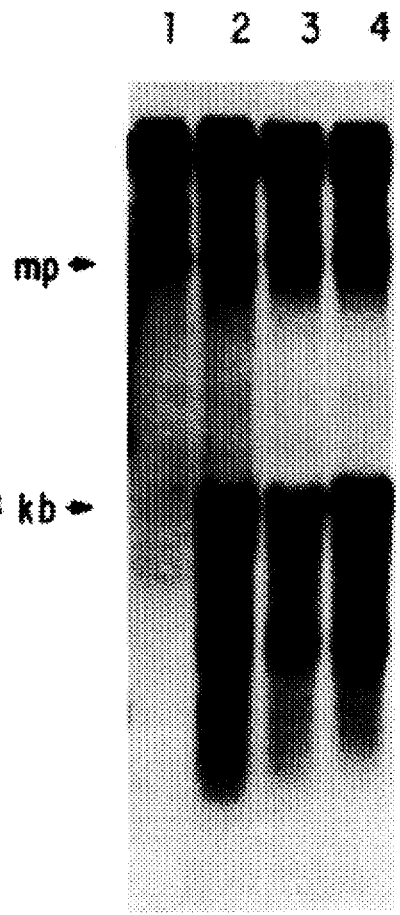
FIG. 17B shows Northern blot analysis of untransformed control (lane 1) and dual-transformed strains (lanes 2, 3 and 4) probed for phytase mRNA.

FIG. 17A shows Southern analysis of DNA copy number of phytase genes in the dual-gene-transformed GAX strains. DNA from dual-enzyme-transformants GAX-7, 11, and 12 was digested with BamHI and XbaI; electrophoresed; blotted; and, the filter was probed with a BamHI /XbaI fragment from pFF-4. Lane 1. pFF-4 plasmid control DNA digested with BamHI/XbaI. Lane 2. ALKO243 untransformed control DNA. Lane 3. Transformant GAX-7 DNA. Lane 4. Transformant GAX-11 DNA. Lane 5. Transformant GAX-12 DNA. p=transformation vector plasmid copy number; c=chromosomal gene copy number. FIG. 17B shows Northern analysis of phytase mRNA transcript levels in the GAX strains of FIG. 17A: 20 mg of total RNA, spiked with 10 ng of mp 18 RF DNA (mp) was electrophoresed, blotted to nitrocellulose, and probed with pFF-1. The phytase transcript is arrowed at 1.4 kb. Lane 1. ALKO243 untransformed control RNA. Lane 2. GAX-7 RNA. Lane 3. GAX-11 RNA. Lane 4. GAX-12 RNA.

TABLE 15

Comparison of Phytase Copy Number, mRNA Levels, and Enzyme Activity for Dual-Enzyme-Transformants[a]

| Strain | Plasmid | Vector Copy No.[b] | mRNA[c] | Activity[d] | Increase[e] |
|---|---|---|---|---|---|
| ALK0243 | Alone | 1 1.0 | 1.0 | 85 | 1 |
| GAX-7 | pFF4 (GA, cir) | 2+ | 24.4 | 38,400 | 452 |
| GAX-11 | pFF4 (GA, cir) | 6+ | 17.5 | 53,000 | 624 |
| GAX-12 | pFF4 (GA, cir) | 8 | 34.4 | 29,000 | 341 |

[a]GA = glucoamylase promoter; cir = circular vector;
[b]Vector copy no. = the number of copies of the vector nucleic acid in the genome of the trassformed cell; + = unquantitated additional copies of phytase present;
[c]mRNA = messenger RNA amplification levels, (as fold-increase over levels in ALK0243);
[d]Activity = phytase activity represented in PU/ml from shake flask cultures as described in Table 10, above;

TABLE 15-continued

Comparison of Phytase Copy Number, mRNA Levels, and Enzyme Activity for Dual-Enzyme-Transformants[a]

| Strain | Plasmid | Vector Copy No.[b] | mRNA[c] | Activity[d] | Increase[e] |
|---|---|---|---|---|---|

[a]Increase is expressed as the fold increase in phytase (PU/ml) activity in shake flask culture over the activity with ALKO243 in shake flask culture (i.e., activity in PU/ml, respectively, of transformant per activity in PU/ml, respectively, of ALKO243).

Figures 18A, 18B:
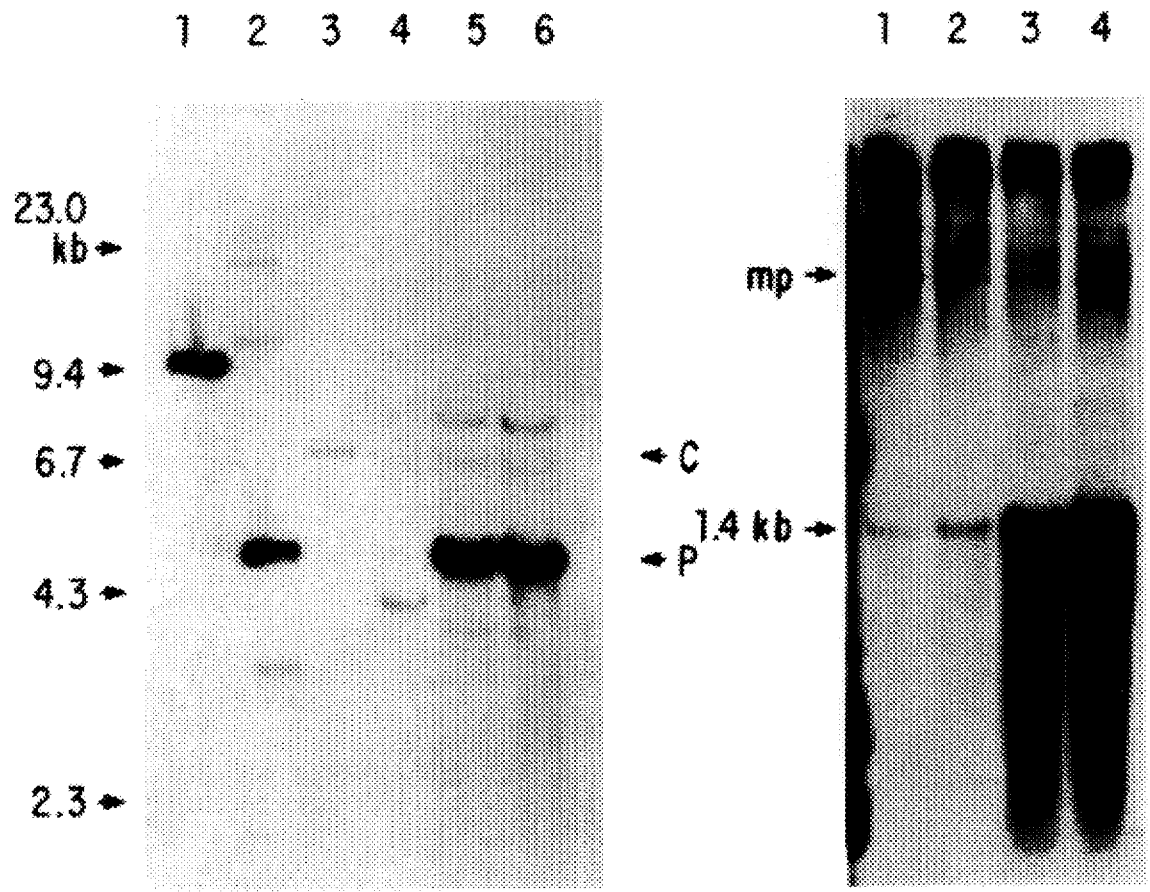
FIG. 18A shows Southern blot analysis of untransformed control ALKO243 (lane 3) and dual-transformed strains (lanes 4, 5 and 6) probed for pH2.5 acid phosphatase genes.
FIG. 18B shows Northern blot analysis of untransformed control ALKO243 (lane 1) and dual-transformed strains (lanes 2, 3 and 4) probed for pH2.5 acid phosphatase mRNA.

Data from a similar analysis by Southern and Northern blotting of the three strains are presented in Table 16, below, for pH2.5 acid phosphatase transformation vector gene sequences. The results show that GAX-7, a pPHO-3 integrant, contained one extra copy of pH2.5 acid phosphatase (as a single integration event); whereas GAX-11 and 12, pPHO-4A integrants, contained extra copies (acquired by tandem integration; FIG. 18A). Message levels for pH2.5 acid phosphatase were increased 2.7-fold (i.e., over levels in ALKO243) in GAX-7, and 10-fold and 15-fold in GAX-11 and GAX-12, respectively (FIG. 18B, Table 16). As observed for the single pH2.5 acid phosphatase gene transformants (i.e., Example 4 above), higher copy numbers were obtained for integration of transformation vector plasmids than with the phytase vectors, but the message levels for pH2.5 acid phosphatase were not corresponding as high as the levels observed with the phytase vectors (Table 16, below).

FIG. 18A shows Southern analysis of DNA copy number of pH2.5 acid phosphatase sequences in GAX dual-gene-transformed strains. All samples were digested with SalI, electrophoresed, blotted to nitrocellulose, and probed with the pH2.5 acid phosphatase gene as isolated in fragments from pAP-3 (Example 3, above). Lane 1. pPHO-3 plasmid DNA control, SalI digested. Lane 2. pPHO-4A plasmid DNA control, SalI digested. Lane 3. Untransformed ALKO243 DNA control. Lane 4. GAX-7 DNA. Lane 5. GAX-11 DNA. Lane 6. GAX-12 DNA.

FIG. 18B shows Northern analysis of mRNA levels of pH2.5 acid phosphatase message expression in dual-enzyme transformed in strains. The pH2.5 acid phosphatase RNA transcript is arrowed. Lane 1. ALKO243 untransformed control RNA. Lane 2. GAX-7 RNA. Lane 3. RNA. GAX-11 RNA. Lane 4. GAX-12 RNA.

TABLE 16

Comparison of pH 2.5 acid phosphatase copy number, mRNA Levels and Enzyme Activity in Dual-Enzyme-Transformants[a]

| Strain | Plasmid | Vector Copy No.[b] | mRNA[c] | Activity[d] | Increase[e] |
|---|---|---|---|---|---|
| ALKO243 | — | 1.0 | 1 | 5,500 | 1.0 |
| GAX-7 | pPH03 (GAP, cir) | 1 | 2.7 | 112,100 | 20 |
| GAX-11 | pPH04A (GA, cir) | 16 | 10.3 | 280,500 | 51 |
| GAX-12 | pPH04A (GA, cir) | 16 | 16.0 | 176,000 | 32 |

[a]GAP = glyceraldehyde 3-phosphate dehydrogenase promoter; GA = glucoamylase promoter; cir = circular vector;
[b]Vector copy no., see Table 15, above;
[c]mRNA = messenger RNA amplification levels, (as fold-increase over Levels in ALKO243);
[d]Activity = pH 2.5 acid phosphatase activity represented in HFU/ml measured in shake flask cultures as described in Table 10, above;

TABLE 16-continued

Comparison of pH 2.5 acid phosphatase copy number, mRNA Levels and Enzyme Activity in Dual-Enzyme-Transformants[a]

| Strain | Plasmid | Vector Copy No.[b] | mRNA[c] | Activity[d] | Increase[e] |
|---|---|---|---|---|---|

[a]Increase is expressed as the fold increase in acid phosphatase (HFU/ml) activity in shake flask culture over the activity with ALKO243 in shake flask culture (i.e., activity in HFU/ml of transformant per activity in HFU/ml of ALKO243).

Materials and Methods:

The materials and methods used herein were the same as those used above (see Example 4).

EXAMPLE 6

Control Of Over-Expression Levels Of Phytase And pH2.5 Acid Phosphatase In Dual-Transformants As described above in Examples 2–5, industrially significant increases in the yields of phytase and pH2.5 acid phosphatase were achieved by transforming a strain of *Aspergillus niger* (i.e., ALKO2268) with transformation vector constructs and selecting for transformants that over-expressed the desired enzymatically active protein. In shake flask fermentations, phytase yields were increased 2,000-fold over enzyme production levels achieved with ALKO243 (Example 4; Table 8, above), and pH2.5 acid phosphatase yields were increased more than 100-fold (Example 4; Table 11, above). These yield increases were considered to result from several factors: most importantly, increased gene dosage, and utilization of effective alternative promoters (i.e., heterologous promoters GA, GAP, GAPDH and the β-tubulin promoter; see Examples 4 and 5, above). Factors controlling expression levels were evaluated further.

The effect of gene dosage on fermentation levels of phytase and acid phosphatase:

The data presented in the Examples 4 and 5 above suggest that relatively large increases in phytase protein resulted from relatively modest increases in gene copy number and mRNA transcript levels. The observed gene copy number increases ranged from three to five additional copies in the phytase over-producing strains. These strains, namely GAE-32, GAK-47, GAL-65, GAM-225 and GAO-248, apparently acquired the additional gene copies by multiple integration events of the recombinant transformation vector plasmid DNA, i.e., rather than by tandem integration. Three of the five strains, GAL-65, GAM-225 and GAO-268, were transformed with linear DNA fragments, from which tandem arrays may be less likely to occur. GAE-32 and GAK-47, however, were transformed with circular vector constructions, which often give rise to tandemly arranged gene copies. Since the transformants were selected on the basis of phytase activity in the enzyme-plate assay (rather than by Southern blot analysis, as is commonly the case), the relative frequency of transformants that had integrated phytase DNA sequences in optimal locations was likely increased. Chromosomal integration site(s) apparently play an important role in phytase gene expression and this screening method selected optimized transformants.

In high producing phytase transformants, messenger RNA levels were elevated seven- to thirteen-fold over ALKO2268, while fermentation levels produced by the cells increased fifty-fold.

The copy number observed in pH2.5 acid phosphatase transformants (Table 12, Example 4; Table 16, Example 5, above) was higher than in phytase transformants (Table 9, Example 4; Table 15, Example 5, above), but the amounts of pH2.5 acid phosphatase message was substantially lower than in phytase transformants. High pH2.5 acid phosphatase over-producer strains GAT-143, GAW-54, GAW-89, GAW-121 and GAW-130 were transformed with vectors having linear DNA from either pPHO-3 or pPHO-4A. Seven to twelve additional gene copies (i.e., vector gene copies) were seen in these transformants, but message levels were only increased by about three- to about seven-fold.

Effects of linear and circular DNA on titers of transformants:

The effects of linear DNA transformation vector constructs and circular vector constructs on phytase enzyme production were evaluated. Overall, circular constructions gave a higher frequency of transformants with increased phytase enzyme production (FIG. 19), but the maximal levels of enzyme produced by the transformants were comparable with linear and circular constructs. For example, circular vector pFF3 gave 8/24 (33%) phytase transformants with enzyme production levels greater than 750 PU. The linear counterpart of pFF3, i.e., pFF8, had two-fold fewer transformants (i.e., that achieved the same threshold level of phytase production), but the transformants that were selected had maximal production levels comparable with pFF8 transformants. When linear fragments were purified and religated, the frequency of higher producers did not increase.

Figure 19:
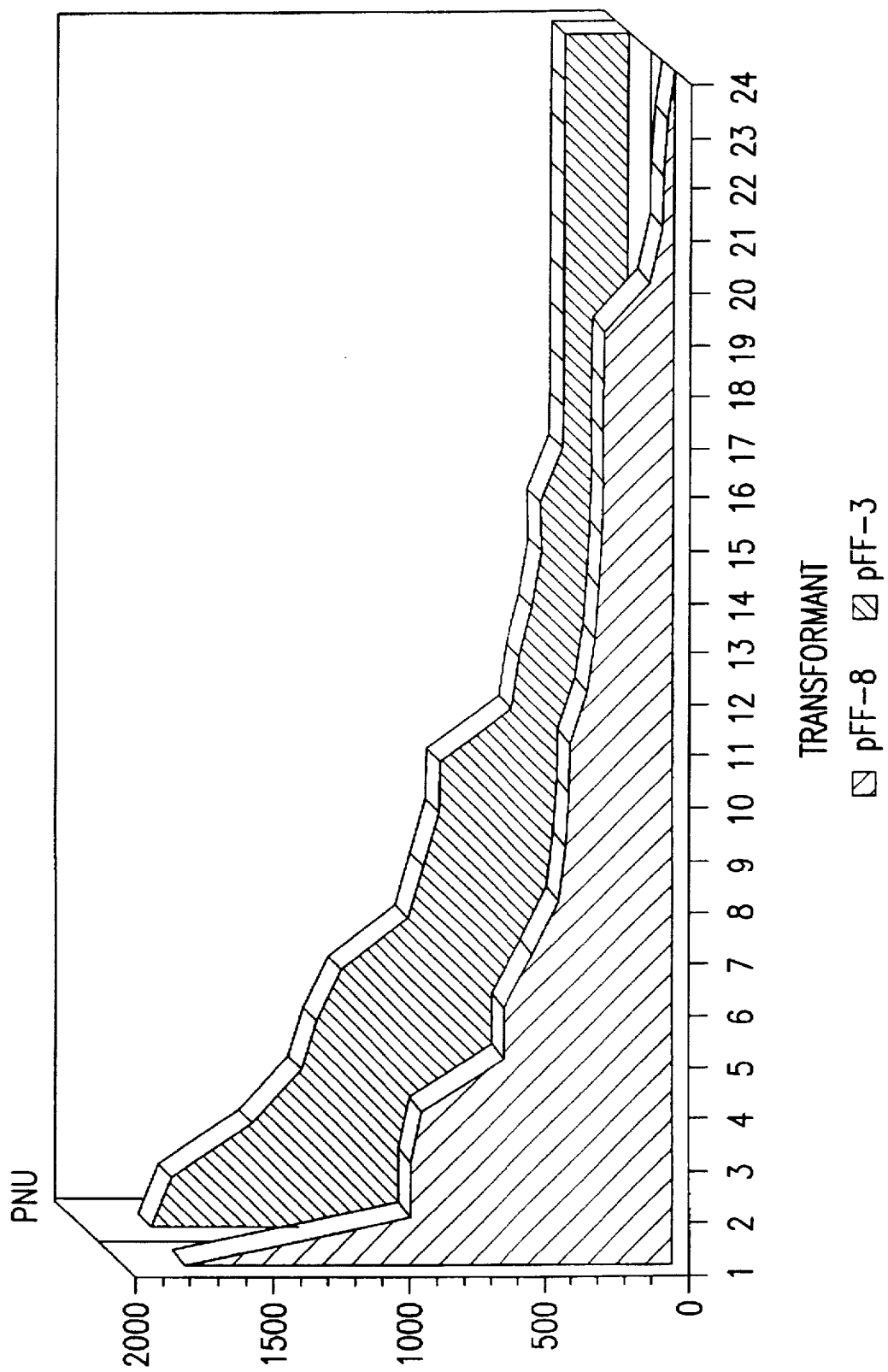
FIG. 19 graphically depicts the levels of phytase activity in twenty-four different transformants using circular or linear plasmid vector constructs (as described in Example 6, below)

FIG. 19. Comparison of the effects of linear and circular DNA on the titers of twenty-four randomly selected phytase transformants. With the circular vector pFF3, 33% of the phytase transformants had levels of enzyme production greater than 750 PNU. Its linear counterpart, pFF8, had two-fold fewer transformants that achieved that same threshold of enzyme production. PNU=phytase normalized units.

Effects of fungal promoters on product titers:

The level of expression of genes in *Aspergillus* may be dependent upon the particular choice of *A. niger* filamentous fungal promoter. The results presented in Examples 4 and 5, above, support the notion that phytase and pH2.5 acid phosphatase can be expressed from a variety of *A. niger* promoters (e.g., including the GA, GAPDH and β-tubulin promoter), as well as the native promoter elements in the 5' regulatory regions of the phytase and pH2.5 acid phosphatase genes. However, the results also show that the maximal levels of enzyme produced in transformants, from expression directed by the different promoters, is different; i.e., the choice of promoter determined the level of expression. While the native phytase and pH2.5 acid phosphatase promoters were effective, the glucoamylase (GA) and GAPDH promoters were significantly better. Production levels of phytase and pH2.5 acid phosphatase in fermentation culture under the control of the GA and GAPDH promoters are shown in FIG. 20.

Figure 20:
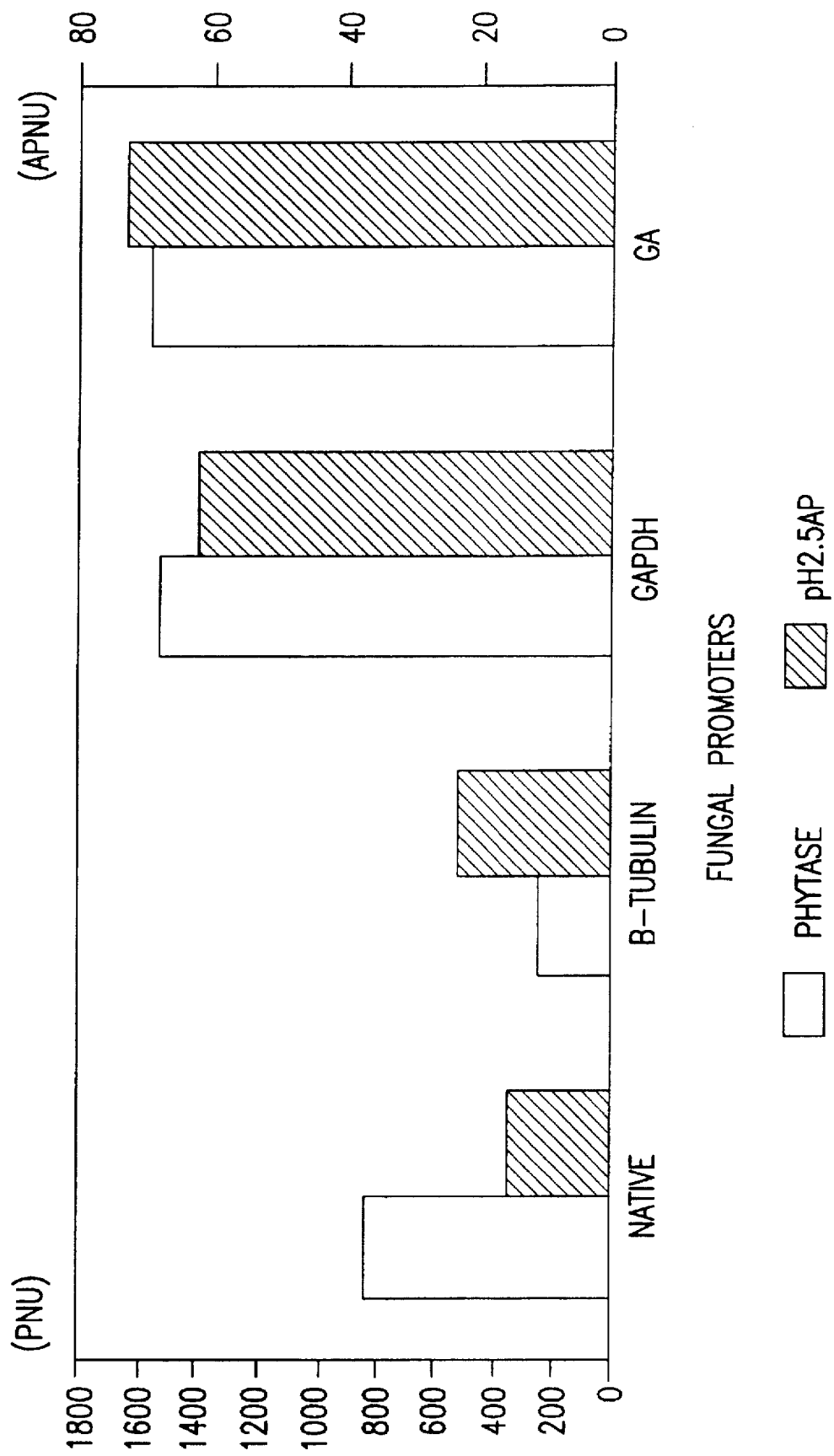
FIG. 20 shows the effects of different promoters on the levels of recombinant phytase activity and pH2.5 acid phosphatase activity in dual-gene-transformed *A. niger* var. awamori strains ALKO243 and ALKO2268, as described in Example 6, below.

FIG. 20. Different fungal promoters used in transforming plasmids influenced the level of phytase and pH2.5 acid phosphatase produced by *A. niger* transformants. The levels of enzyme produced by ten transformants (i.e., with the highest levels for that given promoter), were averaged together. (Data from dual-enzyme-transformants were not used in these calculations.) GAPDH=glyceraldehyde 3-phosphate dehydrogenase. GA=glucoamylase.

The glucoamylase promoter from *Aspergillus* species has been reportedly used to increase expression of several proteins (Ullah et al.,1987). In addition to the GA promoter, the GA sequence contains a glucoamylase signal peptide and propeptide that have been reportedly used in attempts to increase expression (Yamamoto et al., 1970).

To test the effects of the phytase signal sequence on the levels of phytase produced, the signal sequence in the phytase gene was replaced (in construct pFF-11) by a synthetic oligonucleotide containing the fungal glucoamylase putative signal sequence. Surprisingly, instead of increasing the levels of enzyme produced, the insertion of the GA signal sequence actually decreased the levels of phytase produced, as compared with the levels of production achieved in transformants having the native phytase signal sequence (i.e., in the native phytase gene sequence). These results indicate the possible importance of phytase signal sequence in maximizing the levels of production of phytase.

Genes under the control of a glucoamylase promoter may be upregulated (induced) in the presence of starch. To evaluate the effects of such upregulation on levels of phytase production, some pFF-4 and pFF-9 glucoamylase-promoter phytase transformants were cultured in media that had been supplemented with 4% corn starch. Levels of enzyme production were increased an average of 1.4-fold in the latter cultures, although these levels of production were not consistently observed. The highest yields of phytase seen under inducing conditions were 3240–3770PNU. The results indicate that optimization of the media used in the phytase production fermentation broth could result in significantly greater yields of enzyme.

The glyceraldehyde-3-phosphate dehydrogenase (GAPDH) promoter is reportedly a constitutive promoter that may drive high-level expression of a heterologous gene product. The inventors independently cloned the glyceraldehyde phosphate dehydrogenase A gene (gpdA) from *A. niger* ATCC11015 in order to evaluate its effect on phytase and pH2.5 acid phosphatase gene expression in a transformation vector construct introduced into *A. niger* strain ALKO243 or ALKO2268. The levels of enzyme production in transformants having the GAPDH promoter driving expression of phytase and pH2.5 acid phosphatase were nearly identical to the levels achieved, above, using the glucoamylase promoter (FIG. 20). Thus, the GAPDH promoter did not appear to offer any unique opportunities for increased enzyme production. The reasons for this particular behavior are presently unclear; however, such variability in expression between ALKO243 and ALKO2268 may relate to the derivation of ALKO2268 as a mutant from ALKO243, and in this regard ALKO2268 produces only about one-half of the amount of pH2.5 acid phosphatase produced by the parental ALKO243 strain. Thus, it is possible that ALKO2268 is deficient in some limiting factors relating to expression of pH2.5 acid phosphatase. (Such strain-dependent differences in promoter-driven expression were not observed with any other promoters.)

The β-tubulin promoter is also reportedly a promoter capable of driving constitutive expression of genes. To tests its possible effects on phytase and pH2.5 acid phosphatase gene expression, the β-tubulin promoter was isolated from *A. niger* strain 1015. The promoter was introduced into transformation vectors to evaluate its effects on the levels of phytase and pH2.5 acid phosphatase production. Previous studies by the inventors suggested that expression of homologous fungal genes could be increased when driven by the β-tubulin promoter, and that this increase was substantially greater than that which could be achieved through the use of a GAPDH- or GA-promoter (Panlabs, unpublished) Unfortunately, inclusion of a β-tubulin promoter in the phytase transformation vector construct actually decreased the levels of enzyme produced; and, with pH2.5 acid phosphatase only a modest increase in production levels was noted over the levels of production mediated by the native promoter (FIG. 20).

It was also considered possible that production of recombinant phytase and pH2.5 acid phosphatase might be sensitive to phosphate-mediated repression of transcription. In this case, the levels of enzyme produced might be increased by eliminating such conditions in the fermentation culture. In support of the notion of phosphate-mediated repression, cells of both the ALKO243 and ALKO2268 strains produced no detectable phytase when excess phosphate was added to the fermentation culture broth. To study this possibility further, the levels of enzyme produced by phytase transformants having alternative promoters (i.e., GA, GAPDH or β-tubulin) were compared to the levels achieved with the native phytase and pH2.5 acid phosphatase promoters in the transformation vector constructs to see if the use of such an alternative promoter eliminated the putative phosphate-mediated repression. Interestingly, no phytase production was detected in either the phytase or the pH2.5 acid phosphatase promoter when the transformants were grown in the presence of phosphate, supporting the notion of phosphate-mediated repression that cannot be overcome through use of the native promoter integrated into a different chromosomal site. In evaluating the alternative promoters, one transformant with a β-tubulin promoter was able to produce phytase in the presence of phosphate, but it showed a decrease in phytase production by about one-half In contrast, GAPDH-promoter and GA-promoter transformants were not sensitive to phosphate-mediated inhibition to any degree, and yielded similar levels of phytase production in the presence or absence of additional phosphate. Thus, the results suggest that regulatory elements in the 5' regulatory region of the phytase and pH2.5 acid phosphatase genes may be useful for directing phosphate-mediated repression of gene expression, and that insertion of alternative promoters into the 5' regions of these genes can overcome these native regulatoryconstraints and increase production yields.

The identification of rate limiting factors, whether energy or secretion related, may further increase yields of phytase and pH2.5 acid phosphatase. Other factors such as media optimization, increased or stabilized gene transcription levels of pH2.5 acid phosphatase, or classical mutagenesis screening of high producers could have additional impacts on product yield. Elevated gene dosage and the use of alternative promoters have dramatically increased production yields over native promoters and escaped negative regulatory constraints. The cloning and reintroduction of the genes for phytase and pH2.5 acid phosphatase has resulted in commercially significant levels of these enzymes for use as animal feed supplements. Rational design of homologous gene over-expression can be applied to increase the yields of other fungal industrial products, and potentially give a better understanding of the mechanisms required for heterologous expression.

Materials and Methods:

The materials and methods used in this example are the same as those used in Example 4, above.

While the preferred embodiment of the invention has been illustrated and described, it will be appreciated that various changes can be made therein without departing from the spirit and scope of the invention.

CITATIONS

Arima, K. et al., "The nucleotide sequence of the yeast PH05 gene: a putative precursor of repressible acid phosphatase contains a signal peptide." Nucleic Acids Res. 11:1657–1672, 1983.

Bajwa, W. et al., "Structural analysis of the two tandemly repeated acid phosphatase genes in yeast." Nucleic Acids Res. 11:7721–7739, 1983.

Elliot, S. et al., "Isolation and characterization of the structural gene for secreted acid phosphatase from Schizosaccharomyces pombe." J. Biol. Chem. 261:2936–2941, 1986.

Touati, E. et al., "The structure of the promoter and amino terminal region of pH2.5 acid phosphatase structural gene (appA) of E. coli: a negative control of transcription mediated by cyclic AMP, " Biochemie 69:215–221, 1987.

Han, Y. W., et al., "Phosphatase production by Aspergillus ficuum," Journal of Industrial Microbiology 1:295–301, 1987.

Himeno, M. et al., "Isolation and Sequencing of a cDNA Clone Encoding Acid Phosphatase in Rat Liver Lysosomes," Biochem. Biophys. Res. Comm. 162:1044–1053, 1989.

Kalkknen, N. et al. "A Gas-Pulsed-Liquid-Phase Sequencer Constructed From a Beckman 8900 By Using Applied Biosystems Delivery and Cartridge Blocks," J. Prot. Chem. 7:242–243, 1988.

Lloyd, A. T. et al., "Codon usage in Aspergillus nidulans, " Mol Gen Genet 230:288–294, 1991.

McAda, P. C. et al., "A Yeast Mitochondrial Chelator-Sensitive Protease That Processes Cytoplasmically Synthesized Protein Precursors," Isolation from Yeast and Assay in Methods in Enzymology 97:337–344, 1983.

Needleman, S. B. et al., "General Method Applicable to the Search for Similarities in the Amino Acid Sequence of Two Proteins ." J. Mol. Biol. 48:443–453, 1970.

Pohlmann, R. et al., EMBO Journal 7:2343–2350, 1988.

Rambosek, J. et al., "Recombinant DNA in Filamentous Fungi: Progress and Prospects," CRC Critical Reviews in Biotechnology 6:357–393, 1987.

Roiko, L. et al., Gene 89:223–229, 1990.

Sanger et al., Proc. Nat. Acad. Sci. USA 74:5463–5467, 1977.

Shieh, T. R. et al., "Regulation of the Formation of Acid Phosphatase by Inorganic Phosphate in Aspergillus ficuum," Journal of Bacteriology 100:1161–1165, 1969.

Shieh, T. R. et al., "Survey of Microorganisms for the Production of Extracellular Phytase." Appl Microbiol 6:1348–1351, 1968.

Standen, R., Nucleic Acids Res. 12:505–519, 1984.

Tailor, P. et al., Nucleic Acids Research 18:4921–4928, 1990.

Tilburn, J. et al., Gene 26:205–221, 1983.

Ullah, H. J. et al., "Cyclohexanedione Modification Of Arginine at the Active Site of Aspergillus ficuum Phytase," Biochemical and Biophysical Research Communications 178(1):45–53, 1991.

Ullah, H. J., "Aspergillus ficuum Phytase: Partial Primary Structure, Substrate Selectivity, and Kinetic Characterization," Preparative Biochemistry 18(4):459–471, 1988.

Ullah, H. J., et al., "Purification, N-terminal Amino Acid Sequence and Characterization of pH2.5 optimum acid phosphatase (E.C. 3.1.3.2) from Aspergillus ficuum, " Preparative Biochemistry, 17(4):397–422, 1987.

Yamamoto, K. R. et al., "Rapid Bacteriophage Sedimentation in the Presence of Polyethylene Glycol and its Application to Large-Scale Virus Purification," Virology 40:734–744, 1970.

Shieh and Ware, U.S. Patent No. 3,297,548.

Nelson, T. S. et al., *J. Nutrition* 101:1289–1294, 1971.

Sandberg, A-S. et al., *Journal of Nutrition* 117:2061–2065, 1987.

---

What is claimed is:

1. A transformed recombinant host cell transformed with a first nucleic acid molecule comprising a nucleotide sequence encoding a phytase and a second nucleic acid molecule comprising a nucleotide sequence selected from the group consisting of
   (a) a nucleotide sequence encoding a pH 2.5 acid phosphatase having the amino acid sequence of amino acids 1–479 of SEQ ID No. 4; and
   (b) a nucleotide sequence encoding a pH 2.5 acid phosphatase, wherein said nucleotide sequence encoding said pH 2.5 acid phosphatase
      (i) hybridizes to the complement of the DNA sequence set forth in the coding region of SEQ ID No. 3; and
      (ii) remains hybridized to the complement of the DNA sequence set forth in the coding region of SEQ ID No. 3 when subjected to a hybridization solution at 68° C. for 2 hours, wherein the salt in said hybridization solution is provided by 0.1×SSC, and
   wherein said host cell secretes the active phytase encoded by said nucleotide sequence encoding said phytase,
   wherein said host cell secretes the active pH 2.5 acid phosphatase encoded by said nucleotide sequence encoding said pH 2.5 acid phosphatase, and
   wherein the amount of said phytase and the amount of said phosphatase secreted by said host cell are secreted in a predetermined, desired ratio.

2. The transformed recombinant host cell of claim 1, wherein said first nucleic acid molecule comprises a nucleotide sequence encoding a phytase having the amino acid sequence of amino acids 1–467 of SEQ ID No. 2.

3. The transformed recombinant host cell of claim 2, wherein said first nucleic acid molecule comprises the nucleotide sequence set forth in the coding region of SEQ ID No. 1.

4. The transformed recombinant host cell of claim 1, wherein said second nucleic acid molecule comprises a nucleotide sequence encoding a pH 2.5 acid phosphatase having the amino acid sequence of amino acids 1–479 of SEQ ID No. 4.

5. The transformed recombinant host cell of claim 4, wherein said second nucleic acid molecule comprises the nucleotide sequence set forth in the coding region of SEQ ID No. 3.

6. The transformed recombinant host cell of claim 1, wherein said second nucleicacid molecule comprises a nucleotide sequence encoding a pH 2.5 acid phosphatase, wherein said nucleotide sequence (i) hybridizes to the complement of the DNA sequence set forth in the coding region of SEQ ID No. 3; and
(ii) remains hybridized to the complement of the DNA sequence set forth in the coding region of SEQ ID No. 3 when subjected to a hybridization solution at 68° C. for 2 hours, wherein the salt in said hybridization solution is provided by 0.1×SSC.

7. The transformed recombinant host cell of claim 1, wherein said phytase secreted by said cell has an enzyme activity per milliliter that is at least about 2-fold greater than the phytase enzyme activity secreted by ALKO243 (ATCC #38854) or said phosphatase secreted by said cell has an enzyme activity that is at least about 10-fold greater than the phosphatase enzyme activity secreted by ALKO243 (ATCC #38854).

8. The transformed recombinant host cell of claim 1, wherein said phosphatase secreted by said cell has an enzyme activity per milliliter that is about 3-fold to about 16-fold greater than the enzyme activity of said phytase secreted by said cell.

9. The transformed recombinant host cell of claim 1, wherein said cell is selected from the group consisting of a bacterium and a fungus.

10. The transformed recombinant host cell of claim 9, wherein said bacterium is selected from the group consisting of *E. coli* and *Bacillus*.

11. The transformed recombinant host cell of claim 9, wherein said fungus is a filamentous fungus.

12. The transformed recombinant host cell of claim 11, wherein said filamentous fungus is selected from the group consisting of *Aspergillus, Trichoderma, Penicillium, Cephalosa* and *Rhizopus*.

13. The transformed recombinant host cell of claim 12, wherein said filamentous fungus is *Aspergillus*.

14. The transformed recombinant host cell of claim 13, wherein said filamentous fungus is *Aspergillus niger*.

15. The transformed recombinant host cell of claim 14, wherein said *Aspergillus niger* is a strain selected from the group consisting of GAX-11, GAX-12, GBE-14, GBH-134, GBH-157, GBJ-76, and GBJ-82.

16. A transformed recombinant host cell transformed with a nucleic acid molecule comprising a first nucleotide sequence encoding a phytase and a second nucleotide sequence selected from the group consisting of
   (a) a nucleotide sequence encoding a pH 2.5 acid phosphatase having the amino acidsequence of amino acids 1–479 of SEQ ID No. 4; and
   (b) a nucleotide sequence encoding a pH 2.5 acid phosphatase, wherein said nucleotide sequence encoding said pH 2.5 acid phosphatase (i) hybridizes to the complement of the DNA sequence set forth in the coding region of SEQ ID No. 3; and (ii) remains hybridized to the complement of the DNA sequence set forth in the coding region of SEQ ID No. 3 when subjected to a hybridization solution at 68° C. for 2 hours, wherein the salt in said hybridization solution is provided by 0.1×SSC, and wherein said host cell secretes the active phytase encoded by said first nucleotide sequence encoding said phytase, wherein said host cell secretes the active pH 2.5 acid phosphatase encoded by said second nucleotide sequence encoding said pH 2.5 acid phosphatase, and wherein the amount of said phytase and the amount of said phosphatase secreted by said host cell are secreted in a predetermined desired ratio.

17. The transformed recombinant host cell of claim 16, wherein said first nucleotide sequence encodes a phytase having the amino acid sequence of amino acids 1–467 of SEQ ID No. 2.

18. The transformed recombinant host cell of claim 16, wherein said first nucleotide sequence is set forth in the coding region of SEQ ID No. 1.

19. The transformed recombinant host cell of claim 16, wherein said second nucleotide sequence encodes a pH 2.5 acid phosphatase having the amino acid sequence of amino acids 1–479 of SEQ ID No. 4.

20. The transformed recombinant host cell of claim 19, wherein said second nucleotide sequence is set forth in the coding region of SEQ ID No. 3.

21. The transformed recombinant host cell of claim 16, wherein said second nucleotide sequence encodes a pH 2.5 acid phosphatase, wherein said second nucleotide sequence encoding said pH 2.5 acid phosphatase (i) hybridizes to the complement of the DNA sequence set forth in the coding region of SEQ ID No. 3; and (ii) remains hybridized to the complement of the DNA sequence set forth in the coding region of SEQ ID No. 3 when subjected to a hybridization solution at 68° C. for 2 hours, wherein the salt in said hybridization solution is provided by 0.1×SSC.

22. The transformed recombinant host cell of claim 16, wherein said phytase secreted by said cell has an enzyme activity per milliliter that is at least about 2-fold greater than the phytase enzyme activity secreted by ALKO243 (ATCC #38854) or said pliosphatase secreted by said cell has an enzyme activity that is at least about 10-fold greater than the phosphatase enzyme activity secreted by ALKO243 (ATCC #38854).

23. The transformed recombinant host cell of claim 19, wherein said secreted phosphatase has an enzyme activity per milliliter that is about 3-fold to about 16-fold greater than the enzyme activity of said secreted phytase.

24. The transformed recombinant host cell of claim 16, wherein said cell is selected from the group consisting of a bacterium and a fungus.

25. The transformed recombinant host cell of claim 24, wherein said bacterium is selected from the group consisting of *E. coli* and *Bacillus*.

26. The transformed recombinant host cell of claim 24, wherein said fungus is a filamentous fungus.

27. The transformed recombinant host cell of claim 26, wherein said filamentous fungus is selected from the group consisting of *Aspergillus, Trichoderma, Bacillium, Cephalosporium,* and *Rhizopus*.

28. The transformed recombinant host cell of claim 27, wherein said filamentous fungus is *Aspergillus*.

29. The transformed recombinant host cell of claim 28, wherein said filamentous fungus is *Aspergillus niger*.

30. The transformed recombinant host cell of claim 29, wherein said *Aspergillus niger* is a strain selected from the group consisting of GBJ-9, GBJ-10, GBJ-13, GBJ-16, GBJ-26, GBJ-27, GBJ-28, GBJ-31, GBJ-35, GBJ-38, GBJ-40.

31. An enzymatically active mixture comprising an enzymatically active phytase and the enzymatically active pH 2.5 acid phosphatase encoded by the coding region of SEQ ID No. 3, wherein the ratio of the enzyme activity of said pH 2.5 acid phosphatase to the enzyme activity of said phytase is from about 3:1 to about 16:1.

32. A feed comprising the mixture of claim 31.

33. A method of increasing the release of minerals from phytate complexes in an animal diet, said method comprising feeding said animal the feed of claim 32.

34. A method of increasing the release of phosphates from phytate complexes in a plant material, said method comprising incubating the mixture of claim 31 with said plant material.

35. An enzymatically active mixture comprising an active phytase and the active pH 2.5 acid phosphatase encoded by a nucleotide sequence that (i) hybridizes to the complement of the DNA sequence set forth in the coding regions of SEQ ID No. 3; and (ii) remains hybridized to the complement of the DNA sequence set forth in the coding regions of SEQ ID No. 3 when subjected to a hybridization solution at 68° C. for 2 hours, wherein the salt in said hybridization solution is provided by 0.1×SSC, and wherein the ratio of the enzyme activity of said pH 2.5 acid phosphatase to the enzyme activity of said phytase is from about 3:1 to about 16:1.

36. A feed comprising the mixture of claim 35.

37. A method of increasing the release of minerals from phytate complexes in an animal diet, said method comprising feeding said animal the feed of claim 36.

38. A method of increasing the release of phosphates from phytate complexes in a plant material, said method comprising incubating the mixture of claim 35 with said plant material.

* * * * *

SEQUENCE LISTING ( 1 ) GENERAL INFORMATION:

( i i i ) NUMBER OF SEQUENCES: 94

( 2 ) INFORMATION FOR SEQ ID NO:1:

( i ) SEQUENCE CHARACTERISTICS:
        ( A ) LENGTH: 2379 base pairs
        ( B ) TYPE: nucleic acid
        ( C ) STRANDEDNESS: both
        ( D ) TOPOLOGY: linear ( i i ) MOLECULE TYPE: DNA (genomic)

( i x ) FEATURE:
        ( A ) NAME/KEY: CDS
        ( B ) LOCATION: join(404..447, 550..1906)

( x i ) SEQUENCE DESCRIPTION: SEQ ID NO:1:

```
TGATGGCGGC  CTAGGGCATC  CAGGCACCCT  TTCCCAACGG  GGGAACTTCC  GTTGTCCACG        60

TGCCCTGGTT  CAGCCAATCA  AAGCGTCCCA  CGGCAATGCT  GGATCAACGA  TCAACTTGAA       120

TGCAATAAAT  GAAGATGCAA  CTAACACCAT  CTGTTGCCTT  TCTCTCGAGA  AAGCTCCTCC       180

ACTTCTCACA  CTAGATTTAT  CCGTTCCTTG  TCGACTTCCC  GTCCCATTCG  GCCTCGTCCA       240

CTGAAGATCT  ATCCCACCAT  TGCACGTGGG  CCACCTTTGT  GAGCTTCTAA  CCTGAACTGG       300

TAGAGTATCA  CACAACATGC  GAAAGTGGGA  TGAAGGGGTT  ATATGAGGAC  CGTCCGGTCC       360

GGCGCGATGG  CCGTAGCTGC  CAATCGCTGC  TGTGCAAGAA  ATTTCTTCTC  ATAGGCATC        419
```

```
ATG  GGC  GTC  TCT  GCT  GTT  CTA  CTT  CCT  TTG  TAT  CTC  CTA  GCT  GGG       TATGCTA  471
Met  Gly  Val  Ser  Ala  Val  Leu  Leu  Pro  Leu  Tyr  Leu  Leu  Ala  Gly
 1              5                        10                       15
```

```
AGCACCGCTA  TCTAAGTCTG  ATAAGGACCC  TCTTTGCCGA  GGGCCCCTGA  AGCTCGGACT       531

GTGTGGGACT  ACTGATCGCT  GACAATCTGT  GCAGA       GTC  ACC  TCC  GGA  CTG  GCA  584
                                                Val  Thr  Ser  Gly  Leu  Ala
                                                                         20
```

```
GTC  CCC  GCC  TCG  AGA  AAT  CAA  TCC  ACT  TGC  GAT  ACG  GTC  GAT  CAA  GGG      632
Val  Pro  Ala  Ser  Arg  Asn  Gln  Ser  Thr  Cys  Asp  Thr  Val  Asp  Gln  Gly
               25                        30                       35

TAT  CAA  TGC  TTC  TCC  GAG  ACT  TCG  CAT  CTT  TGG  GGT  CAA  TAC  GCG  CCG      680
Tyr  Gln  Cys  Phe  Ser  Glu  Thr  Ser  His  Leu  Trp  Gly  Gln  Tyr  Ala  Pro
               40                        45                       50

TTC  TTC  TCT  CTG  GCA  AAC  GAA  TCG  GCC  ATC  TCC  CCT  GAT  GTG  CCC  GCC      728
Phe  Phe  Ser  Leu  Ala  Asn  Glu  Ser  Ala  Ile  Ser  Pro  Asp  Val  Pro  Ala
 55                       60                       65

GGT  TGC  AGA  GTC  ACT  TTC  GCT  CAG  GTC  CTC  TCC  CGT  CAT  GGA  GCG  CGG      776
Gly  Cys  Arg  Val  Thr  Phe  Ala  Gln  Val  Leu  Ser  Arg  His  Gly  Ala  Arg
 70                       75                       80                       85

TAT  CCG  ACC  GAG  TCC  AAG  GGC  AAG  AAA  TAC  TCC  GCT  CTC  ATT  GAG  GAG      824
Tyr  Pro  Thr  Glu  Ser  Lys  Gly  Lys  Lys  Tyr  Ser  Ala  Leu  Ile  Glu  Glu
                    90                       95                      100

ATC  CAG  CAG  AAC  GTG  ACC  ACC  TTT  GAT  GGA  AAA  TAT  GCC  TTC  CTG  AAG      872
Ile  Gln  Gln  Asn  Val  Thr  Thr  Phe  Asp  Gly  Lys  Tyr  Ala  Phe  Leu  Lys
                   105                      110                      115

ACA  TAC  AAC  TAC  AGC  TTG  GGT  GCA  GAT  GAC  CTG  ACT  CCC  TTC  GGA  GAG      920
Thr  Tyr  Asn  Tyr  Ser  Leu  Gly  Ala  Asp  Asp  Leu  Thr  Pro  Phe  Gly  Glu
                   120                      125                      130
```

| | | | | | | | | | | | | | | | | |
|---|---|---|---|---|---|---|---|---|---|---|---|---|---|---|---|---|
| CAG | GAG | CTA | GTC | AAC | TCC | GGC | ATC | AAG | TTC | TAC | CAG | CGA | TAC | GAA | TCG | 968 |
| Gln | Glu | Leu | Val | Asn | Ser | Gly | Ile | Lys | Phe | Tyr | Gln | Arg | Tyr | Glu | Ser | |
| | 135 | | | | 140 | | | | | 145 | | | | | | |
| CTC | ACA | AGG | AAC | ATC | ATT | CCG | TTC | ATC | CGA | TCC | TCT | GGC | TCC | AGC | CGC | 1016 |
| Leu | Thr | Arg | Asn | Ile | Ile | Pro | Phe | Ile | Arg | Ser | Ser | Gly | Ser | Ser | Arg | |
| 150 | | | | | 155 | | | | | 160 | | | | | 165 | |
| GTG | ATC | GCC | TCC | GGC | GAG | AAA | TTC | ATT | GAG | GGC | TTC | CAG | AGC | ACC | AAG | 1064 |
| Val | Ile | Ala | Ser | Gly | Glu | Lys | Phe | Ile | Glu | Gly | Phe | Gln | Ser | Thr | Lys | |
| | | | | 170 | | | | | 175 | | | | | 180 | | |
| CTG | AAG | GAT | CCT | CGT | GCC | CAG | CCG | GGC | CAA | TCG | TCG | CCC | AAG | ATC | GAC | 1112 |
| Leu | Lys | Asp | Pro | Arg | Ala | Gln | Pro | Gly | Gln | Ser | Ser | Pro | Lys | Ile | Asp | |
| | | | 185 | | | | | 190 | | | | | 195 | | | |
| GTG | GTC | ATT | TCC | GAG | GCC | AGC | TCA | TCC | AAC | AAC | ACT | CTC | GAC | CCA | GGC | 1160 |
| Val | Val | Ile | Ser | Glu | Ala | Ser | Ser | Ser | Asn | Asn | Thr | Leu | Asp | Pro | Gly | |
| | | 200 | | | | | 205 | | | | | 210 | | | | |
| ACC | TGC | ACT | GTC | TTT | GAA | GAC | AGC | GAA | TTG | GCC | GAT | ACC | GTC | GAA | GCC | 1208 |
| Thr | Cys | Thr | Val | Phe | Glu | Asp | Ser | Glu | Leu | Ala | Asp | Thr | Val | Glu | Ala | |
| | 215 | | | | | 220 | | | | | 225 | | | | | |
| AAT | TTC | ACC | GCC | ACG | TTC | GCC | CCC | TCC | ATT | CGT | CAA | CGT | CTG | GAG | AAC | 1256 |
| Asn | Phe | Thr | Ala | Thr | Phe | Ala | Pro | Ser | Ile | Arg | Gln | Arg | Leu | Glu | Asn | |
| 230 | | | | | 235 | | | | | 240 | | | | | 245 | |
| GAC | CTG | TCT | GGC | GTG | ACT | CTC | ACA | GAC | ACA | GAA | GTG | ACC | TAC | CTC | ATG | 1304 |
| Asp | Leu | Ser | Gly | Val | Thr | Leu | Thr | Asp | Thr | Glu | Val | Thr | Tyr | Leu | Met | |
| | | | | 250 | | | | | 255 | | | | | 260 | | |
| GAC | ATG | TGC | TCC | TTC | GAC | ACC | ATC | TCC | ACC | AGC | ACC | GTC | GAC | ACC | AAG | 1352 |
| Asp | Met | Cys | Ser | Phe | Asp | Thr | Ile | Ser | Thr | Ser | Thr | Val | Asp | Thr | Lys | |
| | | | 265 | | | | | 270 | | | | | 275 | | | |
| CTG | TCC | CCC | TTC | TGT | GAC | CTG | TTC | ACC | CAT | GAC | GAA | TGG | ATC | CAC | TAC | 1400 |
| Leu | Ser | Pro | Phe | Cys | Asp | Leu | Phe | Thr | His | Asp | Glu | Trp | Ile | His | Tyr | |
| | | 280 | | | | | 285 | | | | | 290 | | | | |
| GAC | TAC | CTC | CAG | TCC | CTG | AAA | AAA | TAC | TAC | GGC | CAT | GGC | GCA | GGT | AAC | 1448 |
| Asp | Tyr | Leu | Gln | Ser | Leu | Lys | Lys | Tyr | Tyr | Gly | His | Gly | Ala | Gly | Asn | |
| | 295 | | | | | 300 | | | | | 305 | | | | | |
| CCG | CTC | GGC | CCG | ACC | CAG | GGC | GTC | GGC | TAC | GCT | AAC | GAG | CTC | ATC | GCC | 1496 |
| Pro | Leu | Gly | Pro | Thr | Gln | Gly | Val | Gly | Tyr | Ala | Asn | Glu | Leu | Ile | Ala | |
| 310 | | | | | 315 | | | | | 320 | | | | | 325 | |
| CGT | CTC | ACC | CAC | TCG | CCT | GTC | CAC | GAT | GAC | ACC | AGC | TCC | AAC | CAC | ACC | 1544 |
| Arg | Leu | Thr | His | Ser | Pro | Val | His | Asp | Asp | Thr | Ser | Ser | Asn | His | Thr | |
| | | | | 330 | | | | | 335 | | | | | 340 | | |
| TTG | GAC | TCG | AAC | CCA | GCT | ACC | TTC | CCG | CTC | AAC | TCT | ACT | CTC | TAC | GCG | 1592 |
| Leu | Asp | Ser | Asn | Pro | Ala | Thr | Phe | Pro | Leu | Asn | Ser | Thr | Leu | Tyr | Ala | |
| | | | 345 | | | | | 350 | | | | | 355 | | | |
| GAC | TTT | TCC | CAC | GAT | AAC | GGC | ATC | ATC | TCT | ATC | CTC | TTT | GCT | TTG | GGT | 1640 |
| Asp | Phe | Ser | His | Asp | Asn | Gly | Ile | Ile | Ser | Ile | Leu | Phe | Ala | Leu | Gly | |
| | | 360 | | | | | 365 | | | | | 370 | | | | |
| CTG | TAC | AAC | GGC | ACT | AAG | CCG | CTG | TCT | ACC | ACG | ACC | GTG | GAG | AAT | ATC | 1688 |
| Leu | Tyr | Asn | Gly | Thr | Lys | Pro | Leu | Ser | Thr | Thr | Thr | Val | Glu | Asn | Ile | |
| | 375 | | | | | 380 | | | | | 385 | | | | | |
| ACC | CAG | ACA | GAT | GGG | TTC | TCG | TCT | GCT | TGG | ACG | GTT | CCG | TTT | GCT | TCG | 1736 |
| Thr | Gln | Thr | Asp | Gly | Phe | Ser | Ser | Ala | Trp | Thr | Val | Pro | Phe | Ala | Ser | |
| 390 | | | | | 395 | | | | | 400 | | | | | 405 | |
| CGT | CTG | TAC | GTC | GAG | ATG | ATG | CAG | TGC | CAG | GCC | GAG | CAG | GAG | CCG | CTG | 1784 |
| Arg | Leu | Tyr | Val | Glu | Met | Met | Gln | Cys | Gln | Ala | Glu | Gln | Glu | Pro | Leu | |
| | | | | 410 | | | | | 415 | | | | | 420 | | |
| GTC | CGT | GTC | TTG | GTT | AAT | GAT | CGC | GTT | GTC | CCG | CTG | CAT | GGG | TGT | CCA | 1832 |
| Val | Arg | Val | Leu | Val | Asn | Asp | Arg | Val | Val | Pro | Leu | His | Gly | Cys | Pro | |
| | | | 425 | | | | | 430 | | | | | 435 | | | |
| ATT | GAT | GCT | TTG | GGG | AGA | TGT | ACC | CGG | GAT | AGC | TTT | GTG | AGG | GGG | TTG | 1880 |
| Ile | Asp | Ala | Leu | Gly | Arg | Cys | Thr | Arg | Asp | Ser | Phe | Val | Arg | Gly | Leu | |
| | | 440 | | | | | 445 | | | | | 450 | | | | |

| AGC | TTT | GCT | AGA | TCT | GGG | GGT | GAT | TGG | GCG | GAG | TGT | TCT | GCT | 1922 |
|-----|-----|-----|-----|-----|-----|-----|-----|-----|-----|-----|-----|-----|-----|------|
| Ser | Phe | Ala | Arg | Ser | Gly | Gly | Asp | Trp | Ala | Glu | Cys | Ser | Ala |      |
|     | 455 |     |     |     | 460 |     |     |     |     | 465 |     |     |     |      |

```
TAGCTGAACT ACCTTGATGG ATGGTATGTA TCAATCAGAG TACATATCAT TACTTCATGT      1982
ATGTATTTAC GAAGATGTAC ATATCGAAAT ATCGATGATG ACTACTCCGG TAGATATTTG      2042
GTCCCCTTCT ATCCTTCGTT CCACAACCAT CGCACTCGAC GTACAGCATA ATACAACTTC      2102
AGCATTAACA AACGAACAAA TAATATTATA CACTCCTCCC CAATGCAATA ACAACCGCAA      2162
TTCATACCTC ATATAGATAC AATACAATAC ATCCATCCCT ACCCTCAAGT CCACCCATCC      2222
CATAATCAAA TCCCTACTTA CTCCTCCCCC TTCCCAGAAC CCACCCCCGA AGGAGTAATA      2282
GTAGTAGTAG AAGAAGCAGA CGACCTCTCC ACCAACCTCT TCGGCCTCTT ATCCCCATAC      2342
GCTATACACA CACGAACACA CCAAATAGTC AGCATGC                               2379
```

( 2 ) INFORMATION FOR SEQ ID NO:2:

( i ) SEQUENCE CHARACTERISTICS:
        ( A ) LENGTH: 467 amino acids
        ( B ) TYPE: amino acid
        ( C ) STRANDEDNESS: single
        ( D ) TOPOLOGY: Not Relevant ( i i ) MOLECULE TYPE: protein ( x i ) SEQUENCE DESCRIPTION: SEQ ID NO:2:

```
Met Gly Val Ser Ala Val Leu Leu Pro Leu Tyr Leu Leu Ala Gly Val
 1               5                  10                  15

Thr Ser Gly Leu Ala Val Pro Ala Ser Arg Asn Gln Ser Thr Cys Asp
            20                  25                  30

Thr Val Asp Gln Gly Tyr Gln Cys Phe Ser Glu Thr Ser His Leu Trp
        35                  40                  45

Gly Gln Tyr Ala Pro Phe Phe Ser Leu Ala Asn Glu Ser Ala Ile Ser
    50                  55                  60

Pro Asp Val Pro Ala Gly Cys Arg Val Thr Phe Ala Gln Val Leu Ser
65                  70                  75                  80

Arg His Gly Ala Arg Tyr Pro Thr Glu Ser Lys Gly Lys Lys Tyr Ser
                85                  90                  95

Ala Leu Ile Glu Glu Ile Gln Gln Asn Val Thr Thr Phe Asp Gly Lys
                100                 105                 110

Tyr Ala Phe Leu Lys Thr Tyr Asn Tyr Ser Leu Gly Ala Asp Asp Leu
            115                 120                 125

Thr Pro Phe Gly Glu Gln Glu Leu Val Asn Ser Gly Ile Lys Phe Tyr
        130                 135                 140

Gln Arg Tyr Glu Ser Leu Thr Arg Asn Ile Ile Pro Phe Ile Arg Ser
145                 150                 155                 160

Ser Gly Ser Ser Arg Val Ile Ala Ser Gly Glu Lys Phe Ile Glu Gly
                165                 170                 175

Phe Gln Ser Thr Lys Leu Lys Asp Pro Arg Ala Gln Pro Gly Gln Ser
                180                 185                 190

Ser Pro Lys Ile Asp Val Val Ile Ser Glu Ala Ser Ser Ser Asn Asn
            195                 200                 205

Thr Leu Asp Pro Gly Thr Cys Thr Val Phe Glu Asp Ser Glu Leu Ala
        210                 215                 220

Asp Thr Val Glu Ala Asn Phe Thr Ala Thr Phe Ala Pro Ser Ile Arg
225                 230                 235                 240

Gln Arg Leu Glu Asn Asp Leu Ser Gly Val Thr Leu Thr Asp Thr Glu
                245                 250                 255
```

| | | | | | | | | | | | | | | |
|---|---|---|---|---|---|---|---|---|---|---|---|---|---|---|
| Val | Thr | Tyr | Leu<br>260 | Met | Asp | Met | Cys | Ser<br>265 | Phe | Asp | Thr | Ile | Ser<br>270 | Thr | Ser |
| Thr | Val | Asp<br>275 | Thr | Lys | Leu | Ser | Pro<br>280 | Phe | Cys | Asp | Leu | Phe<br>285 | Thr | His | Asp |
| Glu | Trp<br>290 | Ile | His | Tyr | Asp | Tyr<br>295 | Leu | Gln | Ser | Leu | Lys<br>300 | Lys | Tyr | Tyr | Gly |
| His<br>305 | Gly | Ala | Gly | Asn | Pro<br>310 | Leu | Gly | Pro | Thr | Gln<br>315 | Gly | Val | Gly | Tyr | Ala<br>320 |
| Asn | Glu | Leu | Ile | Ala<br>325 | Arg | Leu | Thr | His | Ser<br>330 | Pro | Val | His | Asp | Asp<br>335 | Thr |
| Ser | Ser | Asn | His<br>340 | Thr | Leu | Asp | Ser | Asn<br>345 | Pro | Ala | Thr | Phe | Pro<br>350 | Leu | Asn |
| Ser | Thr | Leu<br>355 | Tyr | Ala | Asp | Phe | Ser<br>360 | His | Asp | Asn | Gly | Ile<br>365 | Ile | Ser | Ile |
| Leu | Phe<br>370 | Ala | Leu | Gly | Leu | Tyr<br>375 | Asn | Gly | Thr | Lys | Pro<br>380 | Leu | Ser | Thr | Thr |
| Thr<br>385 | Val | Glu | Asn | Ile | Thr<br>390 | Gln | Thr | Asp | Gly | Phe<br>395 | Ser | Ser | Ala | Trp | Thr<br>400 |
| Val | Pro | Phe | Ala | Ser<br>405 | Arg | Leu | Tyr | Val | Glu<br>410 | Met | Met | Gln | Cys | Gln<br>415 | Ala |
| Glu | Gln | Glu | Pro<br>420 | Leu | Val | Arg | Val | Leu<br>425 | Val | Asn | Asp | Arg | Val<br>430 | Val | Pro |
| Leu | His | Gly<br>435 | Cys | Pro | Ile | Asp | Ala<br>440 | Leu | Gly | Arg | Cys | Thr<br>445 | Arg | Asp | Ser |
| Phe | Val<br>450 | Arg | Gly | Leu | Ser | Phe<br>455 | Ala | Arg | Ser | Gly | Gly<br>460 | Asp | Trp | Ala | Glu |
| Cys<br>465 | Ser | Ala | | | | | | | | | | | | | |

( 2 ) INFORMATION FOR SEQ ID NO:3:

( i ) SEQUENCE CHARACTERISTICS:
        ( A ) LENGTH: 2071 base pairs
        ( B ) TYPE: nucleic acid
        ( C ) STRANDEDNESS: both
        ( D ) TOPOLOGY: linear ( i i ) MOLECULE TYPE: cDNA ( i x ) FEATURE:
        ( A ) NAME/KEY: CDS
        ( B ) LOCATION: join(136..915, 970..1089, 1142..1245,
            1305..1737)

( x i ) SEQUENCE DESCRIPTION: SEQ ID NO:3:

```
GCATGCTGGA CCGCAATCTC CGATCGCCGG GTATAAAAGG TCCTCCAAAC CCCTCTCGGT        60

CGATATGTAC CCCGCTCGTC ATCTCCAATC CTCTCGAGAG CACCTTCTCC AGCTTTTGTC       120
```

| AATTGTACCT | TCGCA | ATG<br>Met<br>1 | CCT<br>Pro | CGC<br>Arg | ACC<br>Thr | TCT<br>Ser<br>5 | CTC<br>Leu | CTC<br>Leu | ACC<br>Thr | CTG<br>Leu | GCC<br>Ala | TGT<br>Cys<br>10 | GCT<br>Ala | 171 |
|---|---|---|---|---|---|---|---|---|---|---|---|---|---|---|

| CTG<br>Leu | GCC<br>Ala | ACG<br>Thr<br>15 | GGC<br>Gly | GCA<br>Ala | TCC<br>Ser | GCT<br>Ala | TTC<br>Phe<br>20 | TCC<br>Ser | TAC<br>Tyr | GGC<br>Gly | GCT<br>Ala | GCC<br>Ala<br>25 | ATT<br>Ile | CCT<br>Pro | CAG<br>Gln | 219 |
|---|---|---|---|---|---|---|---|---|---|---|---|---|---|---|---|---|

| TCA<br>Ser | ACC<br>Thr | CAG<br>Gln<br>30 | GAG<br>Glu | AAG<br>Lys | CAG<br>Gln | TTC<br>Phe | TCT<br>Ser<br>35 | CAG<br>Gln | GAG<br>Glu | TTC<br>Phe | CGC<br>Arg | GAT<br>Asp<br>40 | GGC<br>Gly | TAC<br>Tyr | AGC<br>Ser | 267 |
|---|---|---|---|---|---|---|---|---|---|---|---|---|---|---|---|---|

| ATC<br>Ile | CTC<br>Leu<br>45 | AAG<br>Lys | CAC<br>His | TAC<br>Tyr | GGT<br>Gly | GGT<br>Gly<br>50 | AAC<br>Asn | GGA<br>Gly | CCC<br>Pro | TAC<br>Tyr | TCC<br>Ser<br>55 | GAG<br>Glu | CGT<br>Arg | GTG<br>Val | TCC<br>Ser<br>60 | 315 |
|---|---|---|---|---|---|---|---|---|---|---|---|---|---|---|---|---|

| | | | | | | | | | | | | | | | | |
|---|---|---|---|---|---|---|---|---|---|---|---|---|---|---|---|---|
| TAC | GGT | ATC | GCT | CGC | GAT | CCC | CCG | ACC | AGC | TGC | GAG | GTC | GAT | CAG | GTC | 363 |
| Tyr | Gly | Ile | Ala | Arg | Asp | Pro | Pro | Thr | Ser | Cys | Glu | Val | Asp | Gln | Val | |
| | | | 65 | | | | 70 | | | | | | 75 | | | |
| ATC | ATG | GTC | AAG | CGT | CAC | GGA | GAG | CGC | TAC | CCG | TCC | CCT | TCA | GCC | GGC | 411 |
| Ile | Met | Val | Lys | Arg | His | Gly | Glu | Arg | Tyr | Pro | Ser | Pro | Ser | Ala | Gly | |
| | | | 80 | | | | 85 | | | | | 90 | | | | |
| AAG | GAC | ATC | GAA | GAG | GCC | CTG | GCC | AAG | GTC | TAC | AGC | ATC | AAC | ACT | ACT | 459 |
| Lys | Asp | Ile | Glu | Glu | Ala | Leu | Ala | Lys | Val | Tyr | Ser | Ile | Asn | Thr | Thr | |
| | | | 95 | | | | 100 | | | | 105 | | | | | |
| GAA | TAC | AAG | GGC | GAC | CTG | GCC | TTC | CTG | AAC | GAC | TGG | ACC | TAC | TAC | GTC | 507 |
| Glu | Tyr | Lys | Gly | Asp | Leu | Ala | Phe | Leu | Asn | Asp | Trp | Thr | Tyr | Tyr | Val | |
| | 110 | | | | | 115 | | | | | 120 | | | | | |
| CCT | AAT | GAG | TGC | TAC | TAC | AAC | GCC | GAG | ACC | ACC | AGC | GGC | CCC | TAC | GCC | 555 |
| Pro | Asn | Glu | Cys | Tyr | Tyr | Asn | Ala | Glu | Thr | Thr | Ser | Gly | Pro | Tyr | Ala | |
| 125 | | | | | 130 | | | | | 135 | | | | | 140 | |
| GGT | TTG | CTG | GAC | GCG | TAC | AAC | CAT | GGC | AAC | GAT | TAC | AAG | GCT | CGC | TAC | 603 |
| Gly | Leu | Leu | Asp | Ala | Tyr | Asn | His | Gly | Asn | Asp | Tyr | Lys | Ala | Arg | Tyr | |
| | | | | 145 | | | | | 150 | | | | | 155 | | |
| GGC | CAC | CTC | TGG | AAC | GGT | GAG | ACG | GTC | GTG | CCC | TTC | TTT | TCT | AGT | GGC | 651 |
| Gly | His | Leu | Trp | Asn | Gly | Glu | Thr | Val | Val | Pro | Phe | Phe | Ser | Ser | Gly | |
| | | | 160 | | | | | 165 | | | | | 170 | | | |
| TAC | GGA | CGT | GTC | ATC | GAG | ACG | GCC | CGC | AAG | TTC | GGT | GAG | GGT | TTC | TTT | 699 |
| Tyr | Gly | Arg | Val | Ile | Glu | Thr | Ala | Arg | Lys | Phe | Gly | Glu | Gly | Phe | Phe | |
| | | 175 | | | | | 180 | | | | | | 185 | | | |
| GGC | TAC | AAC | TAC | TCC | ACC | AAC | GCT | GCC | CTC | AAC | ATC | ATC | TCC | GAG | TCC | 747 |
| Gly | Tyr | Asn | Tyr | Ser | Thr | Asn | Ala | Ala | Leu | Asn | Ile | Ile | Ser | Glu | Ser | |
| | 190 | | | | | 195 | | | | | 200 | | | | | |
| GAG | GTC | ATG | GGC | GCG | GAC | AGC | CTC | ACG | CCC | ACC | TGT | GAC | ACC | GAC | AAC | 795 |
| Glu | Val | Met | Gly | Ala | Asp | Ser | Leu | Thr | Pro | Thr | Cys | Asp | Thr | Asp | Asn | |
| 205 | | | | | 210 | | | | | 215 | | | | | 220 | |
| GAC | CAG | ACC | ACC | TGC | GAC | AAC | CTG | ACT | TAC | CAG | CTG | CCC | CAG | TTC | AAG | 843 |
| Asp | Gln | Thr | Thr | Cys | Asp | Asn | Leu | Thr | Tyr | Gln | Leu | Pro | Gln | Phe | Lys | |
| | | | | 225 | | | | | 230 | | | | | 235 | | |
| GTC | GCT | GCT | GCC | CGC | CTA | AAC | TCC | CAG | AAC | CCC | GGC | ATG | AAC | CTC | ACC | 891 |
| Val | Ala | Ala | Ala | Arg | Leu | Asn | Ser | Gln | Asn | Pro | Gly | Met | Asn | Leu | Thr | |
| | | | 240 | | | | | 245 | | | | | 250 | | | |
| GCA | TCT | GAT | GTC | TAC | AAC | CTG | ATG | GGTATGTGAT | | TACGGTACAA | | TCATTGGCTC | | | | 945 |
| Ala | Ser | Asp | Val | Tyr | Asn | Leu | Met | | | | | | | | | |
| | | 255 | | | | | 260 | | | | | | | | | |
| AAACCTCCAG | | CTGACAGCAT | | CCTA | GTT | ATG | GCC | TCC | TTT | GAG | CTC | AAT | GCT | | | 996 |
| | | | | | Val | Met | Ala | Ser | Phe | Glu | Leu | Asn | Ala | | | |
| | | | | | | | | | | 265 | | | | | | |
| CGT | CCC | TTC | TCC | AAC | TGG | ATC | AAC | GCC | TTT | ACC | CAG | GAC | GAA | TGG | GTC | 1044 |
| Arg | Pro | Phe | Ser | Asn | Trp | Ile | Asn | Ala | Phe | Thr | Gln | Asp | Glu | Trp | Val | |
| 270 | | | | | 275 | | | | | 280 | | | | | 285 | |
| AGC | TTC | GGT | TAC | GTT | GAG | GAT | TTG | AAC | TAC | TAC | TAC | TGC | GCT | GGG | | 1089 |
| Ser | Phe | Gly | Tyr | Val | Glu | Asp | Leu | Asn | Tyr | Tyr | Tyr | Cys | Ala | Gly | | |
| | | | 290 | | | | | 295 | | | | | 300 | | | |
| TGAGTTTACC | | ATTTGATCCA | | TTATTGTCTT | | GGATCAGCTA | | ACGATCGATA | | GT | CCC | | | | | 1144 |
| | | | | | | | | | | | Pro | | | | | |
| GGT | GAC | AAG | AAC | ATG | GCT | GCT | GTG | GGT | GCC | GTC | TAC | GCC | AAC | GCC | AGT | 1192 |
| Gly | Asp | Lys | Asn | Met | Ala | Ala | Val | Gly | Ala | Val | Tyr | Ala | Asn | Ala | Ser | |
| | | | 305 | | | | | 310 | | | | | 315 | | | |
| CTC | ACC | CTC | CTG | AAC | CAG | GGA | CCC | AAG | GAA | GCC | GGC | TCC | TTG | TTC | TTC | 1240 |
| Leu | Thr | Leu | Leu | Asn | Gln | Gly | Pro | Lys | Glu | Ala | Gly | Ser | Leu | Phe | Phe | |
| | | 320 | | | | | 325 | | | | | 330 | | | | |
| AAC | TT | GTACGTTCTCG | | GCAGAATCAG | | AGTCTCACAA | | AAAGAAACTC | | TTCACTAACA | | | | | | 1296 |
| Asn | Phe | | | | | | | | | | | | | | | |
| 335 | | | | | | | | | | | | | | | | |

| | | | | | | | | | | | | | | | | |
|---|---|---|---|---|---|---|---|---|---|---|---|---|---|---|---|---|
| TATAGTAG | T | GCC | CAC | GAC | ACC | AAC | ATC | ACC | CCC | ATC | CTC | GCC | GCC | CTA | | 1344 |
| | | Ala | His | Asp | Thr | Asn 340 | Ile | Thr | Pro | Ile | Leu 345 | Ala | Ala | Leu | | |
| GGC | GTC | CTC | ATC | CCC | AAC | GAG | GAC | CTT | CCT | CTT | GAC | CGG | GTC | GCC | TTC | 1392 |
| Gly | Val 350 | Leu | Ile | Pro | Asn | Glu 355 | Asp | Leu | Pro | Leu | Asp 360 | Arg | Val | Ala | Phe | |
| GGC | AAC | CCC | TAC | TCG | ATC | GGC | AAC | ATC | GTG | CCC | ATG | GGT | GGC | CAT | CTG | 1440 |
| Gly 365 | Asn | Pro | Tyr | Ser | Ile 370 | Gly | Asn | Ile | Val | Pro 375 | Met | Gly | Gly | His | Leu 380 | |
| ACC | ATC | GAG | CGT | CTC | AGC | TGC | CAG | GCC | ACC | GCC | CTC | TCG | GAC | GAG | GGT | 1488 |
| Thr | Ile | Glu | Arg | Leu 385 | Ser | Cys | Gln | Ala | Thr 390 | Ala | Leu | Ser | Asp | Glu 395 | Gly | |
| ACC | TAC | GTG | CGT | CTG | GTG | CTG | AAC | GAG | GCT | GTA | CTC | CCC | TTC | AAC | GAC | 1536 |
| Thr | Tyr | Val | Arg 400 | Leu | Val | Leu | Asn | Glu 405 | Ala | Val | Leu | Pro | Phe 410 | Asn | Asp | |
| TGC | ACC | TCC | GGA | CCG | GGC | TAC | TCC | TGC | CCT | CTG | GCC | AAC | TAC | ACC | TCC | 1584 |
| Cys | Thr | Ser 415 | Gly | Pro | Gly | Tyr | Ser 420 | Cys | Pro | Leu | Ala | Asn 425 | Tyr | Thr | Ser | |
| ATC | CTG | AAC | AAG | AAT | CTG | CCA | GAC | TAC | ACG | ACC | ACC | TGC | AAT | GTC | TCT | 1632 |
| Ile | Leu 430 | Asn | Lys | Asn | Leu | Pro 435 | Asp | Tyr | Thr | Thr | Thr 440 | Cys | Asn | Val | Ser | |
| GCG | TCC | TAC | CCG | CAG | TAT | CTG | AGC | TTC | TGG | TGG | AAC | TAC | AAC | ACC | ACG | 1680 |
| Ala 445 | Ser | Tyr | Pro | Gln | Tyr 450 | Leu | Ser | Phe | Trp | Trp 455 | Asn | Tyr | Asn | Thr | Thr 460 | |
| ACG | GAG | CTG | AAC | TAC | CGC | TCT | AGC | CCT | ATT | GCC | TGC | CAG | GAG | GGT | GAT | 1728 |
| Thr | Glu | Leu | Asn | Tyr 465 | Arg | Ser | Ser | Pro | Ile 470 | Ala | Cys | Gln | Glu | Gly 475 | Asp | |
| GCT | ATG | GAC | TAGATGCAGA | GGGGTAGGTC | CCGGGATACT | TTAGTGATGA | | | | | | | | | | 1777 |
| Ala | Met | Asp | | | | | | | | | | | | | | |
| TTGATATTCA | AGTTTGGTGG | TGACGATCAC | CTTGTTAATA | GTCTTGTACA | GTCATACGGT | | | | | | | | | | | 1837 |
| GAATGTAAAT | AATGATAATA | GCAATGATAC | ATGTTGGAAT | CTCGTTTTGT | TCTTTGTGTG | | | | | | | | | | | 1897 |
| CATAGGCGCT | TTGGGGGTGT | ATTTTTAGGC | GTTAGACTTA | TTTTCAATTC | GTGTATAATG | | | | | | | | | | | 1957 |
| CGGTCAGTAA | ATGAATCATC | AATTATTCAA | ATGCAATGCT | GTATACGTGA | AACTATTGGG | | | | | | | | | | | 2017 |
| TTAAGACGCA | GCTACTAGCT | GACTGCTTGG | TTACTTTCTG | TGTACACCGC | ATGC | | | | | | | | | | | 2071 |

( 2 ) INFORMATION FOR SEQ ID NO:4:

( i ) SEQUENCE CHARACTERISTICS:
        ( A ) LENGTH: 479 amino acids
        ( B ) TYPE: amino acid
        ( C ) STRANDEDNESS: single
        ( D ) TOPOLOGY: Not Relevant ( i i ) MOLECULE TYPE: protein ( x i ) SEQUENCE DESCRIPTION: SEQ ID NO:4:

| | | | | | | | | | | | | | | |
|---|---|---|---|---|---|---|---|---|---|---|---|---|---|---|
| Met 1 | Pro | Arg | Thr | Ser 5 | Leu | Leu | Thr | Leu | Ala 10 | Cys | Ala | Leu | Ala | Thr 15 | Gly |
| Ala | Ser | Ala | Phe 20 | Ser | Tyr | Gly | Ala | Ala 25 | Ile | Pro | Gln | Ser | Thr 30 | Gln | Glu |
| Lys | Gln | Phe 35 | Ser | Gln | Glu | Phe | Arg 40 | Asp | Gly | Tyr | Ser | Ile 45 | Leu | Lys | His |
| Tyr | Gly 50 | Gly | Asn | Gly | Pro | Tyr 55 | Ser | Glu | Arg | Val | Ser 60 | Tyr | Gly | Ile | Ala |
| Arg 65 | Asp | Pro | Pro | Thr | Ser 70 | Cys | Glu | Val | Asp | Gln 75 | Val | Ile | Met | Val | Lys 80 |
| Arg | His | Gly | Glu | Arg 85 | Tyr | Pro | Ser | Pro | Ser 90 | Ala | Gly | Lys | Asp | Ile 95 | Glu |

```
Glu Ala Leu Ala Lys Val Tyr Ser Ile Asn Thr Thr Glu Tyr Lys Gly
            100                 105                 110
Asp Leu Ala Phe Leu Asn Asp Trp Thr Tyr Tyr Val Pro Asn Glu Cys
            115                 120                 125
Tyr Tyr Asn Ala Glu Thr Thr Ser Gly Pro Tyr Ala Gly Leu Leu Asp
        130                 135                 140
Ala Tyr Asn His Gly Asn Asp Tyr Lys Ala Arg Tyr Gly His Leu Trp
145                 150                 155                 160
Asn Gly Glu Thr Val Val Pro Phe Phe Ser Ser Gly Tyr Gly Arg Val
                165                 170                 175
Ile Glu Thr Ala Arg Lys Phe Gly Glu Gly Phe Phe Gly Tyr Asn Tyr
            180                 185                 190
Ser Thr Asn Ala Ala Leu Asn Ile Ile Ser Glu Ser Glu Val Met Gly
        195                 200                 205
Ala Asp Ser Leu Thr Pro Thr Cys Asp Thr Asp Asn Asp Gln Thr Thr
210                 215                 220
Cys Asp Asn Leu Thr Tyr Gln Leu Pro Gln Phe Lys Val Ala Ala Ala
225                 230                 235                 240
Arg Leu Asn Ser Gln Asn Pro Gly Met Asn Leu Thr Ala Ser Asp Val
                245                 250                 255
Tyr Asn Leu Met Val Met Ala Ser Phe Glu Leu Asn Ala Arg Pro Phe
            260                 265                 270
Ser Asn Trp Ile Asn Ala Phe Thr Gln Asp Glu Trp Val Ser Phe Gly
            275                 280                 285
Tyr Val Glu Asp Leu Asn Tyr Tyr Cys Ala Gly Pro Gly Asp Lys
            290                 295                 300
Asn Met Ala Ala Val Gly Ala Val Tyr Ala Asn Ala Ser Leu Thr Leu
305                 310                 315                 320
Leu Asn Gln Gly Pro Lys Glu Ala Gly Ser Leu Phe Phe Asn Phe Ala
                325                 330                 335
His Asp Thr Asn Ile Thr Pro Ile Leu Ala Ala Leu Gly Val Leu Ile
            340                 345                 350
Pro Asn Glu Asp Leu Pro Leu Asp Arg Val Ala Phe Gly Asn Pro Tyr
            355                 360                 365
Ser Ile Gly Asn Ile Val Pro Met Gly Gly His Leu Thr Ile Glu Arg
        370                 375                 380
Leu Ser Cys Gln Ala Thr Ala Leu Ser Asp Glu Gly Thr Tyr Val Arg
385                 390                 395                 400
Leu Val Leu Asn Glu Ala Val Leu Pro Phe Asn Asp Cys Thr Ser Gly
                405                 410                 415
Pro Gly Tyr Ser Cys Pro Leu Ala Asn Tyr Thr Ser Ile Leu Asn Lys
            420                 425                 430
Asn Leu Pro Asp Tyr Thr Thr Thr Cys Asn Val Ser Ala Ser Tyr Pro
            435                 440                 445
Gln Tyr Leu Ser Phe Trp Trp Asn Tyr Asn Thr Thr Thr Glu Leu Asn
        450                 455                 460
Tyr Arg Ser Ser Pro Ile Ala Cys Gln Glu Gly Asp Ala Met Asp
465                 470                 475
```

( 2 ) INFORMATION FOR SEQ ID NO:5:

( i ) SEQUENCE CHARACTERISTICS:
        ( A ) LENGTH: 7 amino acids
        ( B ) TYPE: amino acid
        ( C ) STRANDEDNESS: single
        ( D ) TOPOLOGY: Not Relevant ( i i ) MOLECULE TYPE: peptide ( x i ) SEQUENCE DESCRIPTION: SEQ ID NO:5:

Arg His Gly Xaa Arg Xaa Pro
1               5

( 2 ) INFORMATION FOR SEQ ID NO:6:

( i ) SEQUENCE CHARACTERISTICS:
        ( A ) LENGTH: 14 amino acids
        ( B ) TYPE: amino acid
        ( C ) STRANDEDNESS: single
        ( D ) TOPOLOGY: Not Relevant ( i i ) MOLECULE TYPE: peptide ( x i ) SEQUENCE DESCRIPTION: SEQ ID NO:6:

Leu Ala Val Pro Ala Ser Arg Asn Gln Ser Thr Xaa Asp Thr
1               5                   10

( 2 ) INFORMATION FOR SEQ ID NO:7:

( i ) SEQUENCE CHARACTERISTICS:
        ( A ) LENGTH: 14 amino acids
        ( B ) TYPE: amino acid
        ( C ) STRANDEDNESS: single
        ( D ) TOPOLOGY: Not Relevant ( i i ) MOLECULE TYPE: peptide ( x i ) SEQUENCE DESCRIPTION: SEQ ID NO:7:

Leu Ala Val Pro Ala Ser Arg Asn Gln Ser Ser Gly Asp Thr
1               5                   10

( 2 ) INFORMATION FOR SEQ ID NO:8:

( i ) SEQUENCE CHARACTERISTICS:
        ( A ) LENGTH: 16 amino acids
        ( B ) TYPE: amino acid
        ( C ) STRANDEDNESS: single
        ( D ) TOPOLOGY: Not Relevant ( i i ) MOLECULE TYPE: peptide ( x i ) SEQUENCE DESCRIPTION: SEQ ID NO:8:

Leu Tyr Val Glu Met Met Gln Asn Gln Ala Glu Gln Thr Pro Leu Val
1               5                   10                  15

( 2 ) INFORMATION FOR SEQ ID NO:9:

( i ) SEQUENCE CHARACTERISTICS:
        ( A ) LENGTH: 20 amino acids
        ( B ) TYPE: amino acid
        ( C ) STRANDEDNESS: single
        ( D ) TOPOLOGY: Not Relevant ( i i ) MOLECULE TYPE: peptide ( x i ) SEQUENCE DESCRIPTION: SEQ ID NO:9:

Met Met Gln Cys Gln Ala Glu Gln Glu Pro Leu Val Arg Val Leu Val
1               5                   10                  15

Asn Asp Arg Xaa
            20

( 2 ) INFORMATION FOR SEQ ID NO:10:

( i ) SEQUENCE CHARACTERISTICS:
        ( A ) LENGTH: 4 amino acids ( B ) TYPE: amino acid
        ( C ) STRANDEDNESS: single
        ( D ) TOPOLOGY: Not Relevant ( i i ) MOLECULE TYPE: peptide ( x i ) SEQUENCE DESCRIPTION: SEQ ID NO:10:

Lys  Asp  Pro  Arg
    1

( 2 ) INFORMATION FOR SEQ ID NO:11:

( i ) SEQUENCE CHARACTERISTICS:
        ( A ) LENGTH: 5 amino acids
        ( B ) TYPE: amino acid
        ( C ) STRANDEDNESS: single
        ( D ) TOPOLOGY: Not Relevant ( i i ) MOLECULE TYPE: peptide ( x i ) SEQUENCE DESCRIPTION: SEQ ID NO:11:

Lys  Asp  Pro  Arg  Ala
    1                   5

( 2 ) INFORMATION FOR SEQ ID NO:12:

( i ) SEQUENCE CHARACTERISTICS:
        ( A ) LENGTH: 14 amino acids
        ( B ) TYPE: amino acid
        ( C ) STRANDEDNESS: single
        ( D ) TOPOLOGY: Not Relevant ( i i ) MOLECULE TYPE: peptide ( i x ) FEATURE:
        ( A ) NAME/KEY: Modified-Site
        ( B ) LOCATION: 4
        ( C ) OTHER INFORMATION: /NOTE= "Can be His or Leu"

( x i ) SEQUENCE DESCRIPTION: SEQ ID NO:12:

Tyr  Tyr  Gly  Xaa  Gly  Ala  Gly  Asn  Pro  Leu  Gly  Pro  Thr  Gln
    1              5                        10

( 2 ) INFORMATION FOR SEQ ID NO:13:

( i ) SEQUENCE CHARACTERISTICS:
        ( A ) LENGTH: 14 amino acids
        ( B ) TYPE: amino acid
        ( C ) STRANDEDNESS: single
        ( D ) TOPOLOGY: Not Relevant ( i i ) MOLECULE TYPE: peptide ( x i ) SEQUENCE DESCRIPTION: SEQ ID NO:13:

Tyr  Tyr  Gly  His  Gly  Ala  Gly  Asn  Pro  Leu  Gly  Pro  Thr  Gln
    1              5                        10

( 2 ) INFORMATION FOR SEQ ID NO:14:

( i ) SEQUENCE CHARACTERISTICS:
        ( A ) LENGTH: 10 amino acids
        ( B ) TYPE: amino acid
        ( C ) STRANDEDNESS: single
        ( D ) TOPOLOGY: Not Relevant ( i i ) MOLECULE TYPE: peptide ( i x ) FEATURE:
        ( A ) NAME/KEY: Modified-Site
        ( B ) LOCATION: 5
        ( C ) OTHER INFORMATION: /note= "Can be Gln or Asn"

( x i ) SEQUENCE DESCRIPTION: SEQ ID NO:14:

Thr Gly Tyr Val Xaa Tyr Val Gln Met Gln
1               5                   10

( 2 ) INFORMATION FOR SEQ ID NO:15:

( i ) SEQUENCE CHARACTERISTICS:
      ( A ) LENGTH: 9 amino acids
      ( B ) TYPE: amino acid
      ( C ) STRANDEDNESS: single
      ( D ) TOPOLOGY: Not Relevant ( i i ) MOLECULE TYPE: peptide ( x i ) SEQUENCE DESCRIPTION: SEQ ID NO:15:

Ala Gln Pro Gly Gln Ala Ala Pro Lys
1               5

( 2 ) INFORMATION FOR SEQ ID NO:16:

( i ) SEQUENCE CHARACTERISTICS:
      ( A ) LENGTH: 9 amino acids
      ( B ) TYPE: amino acid
      ( C ) STRANDEDNESS: single
      ( D ) TOPOLOGY: Not Relevant ( i i ) MOLECULE TYPE: peptide ( x i ) SEQUENCE DESCRIPTION: SEQ ID NO:16:

Ala Gln Pro Gly Gln Ser Ser Pro Lys
1               5

( 2 ) INFORMATION FOR SEQ ID NO:17:

( i ) SEQUENCE CHARACTERISTICS:
      ( A ) LENGTH: 16 amino acids
      ( B ) TYPE: amino acid
      ( C ) STRANDEDNESS: single
      ( D ) TOPOLOGY: Not Relevant ( i i ) MOLECULE TYPE: peptide ( x i ) SEQUENCE DESCRIPTION: SEQ ID NO:17:

Leu Tyr Val Glu Met Met Gln Cys Gln Ala Glu Gln Glu Pro Leu Val
1               5                   10                  15

( 2 ) INFORMATION FOR SEQ ID NO:18:

( i ) SEQUENCE CHARACTERISTICS:
      ( A ) LENGTH: 9 amino acids
      ( B ) TYPE: amino acid
      ( C ) STRANDEDNESS: single
      ( D ) TOPOLOGY: Not Relevant ( i i ) MOLECULE TYPE: peptide ( x i ) SEQUENCE DESCRIPTION: SEQ ID NO:18:

Phe Ile Glu Gly Phe Gln Ser Asp Lys
1               5

( 2 ) INFORMATION FOR SEQ ID NO:19:

( i ) SEQUENCE CHARACTERISTICS:
      ( A ) LENGTH: 5 amino acids
      ( B ) TYPE: amino acid
      ( C ) STRANDEDNESS: single
      ( D ) TOPOLOGY: Not Relevant ( i i ) MOLECULE TYPE: peptide ( x i ) SEQUENCE DESCRIPTION: SEQ ID NO:19:

Tyr Ala Phe Leu Lys
1               5

( 2 ) INFORMATION FOR SEQ ID NO:20:

( i ) SEQUENCE CHARACTERISTICS:
      ( A ) LENGTH: 6 amino acids
      ( B ) TYPE: amino acid
      ( C ) STRANDEDNESS: single
      ( D ) TOPOLOGY: Not Relevant ( i i ) MOLECULE TYPE: peptide ( x i ) SEQUENCE DESCRIPTION: SEQ ID NO:20:

Gly Leu Ser Phe Ala Arg
1               5

( 2 ) INFORMATION FOR SEQ ID NO:21:

( i ) SEQUENCE CHARACTERISTICS:
      ( A ) LENGTH: 7 amino acids
      ( B ) TYPE: amino acid
      ( C ) STRANDEDNESS: single
      ( D ) TOPOLOGY: Not Relevant ( i i ) MOLECULE TYPE: peptide ( x i ) SEQUENCE DESCRIPTION: SEQ ID NO:21:

Val Ile Ala Ser Gly Glu Lys
1               5

( 2 ) INFORMATION FOR SEQ ID NO:22:

( i ) SEQUENCE CHARACTERISTICS:
      ( A ) LENGTH: 4 amino acids
      ( B ) TYPE: amino acid
      ( C ) STRANDEDNESS: single
      ( D ) TOPOLOGY: Not Relevant ( i i ) MOLECULE TYPE: peptide ( x i ) SEQUENCE DESCRIPTION: SEQ ID NO:22:

Phe Tyr Gln Arg
1

( 2 ) INFORMATION FOR SEQ ID NO:23:

( i ) SEQUENCE CHARACTERISTICS:
      ( A ) LENGTH: 5 amino acids
      ( B ) TYPE: amino acid
      ( C ) STRANDEDNESS: single
      ( D ) TOPOLOGY: Not Relevant ( i i ) MOLECULE TYPE: peptide ( x i ) SEQUENCE DESCRIPTION: SEQ ID NO:23:

Asp Ser Phe Val Arg
1               5

( 2 ) INFORMATION FOR SEQ ID NO:24:

( i ) SEQUENCE CHARACTERISTICS:
      ( A ) LENGTH: 5 amino acids
      ( B ) TYPE: amino acid
      ( C ) STRANDEDNESS: single
      ( D ) TOPOLOGY: Not Relevant ( i i ) MOLECULE TYPE: peptide ( i x ) FEATURE:
    ( A ) NAME/KEY: Modified-Site
    ( B ) LOCATION: 1
    ( C ) OTHER INFORMATION: /note= "Can be Val or Tyr"

( i x ) FEATURE:
    ( A ) NAME/KEY: Modified-Site
    ( B ) LOCATION: 2
    ( C ) OTHER INFORMATION: /note= "Can be Leu or Glu"

( i x ) FEATURE:
    ( A ) NAME/KEY: Modified-Site
    ( B ) LOCATION: 3
    ( C ) OTHER INFORMATION: /note= "Can be Val or Ser"

( i x ) FEATURE:
    ( A ) NAME/KEY: Modified-Site
    ( B ) LOCATION: 4
    ( C ) OTHER INFORMATION: /note= "Can be Asn or Leu"

( i x ) FEATURE:
    ( A ) NAME/KEY: Modified-Site
    ( B ) LOCATION: 5
    ( C ) OTHER INFORMATION: /note= "Can be Asp or Gln"

( x i ) SEQUENCE DESCRIPTION: SEQ ID NO:24:

Xaa Xaa Xaa Xaa Xaa
1               5

( 2 ) INFORMATION FOR SEQ ID NO:25:

( i ) SEQUENCE CHARACTERISTICS:
        ( A ) LENGTH: 6 amino acids
        ( B ) TYPE: amino acid
        ( C ) STRANDEDNESS: single
        ( D ) TOPOLOGY: Not Relevant ( i i ) MOLECULE TYPE: peptide ( x i ) SEQUENCE DESCRIPTION: SEQ ID NO:25:

Tyr Glu Ser Leu Thr Arg
1               5

( 2 ) INFORMATION FOR SEQ ID NO:26:

( i ) SEQUENCE CHARACTERISTICS:
        ( A ) LENGTH: 7 amino acids
        ( B ) TYPE: amino acid
        ( C ) STRANDEDNESS: single
        ( D ) TOPOLOGY: Not Relevant ( i i ) MOLECULE TYPE: peptide ( x i ) SEQUENCE DESCRIPTION: SEQ ID NO:26:

Ser Ala Ala Ser Leu Asn Ser
1               5

( 2 ) INFORMATION FOR SEQ ID NO:27:

( i ) SEQUENCE CHARACTERISTICS:
        ( A ) LENGTH: 5 amino acids
        ( B ) TYPE: amino acid
        ( C ) STRANDEDNESS: single
        ( D ) TOPOLOGY: Not Relevant ( i i ) MOLECULE TYPE: peptide ( x i ) SEQUENCE DESCRIPTION: SEQ ID NO:27:

Leu Lys Asp Pro Arg
1               5

( 2 ) INFORMATION FOR SEQ ID NO:28:

( i ) SEQUENCE CHARACTERISTICS:
    ( A ) LENGTH: 6 amino acids
    ( B ) TYPE: amino acid
    ( C ) STRANDEDNESS: single
    ( D ) TOPOLOGY: Not Relevant ( i i ) MOLECULE TYPE: peptide ( x i ) SEQUENCE DESCRIPTION: SEQ ID NO:28:

Tyr Pro Thr Glu Ser Lys
1               5

( 2 ) INFORMATION FOR SEQ ID NO:29:

( i ) SEQUENCE CHARACTERISTICS:
        ( A ) LENGTH: 5 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Modified-Site
        ( B ) LOCATION: 1
        ( C ) OTHER INFORMATION: /note= "Can be Tyr or Asp"

( i x ) FEATURE:
        ( A ) NAME/KEY: Modified-Site
        ( B ) LOCATION: 2
        ( C ) OTHER INFORMATION: /note= "Can be Phe or Pro"

( i x ) FEATURE:
        ( A ) NAME/KEY: Modified-Site
        ( B ) LOCATION: 3
        ( C ) OTHER INFORMATION: /note= "Can be Asn or Ala"

( i x ) FEATURE:
        ( A ) NAME/KEY: Modified-Site
        ( B ) LOCATION: 4
        ( C ) OTHER INFORMATION: /note= "Can be any amino acid"

( x i ) SEQUENCE DESCRIPTION: SEQ ID NO:29:

Xaa Xaa Xaa Xaa Gly
1               5

( 2 ) INFORMATION FOR SEQ ID NO:30:

( i ) SEQUENCE CHARACTERISTICS:
        ( A ) LENGTH: 10 amino acids
        ( B ) TYPE: amino acid
        ( C ) STRANDEDNESS: single
        ( D ) TOPOLOGY: Not Relevant ( i i ) MOLECULE TYPE: peptide ( i x ) FEATURE:
        ( A ) NAME/KEY: Modified-Site
        ( B ) LOCATION: 3
        ( C ) OTHER INFORMATION: /note= "Can be Asn or Pro"

( i x ) FEATURE:
        ( A ) NAME/KEY: Modified-Site
        ( B ) LOCATION: 4
        ( C ) OTHER INFORMATION: /note= "Can be Asp or Phe"

( i x ) FEATURE:
        ( A ) NAME/KEY: Modified-Site
        ( B ) LOCATION: 6
        ( C ) OTHER INFORMATION: /note= "Can be Asp or Ser"

( i x ) FEATURE:
        ( A ) NAME/KEY: Modified-Site
        ( B ) LOCATION: 7
        ( C ) OTHER INFORMATION: /note= "Can be Gly or Leu"

( i x ) FEATURE:
  ( A ) NAME/KEY: Modified-Site
  ( B ) LOCATION: 8
  ( C ) OTHER INFORMATION: /note= "Can be Phe or Val"

( x i ) SEQUENCE DESCRIPTION: SEQ ID NO:30:

```
Leu Glu Xaa Xaa Leu Xaa Xaa Xaa Thr Leu
1               5                   10
```

( 2 ) INFORMATION FOR SEQ ID NO:31:

( i ) SEQUENCE CHARACTERISTICS:
    ( A ) LENGTH: 11 amino acids
    ( B ) TYPE: amino acid
    ( C ) STRANDEDNESS: single
    ( D ) TOPOLOGY: Not Relevant ( i i ) MOLECULE TYPE: peptide ( x i ) SEQUENCE DESCRIPTION: SEQ ID NO:31:

```
Leu Glu Asn Asp Leu Ser Gly Val Thr Leu Thr
1               5                   10
```

( 2 ) INFORMATION FOR SEQ ID NO:32:

( i ) SEQUENCE CHARACTERISTICS:
    ( A ) LENGTH: 24 amino acids
    ( B ) TYPE: amino acid
    ( C ) STRANDEDNESS: single
    ( D ) TOPOLOGY: Not Relevant ( i i ) MOLECULE TYPE: peptide ( x i ) SEQUENCE DESCRIPTION: SEQ ID NO:32:

```
Tyr Tyr Gly His Gly Ala Gly Asn Pro Leu Gly Pro Thr Gln Gly Val
1               5                   10                  15
Gly Tyr Ala Asn Glu Leu Ile Ala
                20
```

( 2 ) INFORMATION FOR SEQ ID NO:33:

( i ) SEQUENCE CHARACTERISTICS:
    ( A ) LENGTH: 8 amino acids
    ( B ) TYPE: amino acid
    ( C ) STRANDEDNESS: single
    ( D ) TOPOLOGY: Not Relevant ( i i ) MOLECULE TYPE: peptide ( x i ) SEQUENCE DESCRIPTION: SEQ ID NO:33:

```
Val Tyr Phe Ala Gln Val Leu Ser
1               5
```

( 2 ) INFORMATION FOR SEQ ID NO:34:

( i ) SEQUENCE CHARACTERISTICS:
    ( A ) LENGTH: 8 amino acids
    ( B ) TYPE: amino acid
    ( C ) STRANDEDNESS: single
    ( D ) TOPOLOGY: Not Relevant ( i i ) MOLECULE TYPE: peptide ( x i ) SEQUENCE DESCRIPTION: SEQ ID NO:34:

```
Val Thr Phe Ala Gln Val Leu Ser
1               5
```

( 2 ) INFORMATION FOR SEQ ID NO:35:

( i ) SEQUENCE CHARACTERISTICS:
  ( A ) LENGTH: 8 amino acids
  ( B ) TYPE: amino acid
  ( C ) STRANDEDNESS: single
  ( D ) TOPOLOGY: Not Relevant ( i i ) MOLECULE TYPE: peptide ( x i ) SEQUENCE DESCRIPTION: SEQ ID NO:35:

Phe Ile Glu Gly Phe Gln Ser Thr
1               5

( 2 ) INFORMATION FOR SEQ ID NO:36:

( i ) SEQUENCE CHARACTERISTICS:
  ( A ) LENGTH: 7 amino acids
  ( B ) TYPE: amino acid
  ( C ) STRANDEDNESS: single
  ( D ) TOPOLOGY: Not Relevant ( i i ) MOLECULE TYPE: peptide ( x i ) SEQUENCE DESCRIPTION: SEQ ID NO:36:

Asx Tyr Leu Gln Ser Leu Lys
1               5

( 2 ) INFORMATION FOR SEQ ID NO:37:

( i ) SEQUENCE CHARACTERISTICS:
  ( A ) LENGTH: 7 amino acids
  ( B ) TYPE: amino acid
  ( C ) STRANDEDNESS: single
  ( D ) TOPOLOGY: Not Relevant ( i i ) MOLECULE TYPE: peptide ( x i ) SEQUENCE DESCRIPTION: SEQ ID NO:37:

Asp Tyr Leu Gln Ser Leu Lys
1               5

( 2 ) INFORMATION FOR SEQ ID NO:38:

( i ) SEQUENCE CHARACTERISTICS:
  ( A ) LENGTH: 8 amino acids
  ( B ) TYPE: amino acid
  ( C ) STRANDEDNESS: single
  ( D ) TOPOLOGY: Not Relevant ( i i ) MOLECULE TYPE: peptide ( x i ) SEQUENCE DESCRIPTION: SEQ ID NO:38:

Asn Ile Glu Pro Phe Gln Val Asn
1               5

( 2 ) INFORMATION FOR SEQ ID NO:39:

( i ) SEQUENCE CHARACTERISTICS:
  ( A ) LENGTH: 6 amino acids
  ( B ) TYPE: amino acid
  ( C ) STRANDEDNESS: single
  ( D ) TOPOLOGY: Not Relevant ( i i ) MOLECULE TYPE: peptide ( x i ) SEQUENCE DESCRIPTION: SEQ ID NO:39:

Val Leu Val Asn Asp Arg
1               5

( 2 ) INFORMATION FOR SEQ ID NO:40:

( i ) SEQUENCE CHARACTERISTICS:
    ( A ) LENGTH: 14 amino acids
    ( B ) TYPE: amino acid
    ( C ) STRANDEDNESS: single
    ( D ) TOPOLOGY: Not Relevant ( i i ) MOLECULE TYPE: peptide ( x i ) SEQUENCE DESCRIPTION: SEQ ID NO:40:

```
Leu Ala Val Pro Ala Ser Arg Asn Gln Ser Thr Cys Asp Thr
 1               5                  10
```

( 2 ) INFORMATION FOR SEQ ID NO:41:

( i ) SEQUENCE CHARACTERISTICS:
    ( A ) LENGTH: 23 amino acids
    ( B ) TYPE: amino acid
    ( C ) STRANDEDNESS: single
    ( D ) TOPOLOGY: Not Relevant ( i i ) MOLECULE TYPE: peptide ( x i ) SEQUENCE DESCRIPTION: SEQ ID NO:41:

```
Phe Ser Tyr Gly Ala Ala Ile Pro Gln Ser Thr Gln Glu Lys Gln Phe
 1               5                  10                  15

Ser Gln Glu Phe Arg Asp Gly
                20
```

( 2 ) INFORMATION FOR SEQ ID NO:42:

( i ) SEQUENCE CHARACTERISTICS:
    ( A ) LENGTH: 4 amino acids
    ( B ) TYPE: amino acid
    ( C ) STRANDEDNESS: single
    ( D ) TOPOLOGY: Not Relevant ( i i ) MOLECULE TYPE: peptide ( x i ) SEQUENCE DESCRIPTION: SEQ ID NO:42:

```
Phe Ser Ser Gly
 1
```

( 2 ) INFORMATION FOR SEQ ID NO:43:

( i ) SEQUENCE CHARACTERISTICS:
    ( A ) LENGTH: 7 amino acids
    ( B ) TYPE: amino acid
    ( C ) STRANDEDNESS: single
    ( D ) TOPOLOGY: Not Relevant ( i i ) MOLECULE TYPE: peptide ( x i ) SEQUENCE DESCRIPTION: SEQ ID NO:43:

```
Arg His Gly Xaa Arg Xaa Pro
 1               5
```

( 2 ) INFORMATION FOR SEQ ID NO:44:

( i ) SEQUENCE CHARACTERISTICS:
    ( A ) LENGTH: 13 amino acids
    ( B ) TYPE: amino acid
    ( C ) STRANDEDNESS: single
    ( D ) TOPOLOGY: Not Relevant ( i i ) MOLECULE TYPE: peptide ( x i ) SEQUENCE DESCRIPTION: SEQ ID NO:44:

```
Arg His Gly Glu Arg Tyr Pro Ser Pro Ser Ala Gly Lys
 1               5                  10
```

( 2 ) INFORMATION FOR SEQ ID NO:45:

( i ) SEQUENCE CHARACTERISTICS:
        ( A ) LENGTH: 14 amino acids
        ( B ) TYPE: amino acid
        ( C ) STRANDEDNESS: single
        ( D ) TOPOLOGY: Not Relevant ( i i ) MOLECULE TYPE: peptide ( x i ) SEQUENCE DESCRIPTION: SEQ ID NO:45:

```
Phe Ser Tyr Gly Ala Ala Ile Pro Gln Ser Thr Gln Glu Lys
1               5                   10
```

( 2 ) INFORMATION FOR SEQ ID NO:46:

( i ) SEQUENCE CHARACTERISTICS:
        ( A ) LENGTH: 8 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:46:

```
Asp Ile Glu Glu Ala Leu Ala Lys
1               5
```

( 2 ) INFORMATION FOR SEQ ID NO:47:

( i ) SEQUENCE CHARACTERISTICS:
        ( A ) LENGTH: 4 amino acids
        ( B ) TYPE: amino acid
        ( C ) STRANDEDNESS: single
        ( D ) TOPOLOGY: Not Relevant ( i i ) MOLECULE TYPE: peptide ( i x ) FEATURE:
        ( A ) NAME/KEY: Modified-Site
        ( B ) LOCATION: 1
        ( C ) OTHER INFORMATION: /note= "Can be Ser or Ala"

( i x ) FEATURE:
        ( A ) NAME/KEY: Modified-Site
        ( B ) LOCATION: 3
        ( C ) OTHER INFORMATION: /note= "Can be Glu or Pro"

( x i ) SEQUENCE DESCRIPTION: SEQ ID NO:47:

```
Xaa Ile Xaa Glu
1
```

( 2 ) INFORMATION FOR SEQ ID NO:48:

( i ) SEQUENCE CHARACTERISTICS:
        ( A ) LENGTH: 19 amino acids
        ( B ) TYPE: amino acid
        ( C ) STRANDEDNESS: single
        ( D ) TOPOLOGY: Not Relevant ( i i ) MOLECULE TYPE: peptide ( x i ) SEQUENCE DESCRIPTION: SEQ ID NO:48:

```
Ala Arg Tyr Gly His Leu Trp Asn Gly Glu Thr Val Val Pro Phe Phe
1               5                   10                  15

Ser Ser Gly
```

( 2 ) INFORMATION FOR SEQ ID NO:49:

(i) SEQUENCE CHARACTERISTICS:
    (A) LENGTH: 12 amino acids
    (B) TYPE: amino acid
    (C) STRANDEDNESS: single
    (D) TOPOLOGY: Not Relevant (ii) MOLECULE TYPE: peptide (ix) FEATURE:
    (A) NAME/KEY: Modified-Site
    (B) LOCATION: 1
    (C) OTHER INFORMATION: /note= "Can be Ser or Arg"

(ix) FEATURE:
    (A) NAME/KEY: Modified-Site
    (B) LOCATION: 2
    (C) OTHER INFORMATION: /note= "Can be Tyr or His"

(ix) FEATURE:
    (A) NAME/KEY: Modified-Site
    (B) LOCATION: 4
    (C) OTHER INFORMATION: /note= "Can be Gly or Glu"

(ix) FEATURE:
    (A) NAME/KEY: Modified-Site
    (B) LOCATION: 5
    (C) OTHER INFORMATION: /note= "Can be Asn or Arg"

(ix) FEATURE:
    (A) NAME/KEY: Modified-Site
    (B) LOCATION: 6
    (C) OTHER INFORMATION: /note= "Can be Gly or Tyr"

(ix) FEATURE:
    (A) NAME/KEY: Modified-Site
    (B) LOCATION: 8
    (C) OTHER INFORMATION: /note= "Can be Tyr or Ser"

(ix) FEATURE:
    (A) NAME/KEY: Modified-Site
    (B) LOCATION: 10
    (C) OTHER INFORMATION: /note= "Can be Glu or Ser"

(xi) SEQUENCE DESCRIPTION: SEQ ID NO:49:

Xaa Xaa Gly Xaa Xaa Xaa Pro Xaa Pro Xaa Ala Gly
1               5                       10

(2) INFORMATION FOR SEQ ID NO:50:

(i) SEQUENCE CHARACTERISTICS:
    (A) LENGTH: 7 amino acids
    (B) TYPE: amino acid
    (C) STRANDEDNESS: single
    (D) TOPOLOGY: Not Relevant (ii) MOLECULE TYPE: peptide (xi) SEQUENCE DESCRIPTION: SEQ ID NO:50:

Tyr Gly Gly Asn Gly Pro Tyr
1               5

(2) INFORMATION FOR SEQ ID NO:51:

(i) SEQUENCE CHARACTERISTICS:
    (A) LENGTH: 11 amino acids
    (B) TYPE: amino acid
    (C) STRANDEDNESS: single
    (D) TOPOLOGY: Not Relevant (ii) MOLECULE TYPE: peptide (ix) FEATURE:
    (A) NAME/KEY: Modified-Site
    (B) LOCATION: 7
    (C) OTHER INFORMATION: /note= "Can be any amino acid"

( x i ) SEQUENCE DESCRIPTION: SEQ ID NO:51:

Gln Phe Ser Gln Glu Phe Xaa Asp Gly Tyr Arg
1               5                   10

( 2 ) INFORMATION FOR SEQ ID NO:52:

( i ) SEQUENCE CHARACTERISTICS:
        ( A ) LENGTH: 10 amino acids
        ( B ) TYPE: amino acid
        ( C ) STRANDEDNESS: single
        ( D ) TOPOLOGY: Not Relevant ( i i ) MOLECULE TYPE: peptide ( x i ) SEQUENCE DESCRIPTION: SEQ ID NO:52:

Gln Phe Ser Gln Glu Phe Arg Asp Gly Tyr
1               5                   10

( 2 ) INFORMATION FOR SEQ ID NO:53:

( i ) SEQUENCE CHARACTERISTICS:
        ( A ) LENGTH: 8 amino acids
        ( B ) TYPE: amino acid
        ( C ) STRANDEDNESS: single
        ( D ) TOPOLOGY: Not Relevant ( i i ) MOLECULE TYPE: peptide ( i x ) FEATURE:
        ( A ) NAME/KEY: Modified-Site
        ( B ) LOCATION: 1
        ( C ) OTHER INFORMATION: /note= "Can be Thr or His"

( i x ) FEATURE:
        ( A ) NAME/KEY: Modified-Site
        ( B ) LOCATION: 7
        ( C ) OTHER INFORMATION: /note= "Can be any amino acid"

( i x ) FEATURE:
        ( A ) NAME/KEY: Modified-Site
        ( B ) LOCATION: 8
        ( C ) OTHER INFORMATION: /note= "Can be Tyr or Pro"

( x i ) SEQUENCE DESCRIPTION: SEQ ID NO:53:

Xaa Tyr Gly Gly Asn Gly Xaa Xaa
1               5

( 2 ) INFORMATION FOR SEQ ID NO:54:

( i ) SEQUENCE CHARACTERISTICS:
        ( A ) LENGTH: 7 amino acids
        ( B ) TYPE: amino acid
        ( C ) STRANDEDNESS: single
        ( D ) TOPOLOGY: Not Relevant ( i i ) MOLECULE TYPE: peptide ( x i ) SEQUENCE DESCRIPTION: SEQ ID NO:54:

Phe Ser Ser Gly Tyr Gly Arg
1               5

( 2 ) INFORMATION FOR SEQ ID NO:55:

( i ) SEQUENCE CHARACTERISTICS:
        ( A ) LENGTH: 7 amino acids
        ( B ) TYPE: amino acid
        ( C ) STRANDEDNESS: single
        ( D ) TOPOLOGY: Not Relevant ( i i ) MOLECULE TYPE: peptide ( x i ) SEQUENCE DESCRIPTION: SEQ ID NO:55:

```
    Val Ala Phe Gly Asn Pro Tyr
    1               5
```

( 2 ) INFORMATION FOR SEQ ID NO:56:

( i ) SEQUENCE CHARACTERISTICS:
        ( A ) LENGTH: 7 amino acids
        ( B ) TYPE: amino acid
        ( C ) STRANDEDNESS: single
        ( D ) TOPOLOGY: Not Relevant ( i i ) MOLECULE TYPE: peptide ( i x ) FEATURE:
        ( A ) NAME/KEY: Modified-Site
        ( B ) LOCATION: 1
        ( C ) OTHER INFORMATION: /note= "Can be Asp or Glu"

( i x ) FEATURE:
        ( A ) NAME/KEY: Modified-Site
        ( B ) LOCATION: 7
        ( C ) OTHER INFORMATION: /note= "Can be Phe or Lys"

( x i ) SEQUENCE DESCRIPTION: SEQ ID NO:56:

```
    Xaa Leu Asn Ala Ile Leu Xaa
    1               5
```

( 2 ) INFORMATION FOR SEQ ID NO:57:

( i ) SEQUENCE CHARACTERISTICS:
        ( A ) LENGTH: 6 amino acids
        ( B ) TYPE: amino acid
        ( C ) STRANDEDNESS: single
        ( D ) TOPOLOGY: Not Relevant ( i i ) MOLECULE TYPE: peptide ( x i ) SEQUENCE DESCRIPTION: SEQ ID NO:57:

```
    Gln Leu Pro Gln Phe Lys
    1               5
```

( 2 ) INFORMATION FOR SEQ ID NO:58:

( i ) SEQUENCE CHARACTERISTICS:
        ( A ) LENGTH: 6 amino acids
        ( B ) TYPE: amino acid
        ( C ) STRANDEDNESS: single
        ( D ) TOPOLOGY: Not Relevant ( i i ) MOLECULE TYPE: peptide ( x i ) SEQUENCE DESCRIPTION: SEQ ID NO:58:

```
    Val Ser Tyr Gly Ile Ala
    1               5
```

( 2 ) INFORMATION FOR SEQ ID NO:59:

( i ) SEQUENCE CHARACTERISTICS:
        ( A ) LENGTH: 12 amino acids
        ( B ) TYPE: amino acid
        ( C ) STRANDEDNESS: single
        ( D ) TOPOLOGY: Not Relevant ( i i ) MOLECULE TYPE: peptide ( x i ) SEQUENCE DESCRIPTION: SEQ ID NO:59:

```
    Leu Tyr Val Glu Met Met Gln Cys Gln Ala Glu Gln
    1               5                   10
```

( 2 ) INFORMATION FOR SEQ ID NO:60:

( i ) SEQUENCE CHARACTERISTICS:
    ( A ) LENGTH: 17 bases
    ( B ) TYPE: nucleic acid
    ( C ) STRANDEDNESS: single
    ( D ) TOPOLOGY: linear ( i i ) MOLECULE TYPE:cDNA ( x i ) SEQUENCE DESCRIPTION: SEQ ID NO:60:

GCTTGGCATT GTACTAC 17

( 2 ) INFORMATION FOR SEQ ID NO:61:

( i ) SEQUENCE CHARACTERISTICS:
    ( A ) LENGTH: 17 bases
    ( B ) TYPE: nucleic acid
    ( C ) STRANDEDNESS: single
    ( D ) TOPOLOGY: linear ( i i ) MOLECULE TYPE: cDNA ( x i ) SEQUENCE DESCRIPTION: SEQ ID NO:61:

GCCTGACACT GTACTAC 17

( 2 ) INFORMATION FOR SEQ ID NO:62:

( i ) SEQUENCE CHARACTERISTICS:
    ( A ) LENGTH: 17 bases
    ( B ) TYPE: nucleic acid
    ( C ) STRANDEDNESS: single
    ( D ) TOPOLOGY: linear ( i i ) MOLECULE TYPE:cDNA ( i x ) FEATURE:
    ( A ) NAME/KEY: misc_feature
    ( B ) LOCATION: 6
    ( C ) OTHER INFORMATION: /note= "N is Inosine"

( x i ) SEQUENCE DESCRIPTION: SEQ ID NO:62:

GGGTANCGCT CGCCGTG 17

( 2 ) INFORMATION FOR SEQ ID NO:63:

( i ) SEQUENCE CHARACTERISTICS:
    ( A ) LENGTH: 17 bases
    ( B ) TYPE: nucleic acid
    ( C ) STRANDEDNESS: single
    ( D ) TOPOLOGY: linear ( i i ) MOLECULE TYPE: cDNA ( i x ) FEATURE:
    ( A ) NAME/KEY: misc_feature
    ( B ) LOCATION: 6
    ( C ) OTHER INFORMATION: /note= "N is Inosine"

( x i ) SEQUENCE DESCRIPTION: SEQ ID NO:63:

GGATANCTTT CACCATG 17

( 2 ) INFORMATION FOR SEQ ID NO:64:

( i ) SEQUENCE CHARACTERISTICS:
    ( A ) LENGTH: 17 bases
    ( B ) TYPE: nucleic acid
    ( C ) STRANDEDNESS: single
    ( D ) TOPOLOGY: linear ( i i ) MOLECULE TYPE: cDNA ( i x ) FEATURE:

(A) NAME/KEY: misc_feature
            (B) LOCATION: 6
            (C) OTHER INFORMATION: /note= "N is Inosine"

(xi) SEQUENCE DESCRIPTION: SEQ ID NO:64:

GGGTANCGCT CGCCGTG                                                                                  17

(2) INFORMATION FOR SEQ ID NO:65:

(i) SEQUENCE CHARACTERISTICS:
            (A) LENGTH: 17 bases
            (B) TYPE: nucleic acid
            (C) STRANDEDNESS: single
            (D) TOPOLOGY: linear (ii) MOLECULE TYPE: cDNA (ix) FEATURE:
            (A) NAME/KEY: misc_feature
            (B) LOCATION: 6
            (C) OTHER INFORMATION: /note= "N is Inosine"

(xi) SEQUENCE DESCRIPTION: SEQ ID NO:65:

GGGTANCGCT CCCCGTG                                                                                  17

(2) INFORMATION FOR SEQ ID NO:66:

(i) SEQUENCE CHARACTERISTICS:
            (A) LENGTH: 17 bases
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO:66:

CAACTGCCGC AATTTAA                                                                                  17

(2) INFORMATION FOR SEQ ID NO:67:

(i) SEQUENCE CHARACTERISTICS:
            (A) LENGTH: 17 bases
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO:67:

CAGCTACCAC AGTTCAA                                                                                  17

(2) INFORMATION FOR SEQ ID NO:68:

(i) SEQUENCE CHARACTERISTICS:
            (A) LENGTH: 17 bases
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO:68:

CAACTTCCTC AATTTAA                                                                                  17

(2) INFORMATION FOR SEQ ID NO:69:

(i) SEQUENCE CHARACTERISTICS:
            (A) LENGTH: 17 bases
            (B) TYPE: nucleic acid
            (C) STRANDEDNESS: single (D) TOPOLOGY: linear (i i) MOLECULE TYPE: cDNA (x i) SEQUENCE DESCRIPTION: SEQ ID NO:69:

CAACTCCCCC AATTTAA 17

(2) INFORMATION FOR SEQ ID NO:70:

(i) SEQUENCE CHARACTERISTICS:
        (A) LENGTH: 17 bases
        (B) TYPE: nucleic acid
        (C) STRANDEDNESS: single
        (D) TOPOLOGY: linear (i i) MOLECULE TYPE: cDNA (x i) SEQUENCE DESCRIPTION: SEQ ID NO:70:

CAATTACCGC AATTTAA 17

(2) INFORMATION FOR SEQ ID NO:71:

(i) SEQUENCE CHARACTERISTICS:
        (A) LENGTH: 17 bases
        (B) TYPE: nucleic acid
        (C) STRANDEDNESS: single
        (D) TOPOLOGY: linear (i i) MOLECULE TYPE: cDNA (x i) SEQUENCE DESCRIPTION: SEQ ID NO:71:

CAGTTGCCAC AGTTCAA 17

(2) INFORMATION FOR SEQ ID NO:72:

(i) SEQUENCE CHARACTERISTICS:
        (A) LENGTH: 17 bases
        (B) TYPE: nucleic acid
        (C) STRANDEDNESS: single
        (D) TOPOLOGY: linear (i i) MOLECULE TYPE: cDNA (x i) SEQUENCE DESCRIPTION: SEQ ID NO:72:

CAATTACCTC AATTTAA 17

(2) INFORMATION FOR SEQ ID NO:73:

(i) SEQUENCE CHARACTERISTICS:
        (A) LENGTH: 17 bases
        (B) TYPE: nucleic acid
        (C) STRANDEDNESS: single
        (D) TOPOLOGY: linear (i i) MOLECULE TYPE: cDNA (x i) SEQUENCE DESCRIPTION: SEQ ID NO:73:

CAATTACCCC AATTTAA 17

(2) INFORMATION FOR SEQ ID NO:74:

(i) SEQUENCE CHARACTERISTICS:
        (A) LENGTH: 6 amino acids
        (B) TYPE: amino acid
        (C) STRANDEDNESS: single
        (D) TOPOLOGY: Not Relevant (i i) MOLECULE TYPE: peptide (x i) SEQUENCE DESCRIPTION: SEQ ID NO:74:

```
        Gly  Thr  Arg  Asn  Gly  Thr
          1                5
```

( 2 ) INFORMATION FOR SEQ ID NO:75:

( i ) SEQUENCE CHARACTERISTICS:
        ( A ) LENGTH: 6 amino acids
        ( B ) TYPE: amino acid
        ( C ) STRANDEDNESS: single
        ( D ) TOPOLOGY: Not Relevant ( i i ) MOLECULE TYPE: peptide ( x i ) SEQUENCE DESCRIPTION: SEQ ID NO:75:

```
        Arg  Cys  Thr  Arg  Ala  Cys
          1                5
```

( 2 ) INFORMATION FOR SEQ ID NO:76:

( i ) SEQUENCE CHARACTERISTICS:
        ( A ) LENGTH: 18 bases
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:76:

CTACCCTCT GCATCTAG                                                                                                                                                                18

( 2 ) INFORMATION FOR SEQ ID NO:77:

( i ) SEQUENCE CHARACTERISTICS:
        ( A ) LENGTH: 28 bases
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:77:

GAATTCCGAG TCCGAGGTCA TGGGCGCG                                                                                             28

( 2 ) INFORMATION FOR SEQ ID NO:78:

( i ) SEQUENCE CHARACTERISTICS:
        ( A ) LENGTH: 27 bases
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:78:

GAATTCCCGG GACCTACCCC TCTGCAT                                                                                             27

( 2 ) INFORMATION FOR SEQ ID NO:79:

( i ) SEQUENCE CHARACTERISTICS:
        ( A ) LENGTH: 30 bases
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:79:

AGAAGAAATT TCTAGAACAG CAGCGATTGG                                                                                     30

( 2 ) INFORMATION FOR SEQ ID NO:80:

( i ) SEQUENCE CHARACTERISTICS:
      ( A ) LENGTH: 35 bases
      ( B ) TYPE: nucleic acid
      ( C ) STRANDEDNESS: single
      ( D ) TOPOLOGY: linear ( i i ) MOLECULE TYPE: cDNA ( x i ) SEQUENCE DESCRIPTION: SEQ ID NO:80:

CGAGAGCACC TTCTCTAGAT TTTGTCAAAT GTACC       35

( 2 ) INFORMATION FOR SEQ ID NO:81:

( i ) SEQUENCE CHARACTERISTICS:
      ( A ) LENGTH: 23 bases
      ( B ) TYPE: nucleic acid
      ( C ) STRANDEDNESS: single
      ( D ) TOPOLOGY: linear ( i i ) MOLECULE TYPE: cDNA ( x i ) SEQUENCE DESCRIPTION: SEQ ID NO:81:

ACCCTCACCG AACTTGCGGG CCG       23

( 2 ) INFORMATION FOR SEQ ID NO:82:

( i ) SEQUENCE CHARACTERISTICS:
      ( A ) LENGTH: 7 amino acids
      ( B ) TYPE: amino acid
      ( C ) STRANDEDNESS: single
      ( D ) TOPOLOGY: Not Relevant ( i i ) MOLECULE TYPE: peptide ( x i ) SEQUENCE DESCRIPTION: SEQ ID NO:82:

Arg His Gly Xaa Arg Xaa Pro
1             5

( 2 ) INFORMATION FOR SEQ ID NO:83:

( i ) SEQUENCE CHARACTERISTICS:
      ( A ) LENGTH: 18 amino acids
      ( B ) TYPE: amino acid
      ( C ) STRANDEDNESS: single
      ( D ) TOPOLOGY: Not Relevant ( i i ) MOLECULE TYPE: peptide ( x i ) SEQUENCE DESCRIPTION: SEQ ID NO:83:

Ala Gln Val Leu Ser Arg His Gly Ala Arg Tyr Pro Thr Glu Ser Lys
1             5                   10                  15
Gly Lys ( 2 ) INFORMATION FOR SEQ ID NO:84:

( i ) SEQUENCE CHARACTERISTICS:
      ( A ) LENGTH: 18 amino acids
      ( B ) TYPE: amino acid
      ( C ) STRANDEDNESS: single
      ( D ) TOPOLOGY: Not Relevant ( i i ) MOLECULE TYPE: peptide ( x i ) SEQUENCE DESCRIPTION: SEQ ID NO:84:

Val Ile Met Val Lys Arg His Gly Glu Arg Tyr Pro Ser Pro Ser Ala
1             5                   10                  15

Gly Lys ( 2 ) INFORMATION FOR SEQ ID NO:85:

( i ) SEQUENCE CHARACTERISTICS:
        ( A ) LENGTH: 18 amino acids
        ( B ) TYPE: amino acid
        ( C ) STRANDEDNESS: single
        ( D ) TOPOLOGY: Not Relevant ( i i ) MOLECULE TYPE: peptide ( x i ) SEQUENCE DESCRIPTION: SEQ ID NO:85:

```
Val  Val  Ile  Val  Ser  Arg  His  Gly  Val  Arg  Ala  Pro  Thr  Lys  Ala  Thr
1                  5                        10                       15

Gln  Leu
```

( 2 ) INFORMATION FOR SEQ ID NO:86:

( i ) SEQUENCE CHARACTERISTICS:
        ( A ) LENGTH: 18 amino acids
        ( B ) TYPE: amino acid
        ( C ) STRANDEDNESS: single
        ( D ) TOPOLOGY: Not Relevant ( i i ) MOLECULE TYPE: peptide ( x i ) SEQUENCE DESCRIPTION: SEQ ID NO:86:

```
Val  His  Thr  Leu  Gln  Arg  His  Gly  Ser  Arg  Asn  Pro  Thr  Gly  Gly  Asn
1                  5                        10                       15

Ala  Ala
```

( 2 ) INFORMATION FOR SEQ ID NO:87:

( i ) SEQUENCE CHARACTERISTICS:
        ( A ) LENGTH: 18 amino acids
        ( B ) TYPE: amino acid
        ( C ) STRANDEDNESS: single
        ( D ) TOPOLOGY: Not Relevant ( i i ) MOLECULE TYPE: peptide ( x i ) SEQUENCE DESCRIPTION: SEQ ID NO:87:

```
Leu  Gln  Met  Val  Gly  Arg  His  Gly  Glu  Arg  Tyr  Pro  Thr  Val  Ser  Leu
1                  5                        10                       15

Ala  Lys
```

( 2 ) INFORMATION FOR SEQ ID NO:88:

( i ) SEQUENCE CHARACTERISTICS:
        ( A ) LENGTH: 18 amino acids
        ( B ) TYPE: amino acid
        ( C ) STRANDEDNESS: single
        ( D ) TOPOLOGY: Not Relevant ( i i ) MOLECULE TYPE: peptide ( x i ) SEQUENCE DESCRIPTION: SEQ ID NO:88:

```
Leu  Gln  Met  Leu  Ala  Arg  His  Gly  Glu  Arg  Tyr  Pro  Thr  Tyr  Ser  Lys
1                  5                        10                       15

Gly  Ala
```

( 2 ) INFORMATION FOR SEQ ID NO:89:

( i ) SEQUENCE CHARACTERISTICS:
        ( A ) LENGTH: 18 amino acids
        ( B ) TYPE: amino acid (C) STRANDEDNESS: single
(D) TOPOLOGY: Not Relevant (ii) MOLECULE TYPE: peptide (xi) SEQUENCE DESCRIPTION: SEQ ID NO:89:

Val Thr Leu Leu Tyr Arg His Gly Asp Arg Ser Pro Val Lys Ala Tyr
1               5                   10                  15

Pro Lys (2) INFORMATION FOR SEQ ID NO:90:

(i) SEQUENCE CHARACTERISTICS:
    (A) LENGTH: 18 amino acids
    (B) TYPE: amino acid
    (C) STRANDEDNESS: single
    (D) TOPOLOGY: Not Relevant (ii) MOLECULE TYPE: peptide (xi) SEQUENCE DESCRIPTION: SEQ ID NO:90:

Val Thr Leu Val Phe Arg His Gly Asp Arg Gly Pro Ile Glu Thr Phe
1               5                   10                  15

Pro Asn (2) INFORMATION FOR SEQ ID NO:91:

(i) SEQUENCE CHARACTERISTICS:
    (A) LENGTH: 18 amino acids
    (B) TYPE: amino acid
    (C) STRANDEDNESS: single
    (D) TOPOLOGY: Not Relevant (ii) MOLECULE TYPE: peptide (xi) SEQUENCE DESCRIPTION: SEQ ID NO:91:

Val Thr Leu Leu Tyr Arg His Gly Asp Arg Ser Pro Val Lys Thr Tyr
1               5                   10                  15

Pro Lys (2) INFORMATION FOR SEQ ID NO:92:

(i) SEQUENCE CHARACTERISTICS:
    (A) LENGTH: 18 amino acids
    (B) TYPE: amino acid
    (C) STRANDEDNESS: single
    (D) TOPOLOGY: Not Relevant (ii) MOLECULE TYPE: peptide (xi) SEQUENCE DESCRIPTION: SEQ ID NO:92:

Val Thr Leu Val Phe Arg His Gly Asp Arg Ser Pro Ile Asp Thr Phe
1               5                   10                  15

Pro Thr (2) INFORMATION FOR SEQ ID NO:93:

(i) SEQUENCE CHARACTERISTICS:
    (A) LENGTH: 84 bases
    (B) TYPE: nucleic acid
    (C) STRANDEDNESS: single
    (D) TOPOLOGY: linear (ii) MOLECULE TYPE: cDNA (xi) SEQUENCE DESCRIPTION: SEQ ID NO:93:

CTAGACACCT CAGCAATGTC GTTCCGATCT CTACTCGCCC TGAGCGGCCT CGTCTGCACA    60

```
GGGTTGGCAC  TGGCAGTCCC  CGCC                                                              84
```

( 2 ) INFORMATION FOR SEQ ID NO:94:

( i ) SEQUENCE CHARACTERISTICS:
        ( A ) LENGTH: 84 bases
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:94:

```
TCGAGGCGGG  GACTGCCAGT  GCCAACCCTG  TGCAGACGAG  GCCGCTCAGG  GCGAGTAGAG    60

ATCGGAACGA  CATTGCTGAG  GTGT                                              84
```